US007009048B2

(12) United States Patent
Uehira et al.

(10) Patent No.: US 7,009,048 B2
(45) Date of Patent: Mar. 7, 2006

(54) DYE-FORMING COUPLER, SILVER HALIDE PHOTOGRAPHIC LIGHT-SENSITIVE MATERIAL, AND METHOD FOR PRODUCING AN AZOMETHINE DYE

(75) Inventors: Shigeki Uehira, Minami-ashigara (JP); Jun Ogasawara, Minami-ashigara (JP); Kiyoshi Takeuchi, Minami-ashigara (JP); Yasuhiro Shimada, Minami-ashigara (JP); Yasuaki Deguchi, Minami-ashigara (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 0 days.

(21) Appl. No.: 10/912,122

(22) Filed: Aug. 6, 2004

(65) Prior Publication Data

US 2005/0020821 A1 Jan. 27, 2005

Related U.S. Application Data

(60) Division of application No. 10/270,055, filed on Oct. 15, 2002, now Pat. No. 6,803,181, which is a continuation of application No. 09/962,335, filed on Sep. 26, 2001, now abandoned.

(30) Foreign Application Priority Data

| | | |
|---|---|---|
| Sep. 27, 2000 | (JP) | 2000-294964 |
| Sep. 28, 2000 | (JP) | 2000-297609 |
| Mar. 30, 2001 | (JP) | 2000-101418 |

(51) Int. Cl.

| | |
|---|---|
| ***C07D 263/44*** | (2006.01) |
| ***C07D 403/06*** | (2006.01) |
| ***C07D 413/04*** | (2006.01) |
| ***C07D 417/04*** | (2006.01) |
| ***C09B 55/00*** | (2006.01) |

(52) U.S. Cl. ........................ 544/12; 544/182; 544/219; 544/279; 544/284; 544/319; 544/331; 544/333; 544/405; 546/271.4; 548/183; 548/226; 548/321.1

(58) Field of Classification Search .................. 544/12, 544/182, 219, 279, 284, 319, 331, 333, 405; 546/271.4; 548/183, 226, 321.1
See application file for complete search history.

(56) References Cited

U.S. PATENT DOCUMENTS

| | | | |
|---|---|---|---|
| 3,201,410 | A | 8/1965 | Morel et al. |
| 3,759,938 | A | 9/1973 | Giraudon |
| 3,806,597 | A | 4/1974 | Giraudon |
| 4,977,270 | A | 12/1990 | Wee |

FOREIGN PATENT DOCUMENTS

| | | |
|---|---|---|
| DE | 2135736 | 1/1972 |
| JP | 52-148070 | 12/1977 |

OTHER PUBLICATIONS

Renvall, Chemical Abstracts, 75:5764, 1971.*
Nakatani et al., Chemical Abstracts, 90:95404, 1979.*
Patton, Chemical Abstracts, 66:65420, 1967.*
Geffken, Chemical Abstracts, 97:182374, 1982.*
Research Disclosure Item 9939 (1972) pp. 74-76.
STN Interantional R Caplus Database, RN 10319-47-8; J. Org. Chem, (1967), 32(2), 383-8.
Abstract, JP 53/075930A, Jul. 5, 1978 (XP002189696).
Abstract, JP 56/1500070A, Nov. 20, 1981 (XP002189697).
XP002189695 (Beilstein Registry No. 5975454, CAS Registry No. 83490-80-6).

* cited by examiner

*Primary Examiner*—Fiona T. Powers
(74) *Attorney, Agent, or Firm*—Sughrue Mion, PLLC

(57) ABSTRACT

A dye-forming coupler of the formula (I). A silver halide photographic light-sensitive material that contains at least one dye-forming coupler of the formula (I). A method for producing an azomethine dye, which method comprises using a compound of the formula (I):

(I)

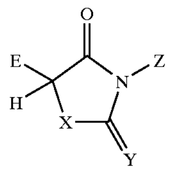

wherein E is an aryl, heterocyclic, or —C(=O)W group, in which W is a nitrogen-containing heterocyclic group, Z is an aryl or heterocyclic group, and X and Y each independently are =O, =S or =N—R, in which R is a substituent, with the proviso that when E is an aryl or heterocyclic group, X and Y each are =O, and that when E is a —C(=O)W group, Z is a substituted aryl group.

20 Claims, No Drawings

DYE-FORMING COUPLER, SILVER HALIDE PHOTOGRAPHIC LIGHT-SENSITIVE MATERIAL, AND METHOD FOR PRODUCING AN AZOMETHINE DYE

This is a divisional of application Ser. No. 10/270,055 filed Oct. 15, 2002, now U.S. Pat. No. 6,803,181, which is a continuation application of U.S. application Ser. No. 09/962,335 filed Sep. 26, 2001, now abandoned.

FIELD OF THE INVENTION

The present invention relates to a novel dye-forming coupler to form an azomethine dye, upon a coupling-reaction with an oxidized product of a developing agent, and to a silver halide photographic light-sensitive material containing said coupler. The present invention also relates to a method for producing an azomethine dye by using the above-mentioned reaction.

BACKGROUND OF THE INVENTION

In a silver halide photographic light-sensitive material (which may be referred to simply as a "light-sensitive material" hereinafter) using subtractive color processes, a color image can be formed from dyes having three primary colors, i.e. yellow, magenta, and cyan. In color photography using a current p-phenylenediamine-series color-developing agent, a β-acylacetanilide-series compound is used as a yellow coupler. However, the hue of the yellow dye obtained from this coupler is reddish, and it is difficult to obtain a hue of yellow having high purity. This dye has a small molecular extinction coefficient. Thus, in order to obtain a desired developed color density, a large amount of the coupler or silver halide is required. Therefore, the film thickness of the light-sensitive material becomes large, so that the sharpness of a resultant color image may drop. Such problems are caused. Furthermore, the above-mentioned dye is easily decomposed under high temperature and high humidity conditions, and the image storability thereof after development processing is insufficient. Thus improvement in this point is desired.

In order to solve these problems, the acyl group or the anilido group has been improved. Recently, the following have been proposed as improved couplers of conventional acylacetanilide: for example, 1-alkylcyclopropanecarbonylacetanilide-series compounds as described in JP-A-4-218,042 ("JP-A" means unexamined published Japanese patent application); cyclic malonediamide-type couplers as described in JP-A-5-11416; pyrrole-2 or 3-yl- or indole-2 or 3-yl-carbonylacetanilide-series couplers, as described, for example, in EP-953870A1, EP-953871A1, EP-953872A1, EP-953873A1, EP-953874A1 and EP-953875A1. Dyes formed from these couplers have improved hue and an improved molecular extinction coefficient, compared with conventional dyes. However, their image storability is still insufficient. Moreover, the synthesis routes of the couplers are long, since their structures have been made complicated. Thus, costs of the couplers are high. For these reasons, the couplers are not practical.

Research Disclosure Item 9939 (page 74, 1972) and JP-A-52-148070 describe couplers having a 2,4-oxazolidinedione structure. However, these couplers are unsatisfactory to solve the problems of the conventional couplers in both hue and a molecular extinction coefficient of the resultant dye.

SUMMARY OF THE INVENTION

The present invention is a dye-forming coupler represented by the following formula (I):

(I)

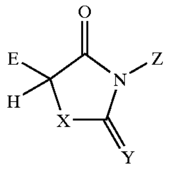

wherein E represents an aryl group or heterocyclic group, or a —C(═O)W group, in which W represents a nitrogen-containing heterocyclic group, Z represents an aryl group or a heterocyclic group, and X and Y each independently represent ═O, ═S, or ═N—R, in which R represents a substituent, with the proviso that when E represents an aryl group or a heterocyclic group, X and Y each represent ═O, and that when E represents a —C(═O)W group, Z represents a substituted aryl group.

Further, the present invention is a silver halide photographic light-sensitive material, which contains at least one dye-forming coupler represented by the above formula (I).

Still further, the present invention is a method for producing an azomethine dye, which method comprises using a compound represented by the following formula (IA):

(IA)

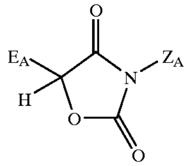

wherein $E_A$ and $Z_A$ each independently represent an aryl group or a heterocyclic group.

Other and further features and advantages of the invention will appear more fully from the following description.

DETAILED DESCRIPTION OF THE INVENTION

According to the present invention, there are provided the following means:

(1) A dye-forming coupler represented by the following formula (I):

(I)

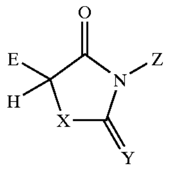

wherein E represents an aryl group or heterocyclic group, or a —C(═O)W group, in which W represents a nitrogen-containing heterocyclic group, and Z represent an aryl group or a heterocyclic group, and X and Y each independently represent ═O, ═S, or ═N—R, in which R represents a substituent, with the proviso that when E represents an aryl group or a heterocyclic group, X and Y each represent ═O, and that when E represents a —C(═O)W group, Z represents a substituted aryl group.

(2) The dye-forming coupler according to the above item (1), wherein the dye-forming coupler represented by formula (I) is represented by the following formula (IA):

(IA)

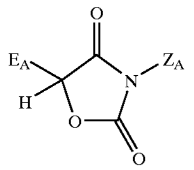

wherein, in formula (IA), $E_A$ and $Z_A$ each independently represent an aryl group or a heterocyclic group.

(3) The dye-forming coupler according to the above item (1), wherein the dye-forming coupler represented by formula (I) is represented by the following formula (IB):

formula (IB)

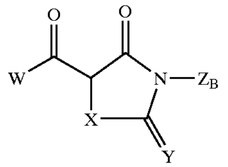

wherein, in formula (IB), W represents a nitrogen-containing heterocyclic group, $Z_B$ represents a substituted aryl group, and X and Y each independently represent =O, =S, or =N—R, in which R represents a substituent.

(4) A silver halide photographic light-sensitive material, containing at least one dye-forming coupler represented by the following formula (I):

(I)

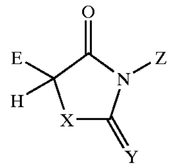

wherein E represents an aryl group or heterocyclic group, or a —C(=O)W group, in which W represents a nitrogen-containing heterocyclic group, Z represents an aryl group or a heterocyclic group, and X and Y each independently represent =O, =S, or =N—R, in which R represents a substituent, with the proviso that when E represents an aryl group or a heterocyclic group, X and Y each represent =O, and that when E represents a —C(=O)W group, Z represents a substituted aryl group.

(5) The silver halide photographic light-sensitive material according to the above item (4), wherein the dye-forming coupler represented by formula (I) is represented by the following formula (IA):

(IA)

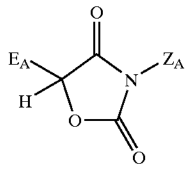

wherein, in formula (IA), $E_A$ and $Z_A$ each independently represent an aryl group or a heterocyclic group.

(6) The silver halide photographic light-sensitive material according to the above item (5), wherein, in the dye-forming coupler represented by formula (IA), $E_A$ is an aryl or heterocyclic group, having a substituent on at least one position adjacent to the carbon atom bonded to the oxazolidinedione ring.

(7) The silver halide photographic light-sensitive material according to the above item (5), wherein, in the dye-forming coupler represented by formula (IA), $E_A$ is an aryl or heterocyclic group, having substituents on both of positions adjacent to the carbon atom bonded to the oxazolidinedione ring.

(8) The silver halide photographic light-sensitive material according to any one of the above items (5) to (7), wherein, in the dye-forming coupler represented by formula (IA), $E_A$ is a heterocyclic group.

(9) The silver halide photographic light-sensitive material according to the above item (8), wherein the dye-forming coupler represented by formula (IA) is represented by the following formula (II):

(II)

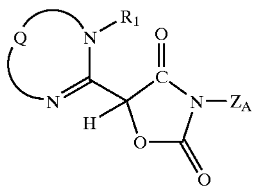

wherein, in formula (II), $Z_A$ represents an aryl group or a heterocyclic group, Q represents a group of atoms composed of carbon atoms and/or hetero atoms necessary to form, together with the N—C=N, a 5-, 6- or 7-membered ring, and $R_1$ represents a substituent.

(10) The silver halide photographic light-sensitive material according to the above item (9), wherein, in the dye-forming coupler represented by formula (II), Q is represented by the following formula (III):

(III)

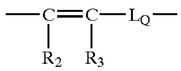

wherein, in formula (III), $L_Q$ represents a carbonyl or sulfonyl group, and $R_2$ and $R_3$, which are the same or different from, each represent a hydrogen atom or a substituent, or $R_2$ and $R_3$ may bond together to form a ring.

(11) The silver halide photographic light-sensitive material according to the above item (10), wherein when Q in the dye-forming coupler represented by formula (II) is represented by the formula (III), said $L_Q$ is a carbonyl group.

(12) The silver halide photographic light-sensitive material according to any one of the above items (5) to (11), wherein, in the dye-forming coupler represented by formula (IA), $Z_A$ is a heterocyclic group.

(13) The silver halide photographic light-sensitive material according to any one of the above items (5) to (11), wherein, in the dye-forming coupler represented by formula (IA), $Z_A$ is an aryl group having a substituent on an ortho position thereof.

(14) The silver halide photographic light-sensitive material according to the above item (5), wherein the dye-forming coupler represented by formula (IA) is represented by the following formula (IV):

(IV)

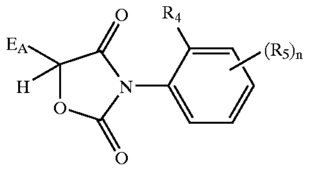

wherein, in formula (IV), $E_A$ represents an aryl group or a heterocyclic group; $R_4$ represents a halogen atom, an alkoxy group, or an aryloxy group; $R_5$ represents a substituent; and n is an integer of 0, or 1 to 4; when n is an integer of 2 to 4, $R_5$'s each are the same or different; or the groups adjacent to each other, among $R_4$ and $R_5$('s), may bond together to form a ring.

(15) The silver halide color photographic light-sensitive material according to the above item (4), wherein the dye-forming coupler represented by formula (I) is represented by the following formula (IB):

formula (IB)

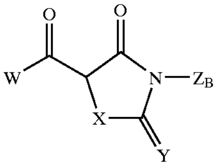

wherein, in formula (IB), W represents a nitrogen-containing heterocyclic group, $Z_B$ represents a substituted aryl group, and X and Y each independently represent =O, =S, or =N—R, in which R represents a substituent.

(16) A method for producing an azomethine dye, comprising using a compound represented by the following formula (I):

(I)

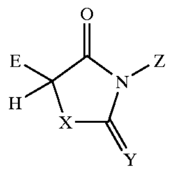

wherein E represents an aryl group or heterocyclic group, or a —C(=O)W group, in which W represents a nitrogen-containing heterocyclic group, Z represents an aryl group or a heterocyclic group, and X and Y each independently represent =O, =S, or =N—R, in which R represents a substituent, with the proviso that when E represents an aryl group or a heterocyclic group, X and Y each represent =O, and that when E represents a —C(=O)W group, Z represents a substituted aryl group.

(17) The method according to the above item (16), wherein the compound represented by formula (I) is represented by the following formula (IA):

(IA)

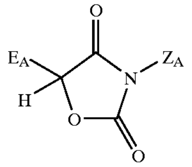

wherein, in formula (IA), $E_A$ and $Z_A$ each independently represent an aryl group or a heterocyclic group.

(18) The method according to the above item (17), wherein a p-phenylenediamine compound is used together with the compound represented by formula (IA).

(Herein, the dye-forming coupler represented by formula (IA) (e.g. those described in the above item (2)), and the light-sensitive material (e.g. those described in the above items (5) to (14)) and the method for producing an azomethine dye (e.g. those described in the above items (17) and (18)), each of which utilizes said compound of the formula (IA) are collectively referred to as a first embodiment of the present invention.)

(Herein, the dye-forming coupler represented by formula (IB) (e.g. those described in the above item (3)), and the light-sensitive material (e.g. those described in the above item (15) and the method for producing an azomethine dye, each of which utilizes said compound of the formula (IB) are collectively referred to as a second embodiment of the present invention.)

Herein, the present invention means to include both the first embodiment and the second embodiment, unless otherwise specified.

Hereinafter, the present invention will be described in detail.

(Dye-forming Coupler)

The dye-forming coupler of the present invention will be explained below, referring to the formulae (IA) and (IB), and these explanations, as they are, can also be applied to the formula (I) that includes said formulae (IA) and (IB).

The compound that may also be referred to as the dye-forming coupler, herein, represented by formula (IA), which is the first embodiment of the compound represented by formula (I) of the present invention, will be described in more detail Formula (IA):

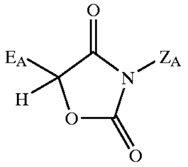

wherein $E_A$ and $Z_A$ each independently represent an aryl or heterocyclic group.

The aryl group represented by $E_A$ or $Z_A$ is preferably a substituted or unsubstituted aryl group having 6 to 30 carbon atoms. Examples thereof include phenyl, p-tolyl, naphthyl, m-chlorophenyl, and o-hexadecanoylaminophenyl. The heterocyclic group represented by $E_A$ or $Z_A$ is preferably a monovalent group in which one hydrogen atom is removed from a 5- or 6-membered, substituted or unsubstituted, and aromatic or non-aromatic heterocyclic compound; and it is more preferably a 5- or 6-membered aromatic heterocyclic group having 3 to 30 carbon atoms. Examples thereof include 2-furyl, 2-thienyl, 2-pyrimidinyl, and 2-benzothiazolyl.

Examples of the substituent in the substituted aryl or substituted heterocyclic group (that is, the substituent which the aryl or heterocyclic group may have) include halogen atoms, alkyl (including cycloalkyl and bicycloalkyl), alkenyl (including cycloalkenyl and bicycloalkenyl), alkynyl, aryl, heterocyclic, cyano, hydroxyl, nitro, carboxyl, alkoxy, aryloxy, silyloxy, heterocyclic oxy, acyloxy, carbamoyloxy, alkoxycarbonyloxy, aryloxycarbonyloxy, amino (including alkylamino and anilino), acylamino, aminocarbonylamino, alkoxycarbonylamino, aryloxycarbonylamino, sulfamoylamino, alkyl- and aryl-sulfonylamino, mercapto, alkylthio, arylthio, heterocyclic thio, sulfamoyl, sulfo, alkyl- and arylsulfinyl, alkyl- and aryl-sulfonyl, acyl, aryloxycarbonyl, alkoxycarbonyl, carbamoyl, aryl azo and heterocyclic azo, imido, phosphio, phosphinyl, phosphinyloxy, phosphinylamino, and silyl groups.

When the aryl or heterocyclic group is substituted with plural substituents, these substituents may be the same or different, or the substituents adjacent to each other may be bonded to each other to form a ring, preferably a 5- or 6-membered, saturated or unsaturated ring.

The above-mentioned substituent may be substituted with a substituent. Examples of this substituent are the same as described as the examples of the above-mentioned substituent.

The following will describe the substituent that the aryl or heterocyclic group represented by $E_A$ or $Z_A$ may have more specifically.

Examples of the substituent include the followings: halogen atoms (for example, chlorine, bromine and iodine atoms); alkyl groups (straight-chain or branched, substituted or unsubstituted alkyl groups, preferably alkyl groups having 1 to 30 carbon atoms, for example, methyl, ethyl, n-propyl, isopropyl, t-butyl, n-octyl, eicosyl, 2-chloroethyl, 2-cyanoethyl, and 2-ethylhexyl); cycloalkyl groups (preferably, substituted or unsubstituted cycloalkyl groups having 3 to 30 carbon atoms, for example, cyclohexyl, cyclopentyl, and 4-n-dodecylcyclohexyl; and including polycycloalkyl groups, for example, groups having a polycyclic structure, such as bicycloalkyl groups (preferably, substituted or unsubstituted bicycloalkyl groups having 5 to 30 carbon atoms, for example, bicyclo[1,2,2]heptane-2-yl and bicyclo [2,2,2]octane-3-yl), and tricycloalkyl groups. A monocyclic cycloalkyl and bicycloalkyl groups are preferred, and a monocyclic cycloalkyl group is particularly preferred.); alkenyl groups (straight-chain or branched, substituted or unsubstituted alkenyl groups, preferably alkenyl groups having 2 to 30 carbon atoms, for example, vinyl, allyl, prenyl, geranyl and oleyl); cycloalkenyl groups (preferably, substituted or unsubstituted cycloalkenyl groups having 3 to 30 carbon atoms, for example, 2-cyclopentene-1-yl and 2-cyclohexene-1-yl; further including polycycloalkenyl groups, for example, bicycloalkenyl groups (preferably, substituted or unsubstituted bicyloalkenyl groups having 5 to 30 carbon atoms, for example, bicyclo[2,2,1]hept-2-ene-1-yl and bicyclo[2,2,2]oct-2-ene-4-yl), and tricycloalkenyl groups. A monocyclic cycloalkenyl group is particularly preferred.); alkynyl groups (preferably, substituted or unsubstituted alkynyl groups having 2 to 30 carbon atoms, for example, ethynyl, propalgyl, and trimethylsilylethynyl); aryl groups (preferably, substituted or unsubstituted aryl groups having 6 to 30 carbon atoms, for example, phenyl, p-tolyl, naphthyl, m-chlorophenyl, o-hexadecanoylaminophenyl); heterocyclic groups (preferably, 5- or 6-membered, substituted or unsubstituted, and aromatic or non-aromatic heterocyclic groups, more preferably heterocyclic groups that have at least one hetero atom of nitrogen, oxygen or sulfur atoms and whose ring(s) is/are composed of atoms selected from carbon, nitrogen and sulfur atoms, and still more preferably 5- or 6-membered aromatic heterocyclic groups having 3 to 30 carbon atoms, for example, 2-furyl, 2-thienyl, 2-pyrrimidynyl, 2-benzothiazolyl); cyano group; hydroxyl group; nitro group; carboxyl group; alkoxy groups (preferably, substituted or unsubstituted alkoxy groups having 1 to 30 carbon atoms, for example, methoxy, ethoxy, isopropoxy, t-butoxy, n-octyloxy, and 2-methoxyethoxy); aryloxy groups (preferably, substituted or unsubstituted aryloxy groups having 6 to 30 carbon atoms, for example, phenoxy, 2-methylphenoxy, 4-t-butylphenoxy, 3-nitrophenoxy, 2-tetradecanoylaminophenoxy); silyloxy groups (preferably, silyloxy groups having-3 to 20 carbon atoms, for example, trimethylsilyloxy, and t-butyldimethylsilyloxy), heterocyclic oxy groups (preferably, substituted or unsubstituted heterocyclic oxy groups having 2 to 30 carbon atoms, the heterocyclic moiety thereof being preferably the heterocyclic moiety described about the above-mentioned heterocyclic group, for example, 1-phenyltetrazole-5-oxy, and 2-tetrahydropyrranyloxy); acyloxy groups (preferably, formyloxy, substituted or unsubstituted alkylcarbonyloxy groups having 2 to 30 carbon atoms, and substituted or unsubstituted arylcarbonyloxy groups having 6 to 30 carbon atoms, for example, formyloxy, acetyloxy, pyvaloyloxy, stearoyloxy, benzoyloxy, and p-methoxyphenylcarbonyloxy); carbamoyloxy groups (preferably, substituted or unsubstituted carbamoyloxy groups having 1 to 30 carbon atoms, for example, N,N-dimethylcarbamoyloxy, N,N-diethylcarbamoyloxy, morpholinocarbonyloxy, N,N-di-n-octylaminocarbonyloxy, and N-n-octylcarbamoyloxy); alkoxycarbonyloxy groups (preferably, substituted or unsubstituted alkoxycarbonyloxy groups having 2 to 30 carbon atoms, for example, methoxycarbonyloxy, ethoxycarbonyloxy, t-butoxycarbonyloxy, and n-octylcarbonyloxy); aryloxycarbonyloxy groups (preferably, substituted or unsubstituted aryloxycarbonyloxy groups having 7 to 30 carbon atoms, for example, phenoxycarbonyloxy, p-methoxyphenoxycarbonyloxy, and p-n-hexadecyloxyphenoxycarbonyloxy); amino groups (preferably, amino group, substituted or unsubstituted alkylamino groups having 1 to 30 carbon atoms, substituted or unsubstituted arylamino groups having 6 to 30 carbon atoms, and heterocyclic amino groups having 0 to 30 carbon atoms, for example, amino, methylamino, dimethylamino, anilino, N-methyl-anilino, diphenylamino, N-1,3,5-triazine-2-ylamino); acylamino groups (preferably, formylamino group, substituted or unsubstituted alkylcarbonylamino groups having 1 to 30 carbon atoms, and substituted or unsubstituted arylcarbonylamino groups having 6 to 30 carbon atoms, for example, formylamino, acetylamino, pyvaloylamino, lauroylamino, benzoylamino, 3,4,5-tri-n-octyloxyphenylcarbonylamino); aminocarbonylamino groups (preferably, substituted or unsubstituted aminocarbonylamino groups having 1 to 30 carbon atoms, for example, carbamoylamino, N,N-dimethylaminocarbonylamino, N,N-diethylaminocarbonylamino, and morpholinocarbonylamino), alkoxycarbonylamino groups (preferably, substituted or unsubstituted alkoxycarbonylamino groups having 2 to 30 carbon atoms, for example, methoxycarbonylamino, ethoxycarbonylamino, t-butoxycarbonylamino, n-octadecyloxycarbonylamino, and N-methyl-methoxycarbonylamino); aryloxycarbonylamino groups (preferably, substituted or unsubstituted aryloxycarbonylamino groups having 7 to 30 carbon atoms, for example, phenoxycarbonylamino, p-chlorophenoxycarbonylamino, and m-n-octyloxyphenoxycarbonylamino); sulfamoylamino groups (preferably, substituted or unsubstituted sulfamoylamino groups having 0 to 30 carbon atoms, for example, sulfamoylamino, N,N-dimethylaminosulfonylamino, and N-n-octylaminosulfonylamino); alkyl- and aryl-sulfonylamino groups (preferably, substituted or unsubstituted alkylsulfonylamino groups having 1 to 30 carbon atoms, and substituted or unsubstituted arylsulfonylamino groups having 6 to 30 carbon atoms, for example, methylsulfonylamino, butylsulfonylamino, phenylsulfonylamino, 2,3,5-trichlorophenylsulfonylamino, and p-methylphenylsulfonylamino); mercapto group; alkylthio groups (preferably, substituted or unsubstituted alkylthio groups having 1 to 30 carbon atoms, for example, methylthio, ethylthio, and n-hexadecylthio); arylthio groups (preferably, substituted or unsubstituted arylthio groups having 6 to 30 carbon atoms, for example, phenylthio, p-chlorophenylthio, and m-methoxyphenylthio); heterocyclic thio groups (preferably, substituted or unsubstituted heterocyclic thio groups having 2 to 30 carbon atoms, the heterocyclic moiety thereof being preferably the heterocyclic moiety described about the above-mentioned heterocyclic group, for example, 2-benzothiazolylthio, and 1-phenyltetrazole-5-ylthio); sulfamoyl groups (preferably, substituted or unsubstituted sulfamoyl groups having 0 to 30 carbon atoms, for example, N-ethylsulfamoyl, N-(3-dodecyloxypropyl)sulfamoyl, N,N-dimethylsulfamoyl, N-acetylsulfamoyl, N-benzoylsulfamoyl, N-(N'-phenylcarbamoyl)sulfamoyl); sulfo group; alkyl- and aryl-sulfinyl groups (preferably, substituted or unsubstituted alkylsulfinyl groups having 1 to 30 carbon atoms, and substituted or unsubstituted arylsulfinyl groups having 6 to 30 carbon atoms, for example, methylsulfinyl, ethylsulfinyl, phenylsulfinyl, and p-methylphenylsulfinyl); alkyl- and aryl-sulfonyl groups (preferably, substituted or unsubstituted alkylsulfonyl groups having 1 to 30 carbon atoms, and substituted or unsubstituted arylsulfonyl groups having 6 to 30 carbon atoms, for example, methylsulfonyl, ethylsulfonyl, phenylsulfonyl, p-methylphenylsulfonyl); acyl groups (preferably, formyl group, substituted or unsubstituted alkylcarbonyl groups having 2 to 30 carbon atoms, and substituted or unsubstituted arylcarbonyl groups having 7 to 30 carbon atoms, for example, acetyl, pyvaloyl, 2-chloroacetyl, stearoyl, benzoyl, and p-n-octyloxyphenylcarbonyl); aryloxycarbonyl groups (preferably, substituted or unsubstituted aryloxycarbonyl groups having 7 to 30 carbon atoms, for example, phenoxycarbonyl, o-chlorophenoxycarbonyl, m-nitrophenoxycarbonyl, and p-t-butylphenoxycarbonyl); alkoxycarbonyl groups (preferably, substituted or unsubstituted alkoxycarbonyl groups having 2 to 30 carbon atoms, for example, methoxycarbonyl, ethoxycarbonyl, t-butoxycarbonyl, and n-octadecyloxycarbonyl); carbamoyl groups (preferably, substituted or unsubstituted carbamoyl groups having 1 to 30 carbon atoms, for example, carbamoyl, N-methylcarbamoyl, N,N-dimethylcarbamoyl, N,N-di-n-octylcarbamoyl, and N-(methylsulfonyl)carbamoyl); aryl azo and heterocyclic azo groups (preferably, substituted or unsubstituted aryl azo groups having 6 to 30 carbon atoms, and substituted or unsubstituted heterocyclic azo groups having 3 to 30 carbon atoms (the heterocyclic moiety thereof being preferably the heterocyclic moiety described about the above-mentioned heterocyclic group), for example, phenyl azo, p-chlorophenyl azo, 5-ethylthio-1,3,4-thiadiazole-2-ylazo); imido groups (preferably, substituted or unsubstituted imido groups having 2 to 30 carbon atoms, for example, N-succinimido and N-phthalimido); phosphino groups (preferably, substituted or unsubstituted phosphino groups having 2 to 30 carbon atoms, for example, dimethylphosphino, diphenylphosphino, and methylphenoxyphosphino); phosphinyl groups (preferably, substituted or unsubstituted phosphinyl groups having 2 to 30 carbon atoms, for example, phosphinyl, dioctyloxyphosphinyl, and diethoxyphosphinyl); phosphinyloxy groups (preferably, substituted or unsubstituted phosphinyloxy groups having 2 to 30 carbon atoms, for example, diphenoxyphosphinyloxy, and dioctyloxyphosphinyloxy); phoshinylamino groups (preferably, substituted or unsubstituted phoshinylamino groups having 2 to 30 carbon atoms, for example, dimethoxyphoshinylamino, and dimethylaminophoshinylamino); and silyl groups (preferably, substituted or unsubstituted silyl groups having 3 to 30 carbon atoms, for example, trimethylsilyl, t-butyldimethylsilyl, and phenyldimethylsilyl).

About a group having a hydrogen atom, among the above-mentioned functional groups, it is allowable to remove the hydrogen atom and further substitute the group with another group (substituent) as described above. Examples of such a functional group include alkylcarbonylaminosulfonyl groups, arylcarbonylaminosulfonyl groups, alkylsulfonylaminocarbonyl groups, and arylsulfonylaminocarbonyl groups. More specific examples thereof include methylsulfonylaminocarbonyl, p-methylphenylsulfonylaminocarbonyl, acetylaminosulfonyl, and benzoylaminosulfonyl.

The substituents adjacent to each other may be bonded to each other to form a ring, preferably a 5- or 6-membered, saturated or unsaturated ring. The ring may be alicyclic, aromatic or heterocyclic. Examples thereof include benzene, furan, thiophene, cyclopentane, and cyclohexane rings.

The ring formed by binding each one of the substituents singly or a plurality of the substituents each other may be further substituted with a substituent, examples of which are groups given as examples of the substituent that the aryl or heterocyclic group represented by $E_A$ or $Z_A$ may have.

The total number of the carbon atoms in the substituent which the aryl or heterocyclic group represented by $E_A$ or $Z_A$ may have is preferably from 2 to 50, more preferably from 8 to 45, and still more preferably from 15 or 40.

The number of the carbon atoms of one or more substituents, among the substituents which $E_A$ or $Z_A$ may have, is preferably from 1 to 30, more preferably from 6 to 30, still more preferably from 8 to 30, and most preferably from 10 to 25.

Among the above-mentioned substituents, preferred are halogen atoms, and alkyl, alkenyl, aryl, heterocyclic, alkoxy, aryloxy, alkylthio, arylthio, cyano, acylamino, alkoxycarbonyl, carbamoyl, sulfamoyl, alkylamino and arylamino groups.

In the case that $E_A$ is an aryl group, $E_A$ preferably has an electron withdrawing substituent whose Hammett's substituent constant ($\sigma_p$) is more than 0, and more preferably has an electron withdrawing substituent whose $\sigma_p$ is from 0 to 1.5.

Hammett's substituent constants $\sigma_p$ and $\sigma_m$ are explained in detail, for example, in the following literatures: "Hammett Rule—Structure and Reactivity—", written by Naoki Inamoto (published by Maruzen), "New Experimental Chemical Course 14, Synthesis and Reaction V of Organic Compounds", p. 2605, edited by the Chemical Society of Japan (published by Maruzen), "Explanation on Theoretical Organic Chemistry", p. 217, written by Tadao Nakaya (published by Tokyo Kagaku Dojin), and "Chemical Review", Vol. 91, pp. 165–195 (1991).

$E_A$ is preferably an aryl or heterocyclic group having a substituent (preferably, any one of the above-mentioned preferred substitutes, more preferably halogen atoms, alkyl, aryl, heterocyclic and alkoxy groups, and particularly preferably halogen atoms, and alkyl and alkoxy groups) on at least one position adjacent to the carbon atom bonded to the oxazolidinedione ring. $E_A$ is more preferably an aryl or heterocyclic group having substituents (preferably, the above-mentioned preferred substitutes, more preferably a halogen atom, or an alkyl, aryl, heterocyclic or alkoxy group, and particularly preferably a halogen atom, or an alkyl or alkoxy group) at both positions adjacent to the carbon atom bonded to the oxazolidinedione ring. $E_A$ is particular preferably a heterocyclic group that may have the substituent(s) as above.

When $E_A$ is a heterocyclic group, compounds represented by the following formula (II) are preferred.

(II)

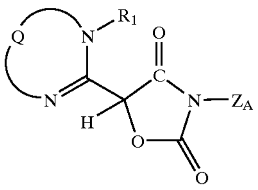

In the formula (II), $Z_A$ represents an aryl or heterocyclic ring, Q represents a group of atoms selected from carbon atoms and/or hetero atoms necessary to form, together with the N—C═N, a 5-, 6- or 7-membered ring; and $R_1$ represents a substituent. Examples of the substituent include the same as described as the examples of the substituent which $E_A$ or $Z_A$ may have.

When $E_A$ is a heterocyclic group, compounds in which Q is represented by the following formula (III) are more preferred.

(III)

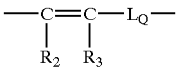

In the formula (III), $L_Q$ represents a carbonyl or sulfonyl group; $R_2$ and $R_3$, which may be the same or different, each represent a hydrogen atom or a substituent, or $R_2$ and $R_3$ may be bonded to each other to form a ring. Examples of the substituent include the same as described as the examples of the substituent which $E_A$ or $Z_A$ may have.

When $E_A$ is a heterocyclic group, $L_Q$ is most preferably a carbonyl group.

It is preferred that $Z_A$ is an aryl or heterocyclic group and said group has an electron withdrawing substituent whose Hammett's substituent constant ($\sigma_p$) value is more than 0. It is more preferred that said group has an electron withdrawing substituent whose $\sigma_p$ is from 0 to 1.5.

The sum total of the $\sigma_p$ values of the substituents which an aryl or heterocyclic group represented by $Z_A$ has is preferably 0 or more, more preferably 0.40 or more, still more preferably 0.60 or more, and most preferably 0.80 or more. The sum total of the $\sigma_p$ values is preferably 3.90 or less.

$Z_A$ is preferably a heterocyclic group or an aryl group that has at its ortho position a substituent (preferably, the above-mentioned preferred substituent, particularly preferably a halogen atom, an alkoxy or aryloxy group).

Among the compounds represented by formula (IA), compounds represented by the following formula (IV) are more preferred.

(IV)

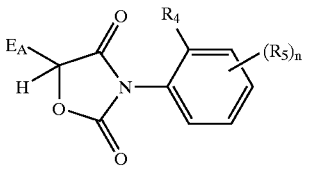

In the formula (IV), $E_A$ is an aryl or heterocyclic group; $R_4$ represents a halogen atom, an alkoxy group, or an aryloxy group; $R_5$ represents a substituent; n is an integer of 0, or 1 to 4; when n is an integer of 2 to 4, $R_5$'s may be the same or different; or the groups adjacent to each other, among $R_4$ and $R_5$('s), may be bonded to each other to form a ring.

$E_A$ has the same meaning as in the formula (IA), and the preferred scope thereof is also the same as about the formula (IA).

The halogen atom, the alkoxy group, and the aryloxy group, each of which is represented by $R_4$, have the same meanings as the halogen atom, the alkoxy group, and the aryloxy group, which are described as the substituent that the aryl group represented by $Z_A$ in the formula (IA) may have. The preferred scope thereof is also the same as about them. Examples of $R_5$ are the same as described as the examples of the substituent that the aryl group represented by $Z_A$ in the formula (IA) may have. The preferred scope thereof is also the same as about the substituent.

Preferred specific examples of the couplers represented by formula (IA) in the present invention are shown below. The present invention is not limited to these compounds. Tautomers wherein the hydrogen atom in the oxazolidinedione ring is transferred onto the carbonyl group or $E_A$ are also included in the present invention.

(1)

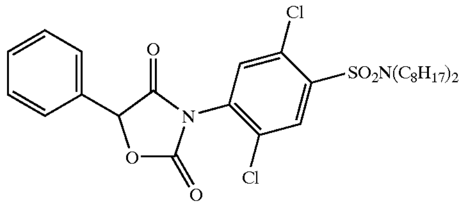

(2)

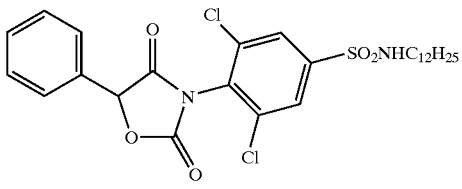

-continued
(3)
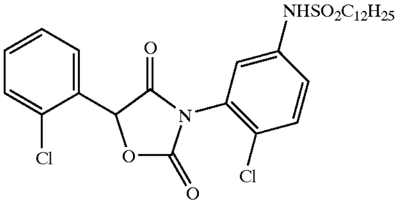
(4)
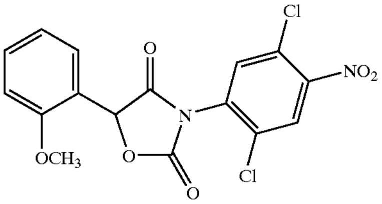
(5)
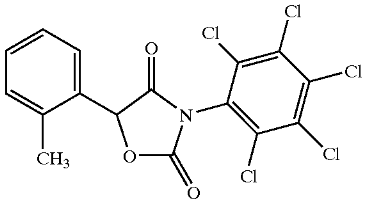
(6)
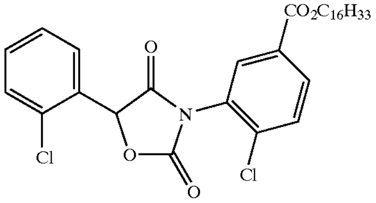
(7)
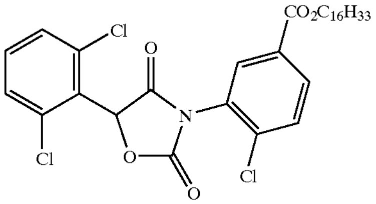
(8)
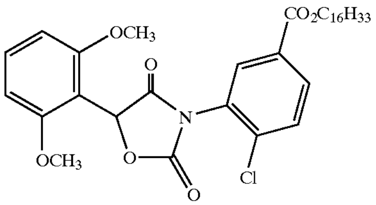
(9)
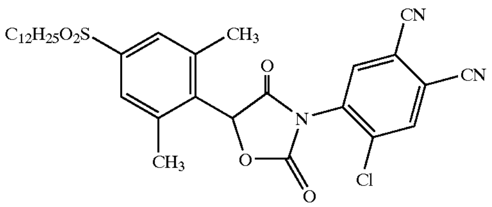
-continued
(10)
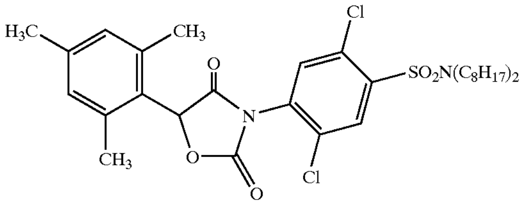
(11)
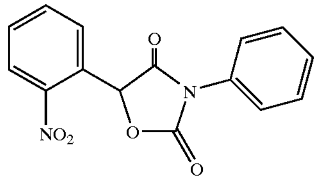
(12)
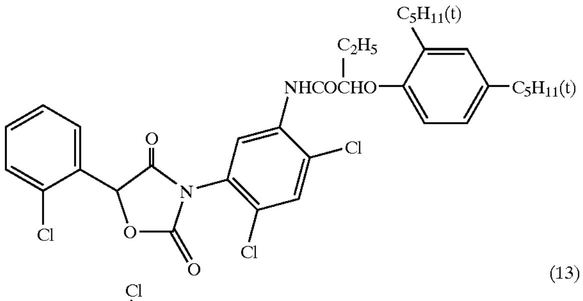
(13)
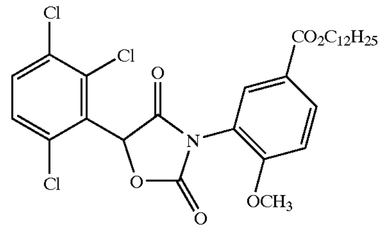
(14)
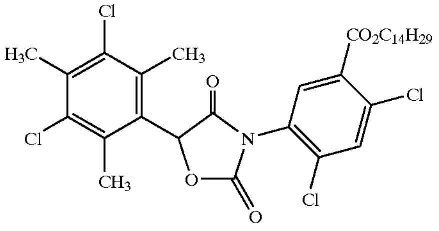
(15)
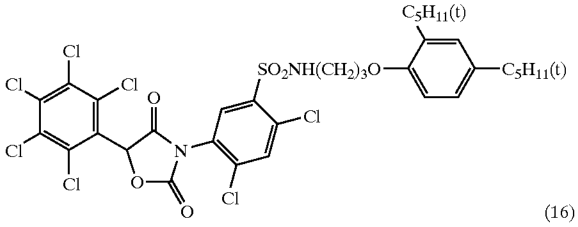
(16)
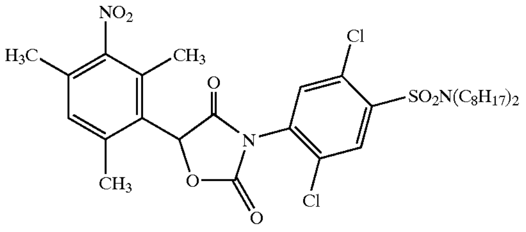

-continued
(17)
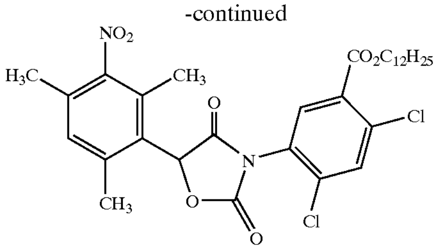
(18)
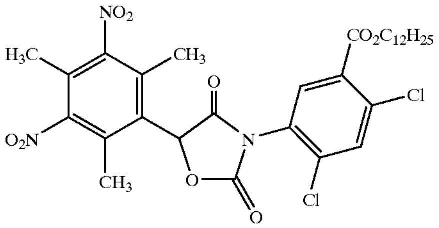
(19)
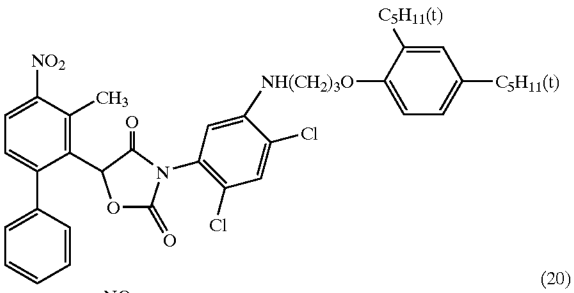
(20)
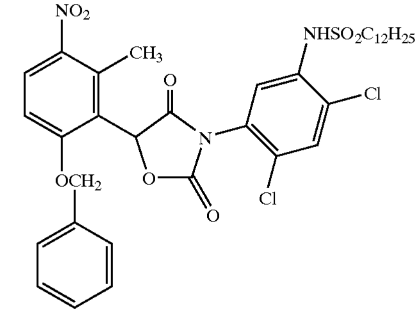
(21)
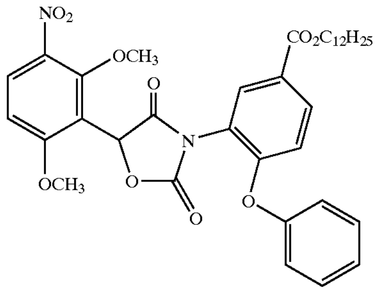
(22)
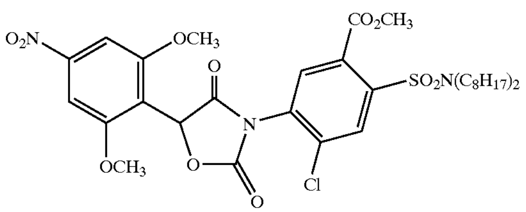
-continued
(23)
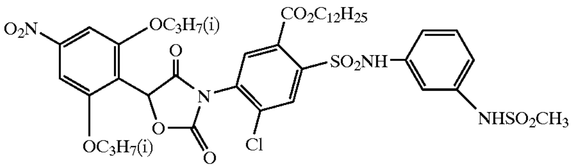
(24)
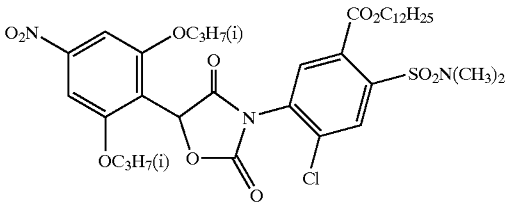
(25)
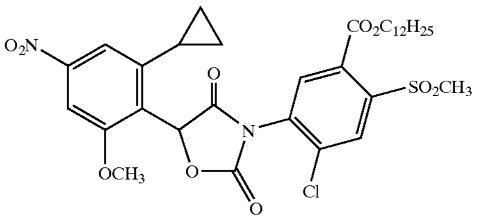
(26)
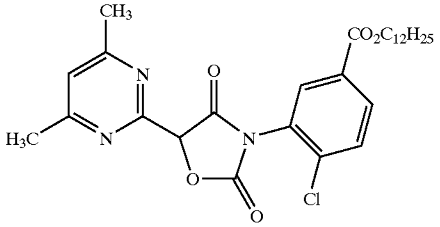
(27)
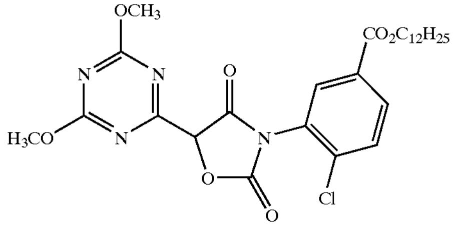
(28)
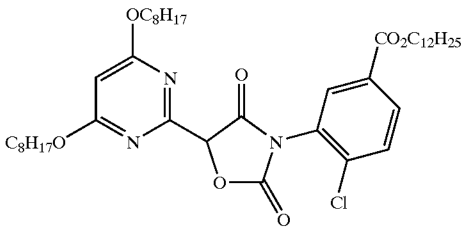
(29)
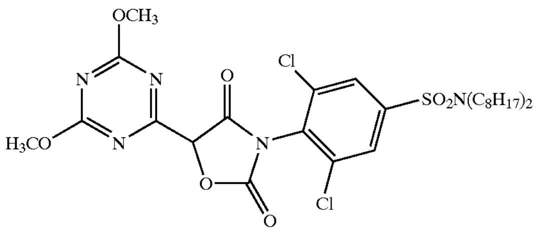

-continued
(30)
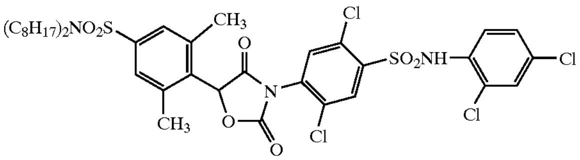
(31)
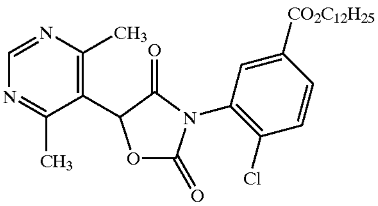
(32)
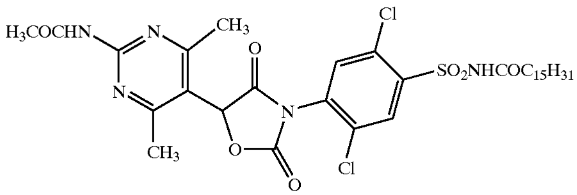
(33)
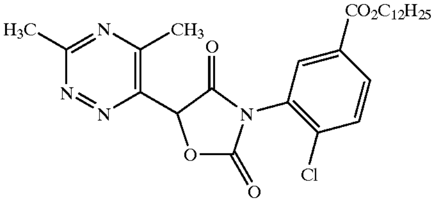
(34)
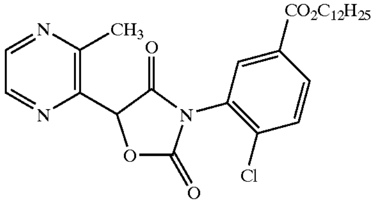
(35)
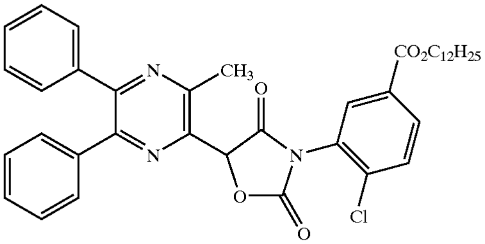
(36)
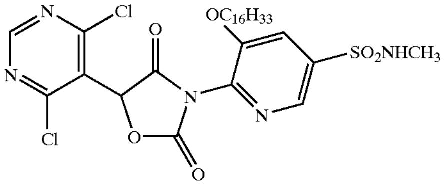
-continued
(37)
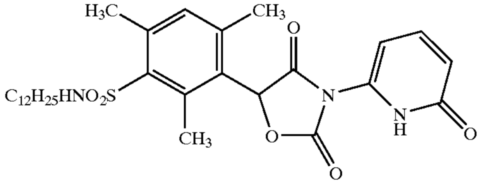
(38)
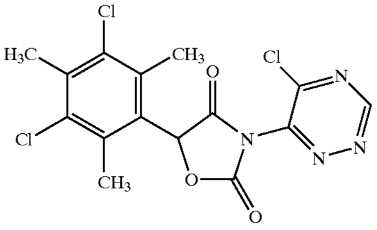
(39)
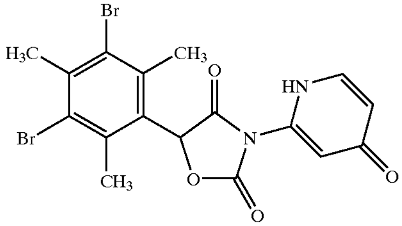
(40)
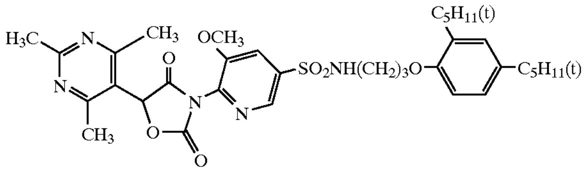
(41)
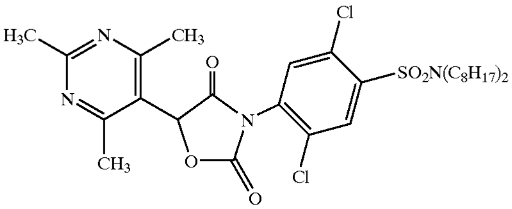
(42)
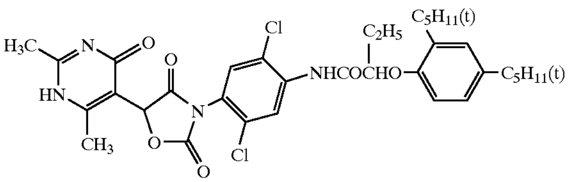
(43)
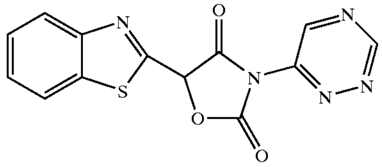

-continued
(44)
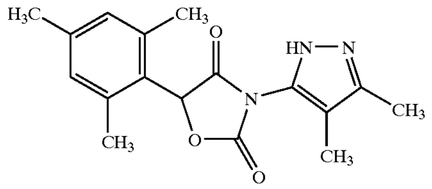
(45)
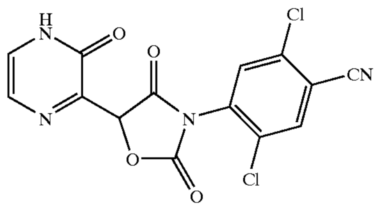
(46)
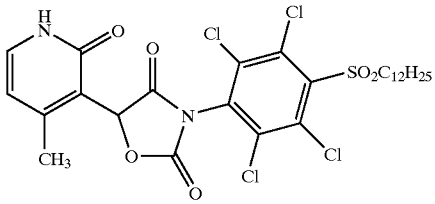
(47)
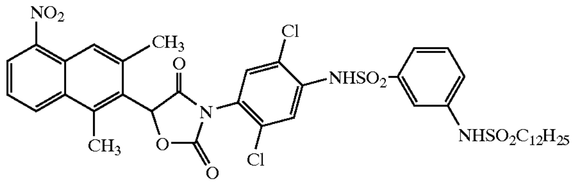
(48)
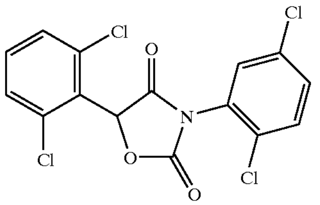
(49)
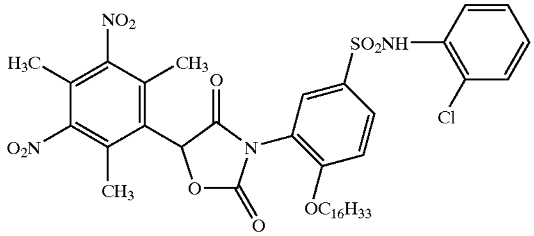
(50)
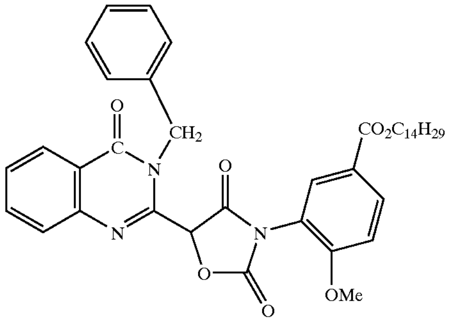
-continued
(51)
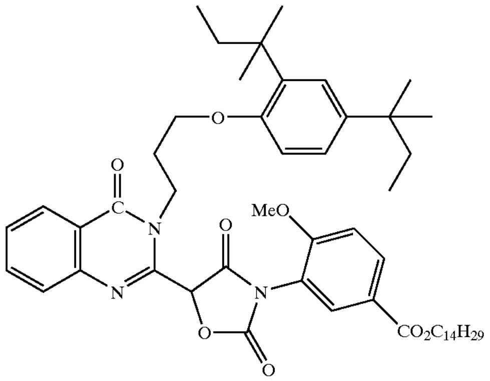
(52)
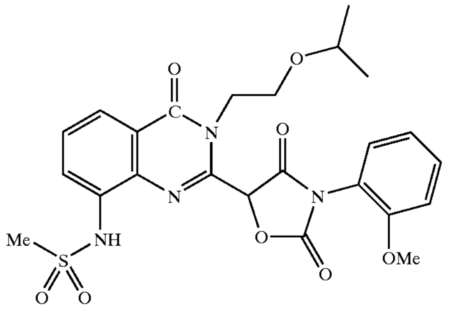
(53)
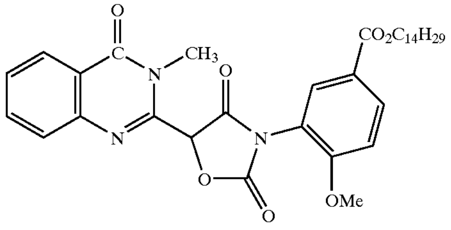
(54)
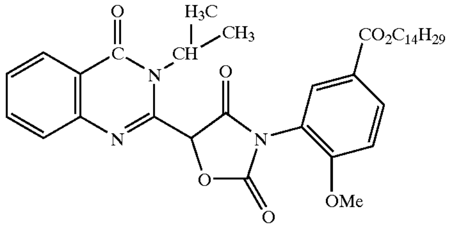
(55)
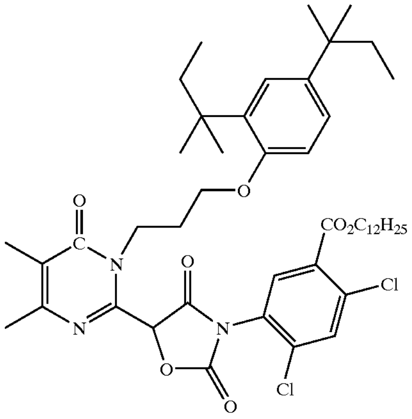

-continued
(56)
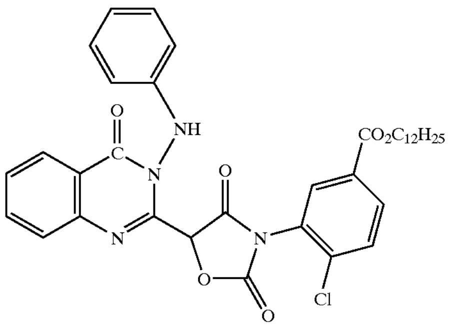
(57)
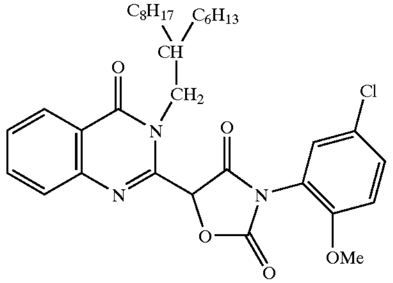
(58)
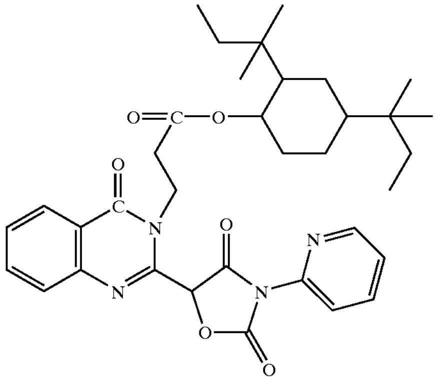
(59)
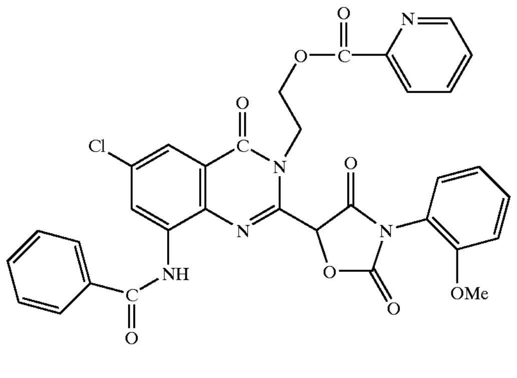
(60)
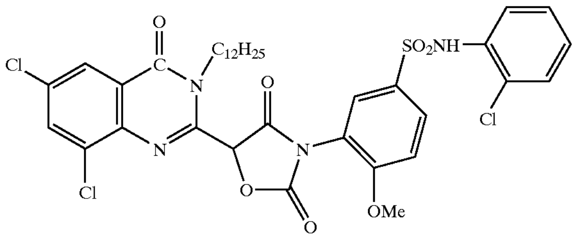
-continued
(61)
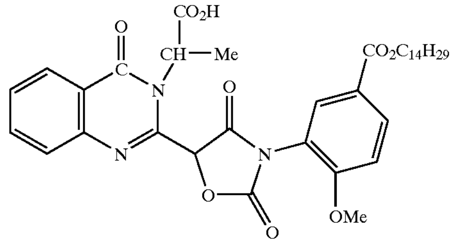
(62)
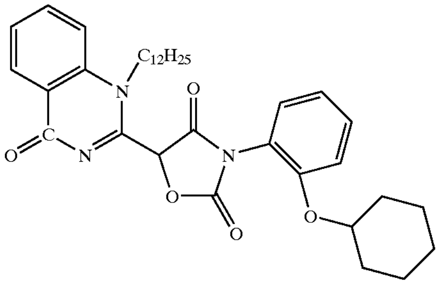
(63)
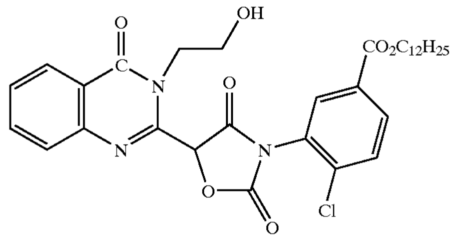
(64)
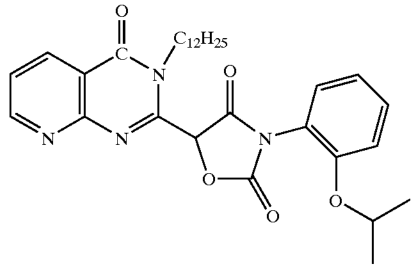
(65)
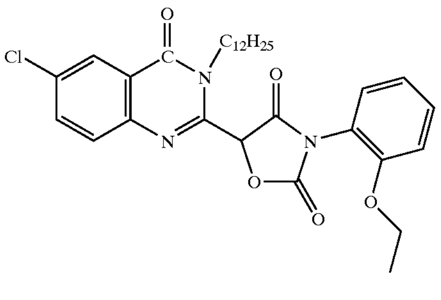
(66)
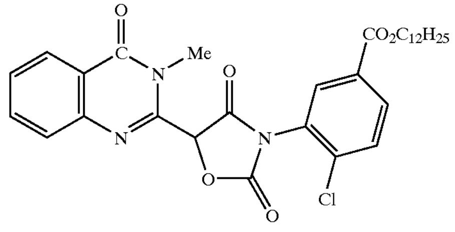

-continued
(67)
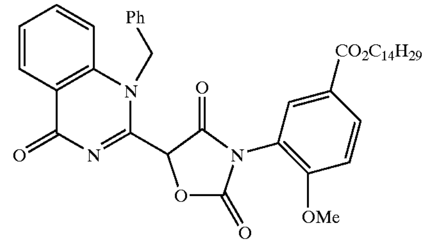
(68)
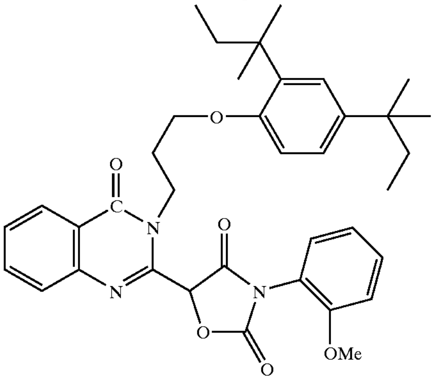
(69)
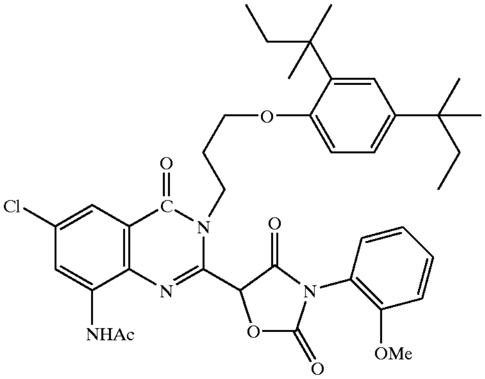
(70)
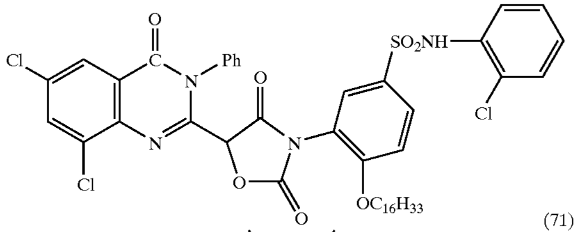
(71)
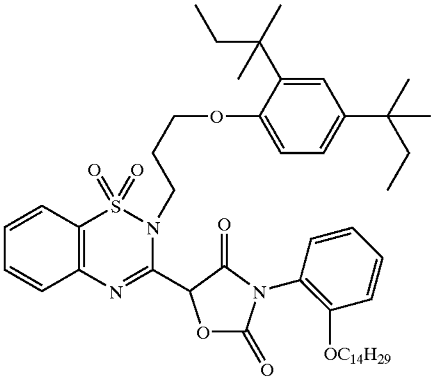
-continued
(72)
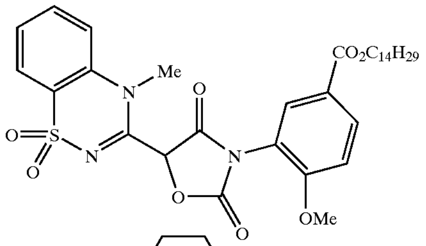
(73)
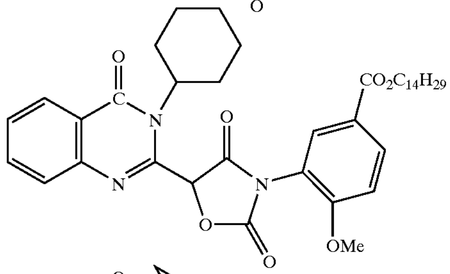
(74)
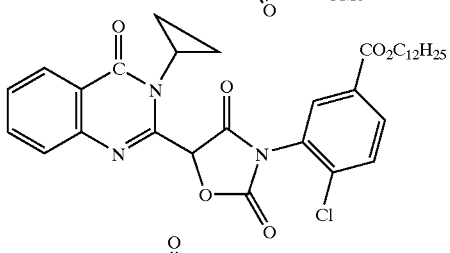
(75)
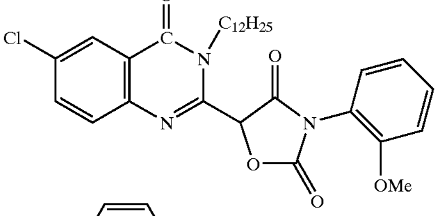
(76)
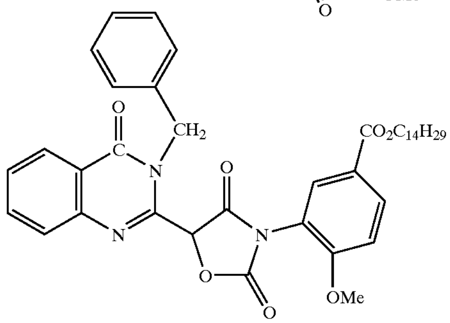
(77)
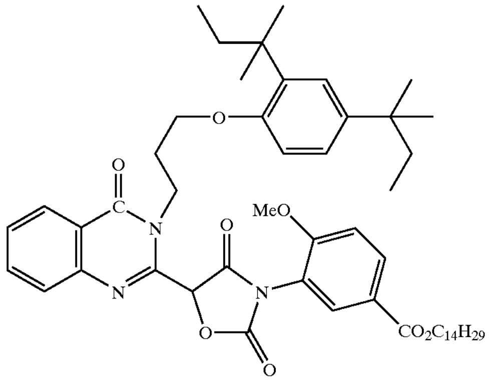

-continued (78)

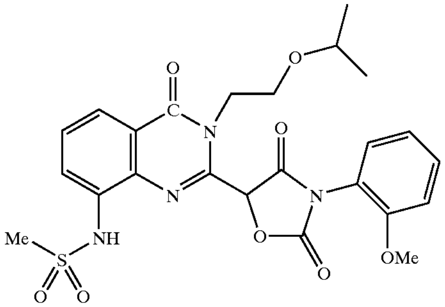

(79)

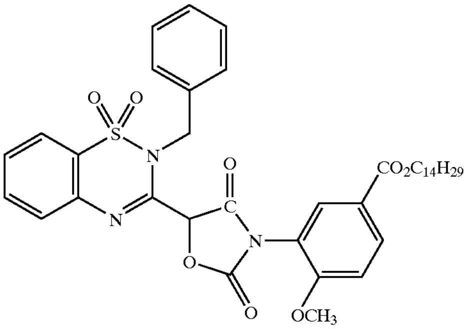

(80)

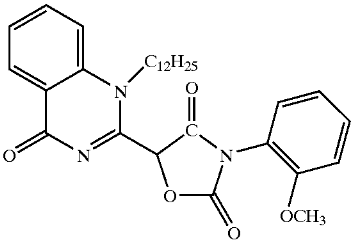

(81)

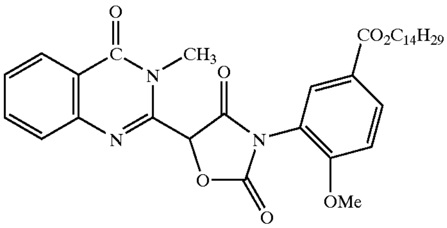

(82)

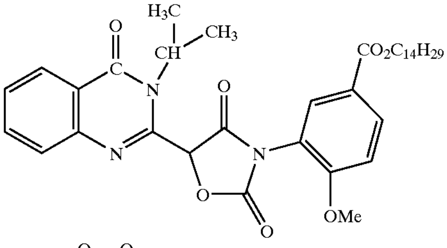

(83)

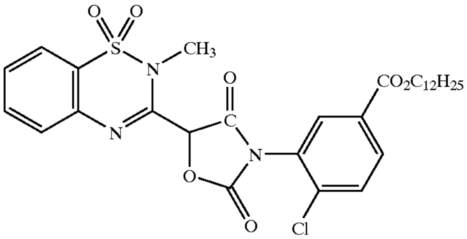

-continued (84)

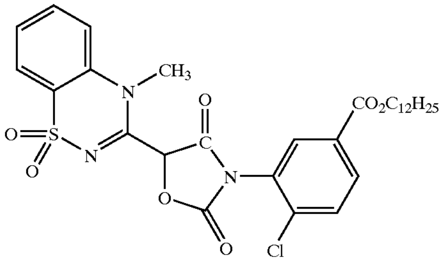

When any one of the exemplified compounds (which may also be referred to as dye-forming couplers) shown above is referred to in the following description, a number X put in parentheses, that is, (X) attached to the exemplified compound is used to express the compound as "the coupler (X)".

The following will describe specific synthetic examples of the compounds represented by formula (IA).

Synthetic Example 1

Synthesis of the Coupler (48)

The coupler (48) was synthesized according to the following route:

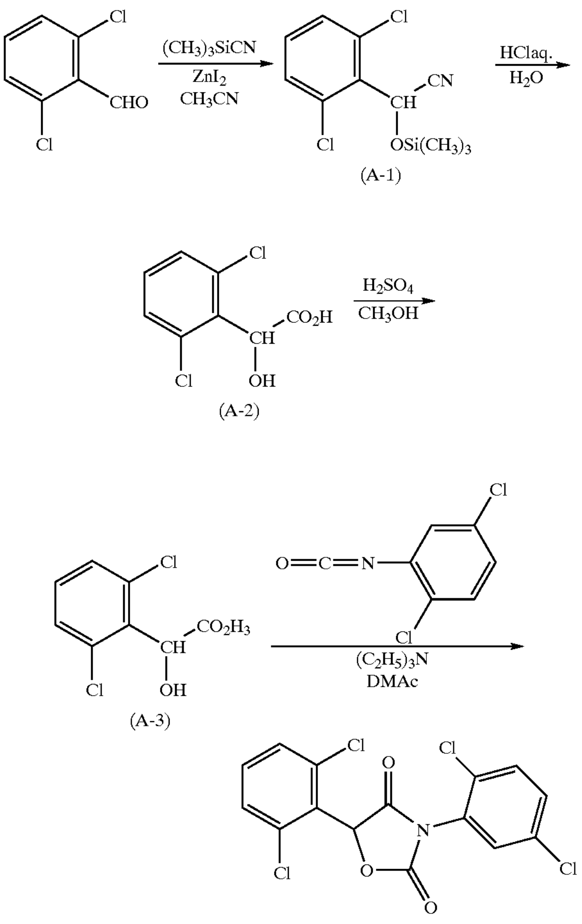

Coupler (48)

To 50 ml of a solution of 0.73 g of zinc iodide and 11.9 g of 2,6-dichlorobenzaldehyde in acetonitrile, was dropwise added 7.4 g of trimethylsilylcyanide at 0° C. under the atmosphere of nitrogen. The temperature of the resultant system was returned to room temperature and the solution was stirred for 2 hours. Thereafter, the solution was poured into ice water, and ethyl acetate was added thereto, to perform extraction. The organic phase was washed with saturated brine. The organic phase was dried over anhydrous magnesium sulfate and then the solvent was distilled off under reduced pressure, to give a compound (A-1) as a liquid. Thereto was added 10 ml of water, and then 150 ml of 35% aqueous hydrochloric acid was added thereto. The resultant solution was stirred for 2 hours while refluxed under heating. The temperature of the system was lowered to 0° C., and then the solution was made to weak alkalinity with 2% aqueous potassium hydroxide solution. Ethyl acetate was added to the resultant solution, to separate the solution into two liquid phases. The aqueous phase was made to weak acidic with 1N aqueous hydrochloric acid. This aqueous phase was extracted with ethyl acetate and the organic phase was dried over anhydrous magnesium sulfate. Thereafter, the solvent was distilled off under reduced pressure, to give 12.4 g of a compound (A-2).

Into 70 ml of methyl alcohol was dissolved 10 g of the compound (A-2), and then 4 or 5 drops of concentrated sulfuric acid were added thereto. This solution was stirred for 2 hours while refluxed under heating. The solution was cooled, and then 10% aqueous potassium carbonate solution and ethyl acetate were added thereto, to perform extraction. The organic phase was washed with saturated brine. The organic phase was dried over anhydrous magnesium sulfate, and then the solvent was distilled off under reduced pressure, to give 9.1 g of a compound (A-3).

A 80 ml solution of 9 g of the compound (A-3), 7.2 g of 2,5-dichlorophenylisocyanate, and 3.9 g of triethylamine in N,N-diemethylacetoamide was heated to 110° C. and stirred for 3 hours. The system was cooled and then water and ethyl acetate were added thereto, to perform extraction. The organic phase was washed with saturated brine. The organic phase was dried over anhydrous magnesium sulfate, and then the solvent was distilled off under reduced pressure. The resultant residue was subjected to crystallization from a mixed solvent of ethyl acetate and hexane, to give 8.2 g of the coupler (48).

Synthetic Example 2

Synthesis of the Coupler (11)

The coupler (11) was synthesized according to the following route:

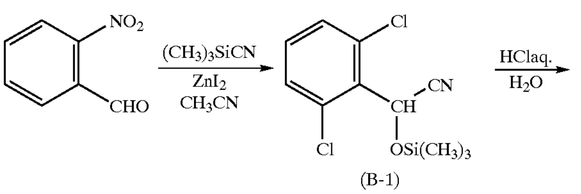

(B-1)

-continued

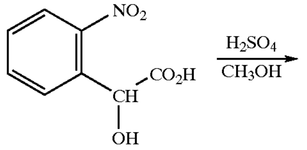

(B-2)

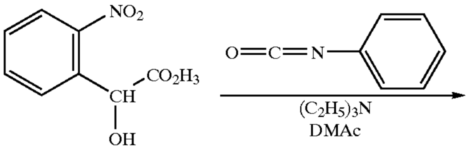

(B-3)

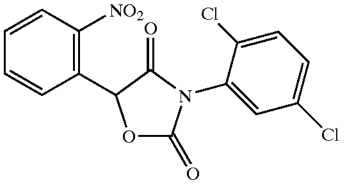

Coupler (11)

To 50 ml of a solution of 0.96 g of zinc iodide and 15.1 g of 2-nitrobenzaldehyde in acetonitrile, was dropwise added 10.9 g of trimethylsilylcyanide at 0° C. under the atmosphere of nitrogen. The temperature of the system was returned to room temperature and the resultant solution was stirred for 2 hours. Thereafter, the solution was poured into ice water, and ethyl acetate was added thereto, to perform extraction. The organic phase was washed with saturated brine. The organic phase was dried over anhydrous magnesium sulfate and then the solvent was distilled off under reduced pressure, to give a compound (B-1) as a liquid. Thereto was added 10 ml of water, and then 200 ml of 35% aqueous hydrochloric acid was added thereto. The solution was stirred for 5 hours while refluxed under heating. The temperature of the system was lowered to 0° C., and then the solution was made to weak alkalinity with 2% aqueous potassium hydroxide solution. Ethyl acetate was added to the solution, to separate the solution into two liquid phases. The aqueous phase was made to weak acidic with 1N aqueous hydrochloric acid. This aqueous phase was extracted with ethyl acetate and the resultant organic phase was dried over anhydrous magnesium sulfate. Thereafter, the solvent was distilled off under reduced pressure, to give 8.4 g of a compound (B-2).

Into 50 ml of methyl alcohol was dissolved 7.5 g of the resultant compound (B-2), and then 4 or 5 drops of concentrated sulfuric acid were added thereto. This solution was stirred for 1.5 hour while refluxed under heating. The solution was cooled, and then 10% aqueous potassium carbonate solution and ethyl acetate were added thereto, to perform extraction. The organic phase was washed with saturated brine. The organic phase was dried over anhydrous magnesium sulfate, and then the solvent was distilled off under reduced pressure, to give 8 g of a compound (B-3).

A 50 ml solution of 8 g of the compound (B-3), 4.8 g of phenylisocyanate, and 3.9 g of triethylamine in N,N-dimethylacetoamide was heated to 110° C. and stirred for 4 hours. The temperature of the system was lowered and then water and ethyl acetate were added thereto, to perform extraction. The organic phase was washed with saturated brine. The organic phase was dried over anhydrous magnesium sulfate, and then the solvent was distilled off under reduced pressure. The resultant residue was subjected to crystallization from a mixed solvent of ethyl acetate and hexane, to give 5.1 g of the coupler (11).

Synthetic Example 3

Synthesis of the Coupler (10)

The coupler (10) was synthesized according to the following route:

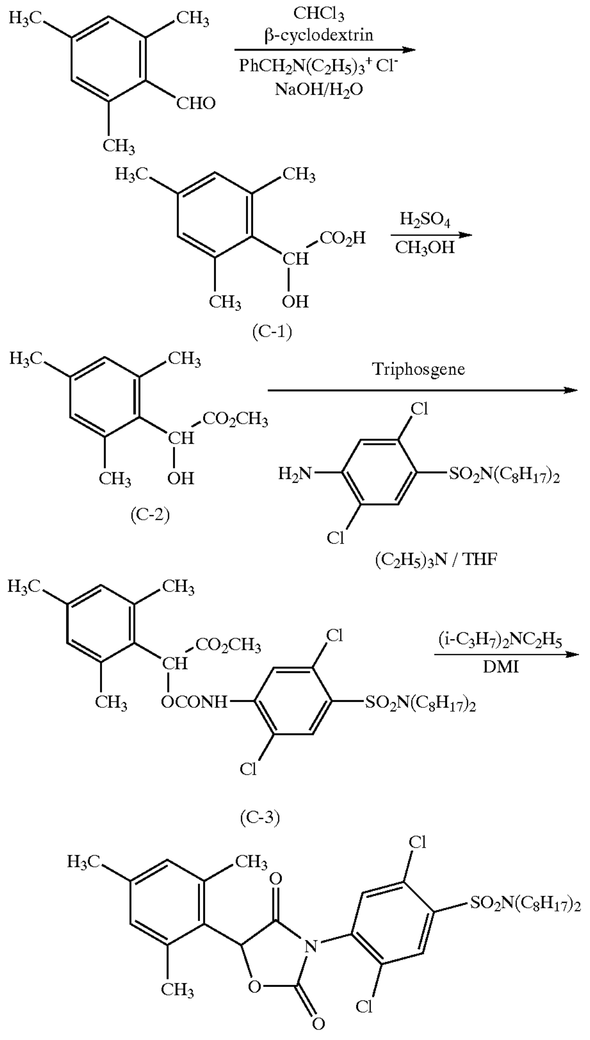

(C-1)

(C-2)

(C-3)

Coupler (10)

The following were mixed: 74.1 g of mesithylene, 11.4 g of β-cyclodextrin, 5.7 g of benzyltriethylammonium chloride, and 100 g of chloroform. The resultant mixture was stirred at 50° C. for 20 minutes. Thereto were dropwise added a solution of 100 g of sodium hydroxide in 100 ml of water, at an internal temperature of 50 to 60° C., under cooling with water, over 30 minutes. The resultant solution was stirred at 50° C. for 4 hours, and it was then refluxed under heating for 5 hours. Ethyl acetate and water were added thereto, to separate the solution into two liquid phases. The aqueous phase was made to acidity with aqueous hydrochloric acid. This aqueous phase was extracted with ethyl acetate and the resultant organic phase was dried over anhydrous magnesium sulfate. Thereafter, the solvent was distilled off under reduced pressure and the resultant residue was subjected to crystallization from a mixed solvent of ethyl acetate and hexane, to give 36.2 g of a compound (C-1).

Then, 15.5 g of the compound (C-1) and 1.5 ml of concentrated sulfuric acid were dissolved into 150 ml of methanol, and then the resultant solution was refluxed under heating for 6 hours. Ethyl acetate and water were added thereto, to perform extraction, and then the organic phase was washed with aqueous sodium bicarbonate and saturated brine. The resultant solution was dried over anhydrous magnesium sulfate, and the solvent was distilled off under reduced pressure. The residue was then subjected to crystallization from a mixed solvent of ethyl acetate and hexane, to give 14.6 g of a compound (C-2).

Into 230 ml of tetrahydrofuran (THF) was dissolved 5.4 g of triphosgene. Under cooling with water, 10.7 g of 2,5-dichloro-4-dioctylsulfamoylaniline was added thereto. The resultant solution was stirred at 10 to 12° C. for 1 hour. To this solution were dropwise added a mixed solution of 12.9 ml of triethylamine and 150 ml of THF under cooling with ice over 25 minutes. The resultant solution was stirred under cooling with ice for 15 minutes. Thereafter, 8.4 g of the compound (C-2) was added thereto under cooling with ice. Furthermore, a mixed solution of 6.5 ml of triethylamine and 30 ml of THF was dropwise added thereto over 5 minutes. The resultant solution was stirred at room temperature for 1 hour. Ethyl acetate and water were added thereto, to perform extraction, and then the organic phase was washed with aqueous dilute hydrochloric acid and saturated brine. The resultant solution was dried over anhydrous magnesium sulfate, and the solvent was distilled off under reduced pressure. The residue was then subjected to crystallization from a mixed solvent of ethyl acetate and hexane, to give 14.4 g of a compound (C-3).

Into 250 ml of 1,3-dimethyl-2-imidazolidinone was dissolved 12.6 g of the compound (C-3). Thereto was added 4.6 ml of diisopropylethylamine. The solution was stirred at 120° C. for 3.5 hours. Ethyl acetate and water were added thereto, to perform extraction, and then the organic phase was washed with aqueous dilute hydrochloric acid and saturated brine. The solution was dried over anhydrous magnesium sulfate, and the solvent was distilled off under reduced pressure. The residue was purified with column chromatography. The resultant crude product was then subjected to crystallization from a mixed solvent of ethyl acetate and hexane, to give 3.4 g of the coupler (10).

Synthetic Example 4

Synthesis of the Coupler (16)

The coupler (16) was synthesized according to the following route:

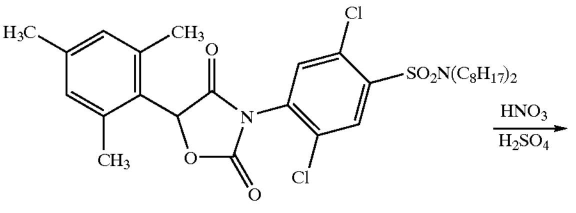

Coupler (10)

-continued

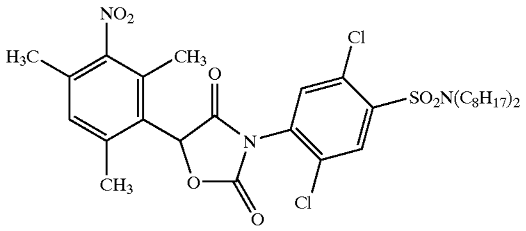

Coupler (16)

To 10 ml of concentrated sulfuric acid was dropwise added 10 ml of concentrated nitric acid (specific gravity: 1.38) under cooling with ice, and then the resultant mixture of acids was stirred for 10 minutes. To this solution, was dropwise added a solution of 1.1 g of the coupler (10) dissolved in 5 ml of methylene chloride, over 5 minutes, under cooling with ice. Thereafter, the resultant solution was stirred at room temperature for 1 hour. The reaction mixture was poured into ice water, and the solution was extracted with ethyl acetate. The organic phase was washed with aqueous sodium bicarbonate and saturated brine, and dried over anhydrous magnesium sulfate. The solvent was then distilled off under reduced pressure. The residue was purified by column chromatography and was then subjected to crystallization from a mixed solvent of ethyl acetate and hexane, to give 0.7 g of the coupler (16).

Synthetic Example 5

Synthesis of the Coupler (53)

The coupler (53) was synthesized according to the following route:

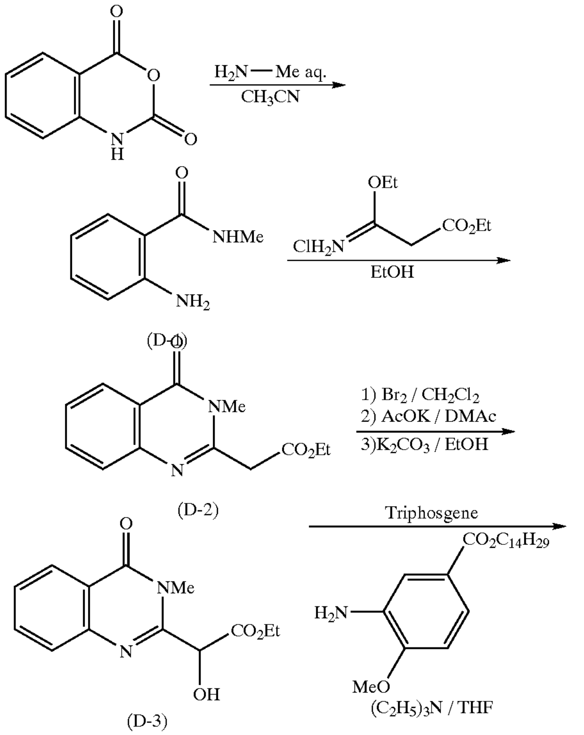

(D-1)

(D-2)

(D-3)

-continued

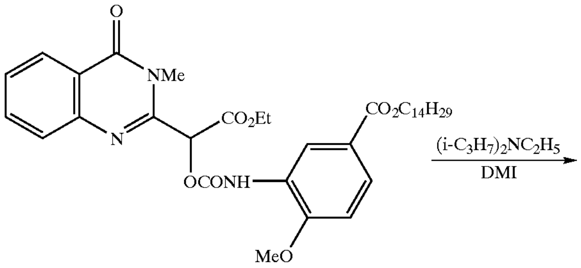

(D-4)

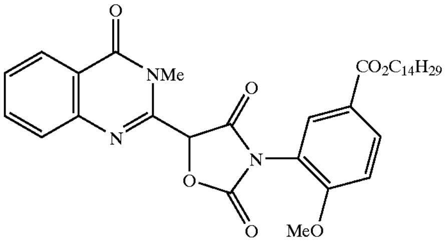

Coupler (53)

To 1 liter of a solution of 163 g of isatoic anhydride in acetonitrile, was dropwise added 232.5 g of a 40% aqueous solution of methylamine. The resultant solution was stirred at room temperature for 1 hour. Ethyl acetate and water were added thereto, to separate the solution into two liquid phases. The organic phase was dried over anhydrous magnesium sulfate. Thereafter, the solvent was distilled off under reduced pressure and the residue was subjected to crystallization from a mixed solvent of ethyl acetate and hexane, to give 102.3 g of a compound (D-1).

102.3 g of the compound (D-1) and 1 liter of a solution of 333 g of hydrochloride of iminoether in ethyl alcohol were stirred for 1 hour while refluxed under heating. After the solution was cooled, water was poured into the solution, to precipitate 160 g of crystal of a compound (D-2).

To a 1 liter solution of 73.8 g of the compound (D-2) in methylene chloride was dropwise added a 200 ml solution of 47.9 g of bromine in methylene chloride under cooling with ice. The solution was stirred at room temperature for 10 minutes, and then water was added thereto, to separate the solution into two liquid phases. The organic phase was dried over anhydrous magnesium sulfate, and then the solvent was distilled off under reduced pressure. Thereto was added 500 ml of N,N-dimethylacetoamide. The resultant solution was dropwise added a 1 liter solution of 88.3 g of potassium acetate in N,N-dimethylacetoamide. The solution was stirred at room temperature over night. Ethyl acetate and water were added thereto, to separate the solution into two liquid phases. The organic phase was dried over anhydrous magnesium sulfate. Thereafter, the solvent was distilled off under reduced pressure. Thereto were added 800 ml of ethyl alcohol and 82.9 g of potassium carbonate. The resultant solution was stirred at room temperature for 3 hours. Ethyl acetate and water were added thereto, to separate the solution into two liquid phases. The separated aqueous phase was extracted with ethyl acetate, and the resultant organic phase was dried over anhydrous magnesium sulfate. The dried organic phase was purified by column chromatography, and the resultant crude product was subjected to crystallization from a mixed solvent of ethyl acetate and hexane, to give 57 g of a compound (D-3).

Into 500 ml of THF was dissolved 13.1 g of triphosgene. Under cooling with water, 40 g of 2-alkoxymethyl-5-tetradecanolcarbonylaniline was added thereto. The resultant solution was stirred at 10 to 12° C. for 1 hour. To this solution was dropwise added a mixed solution of 30.7 ml of triethylamine and 200 ml of THF over 30 minutes under cooling with ice. The resultant solution was stirred for 1 hour under cooling with ice. Thereafter, the temperature of the system was returned to room temperature. The solution was further stirred for 1 hour, and then 26.2 g of the compound (D-3) was added thereto under cooling with ice. To this solution was dropwise added a mixed solution of 30.7 ml of triethylamine and 50 ml of THF over 5 minutes. The solution was stirred at room temperature for 1 hour. Ethyl acetate and water were added thereto, to perform extraction, and then the organic phase was washed with aqueous dilute hydrochloric acid and saturated brine. The resultant solution was dried over anhydrous magnesium sulfate, and the solvent was distilled off under reduced pressure. The residue was then subjected to crystallization from a mixed solvent of ethyl acetate and hexane, to give 52.8 g of a compound (D-4).

Into 200 ml of 1,3-dimethyl-2-imidazolidinone was dissolved 22.8 g of the compound (D-4). Thereto was added 6.7 ml of diisopropylethylamine. The resultant solution was stirred at 150° C. for 10 minutes. Ethyl acetate and water were added thereto, to perform extraction, and then the organic phase was washed with aqueous dilute hydrochloric acid and saturated brine. The solution was dried over anhydrous magnesium sulfate, and the solvent was distilled off under reduced pressure. The residue was purified by column chromatography. The resultant crude product was then subjected to crystallization from a solvent, acetonitrile, to give 12 g of the coupler (53).

Synthetic Example 6

Synthesis of the Coupler (50)

The coupler (50) was synthesized according to the following route:

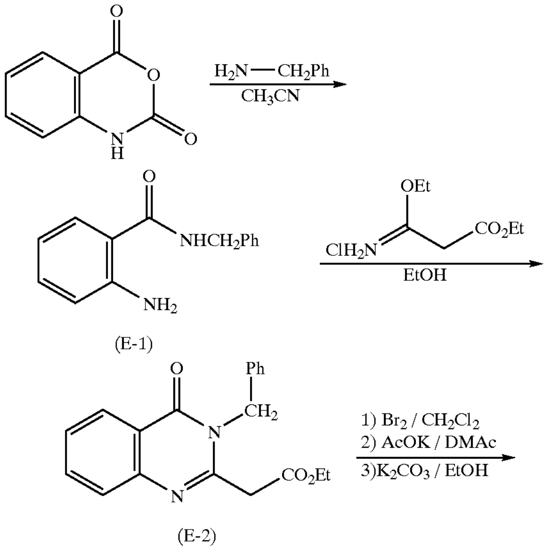

-continued

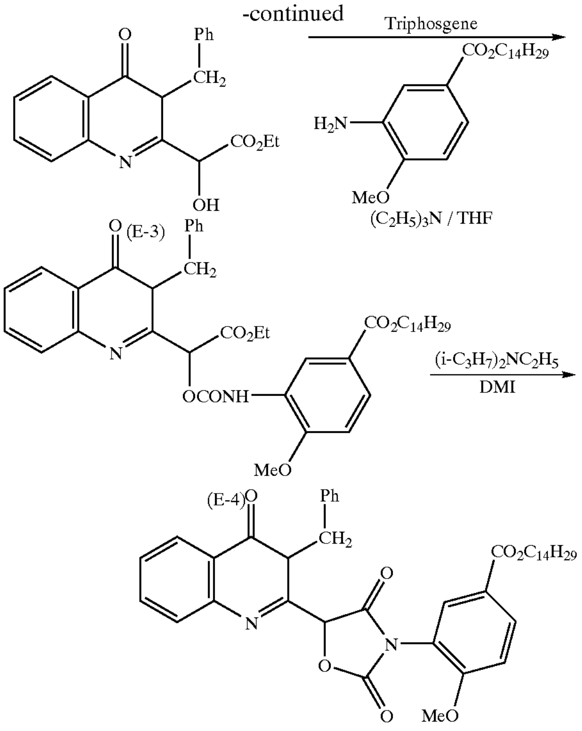

Coupler (50)

To a 200 ml solution of 48.9 g of isatoic anhydride in acetonitrile was dropwise added 32.2 g of benzylamine. The resultant solution was stirred. The temperature of the system was raised to 60° C., and the resultant solution was further stirred for 10 minutes. Ethyl acetate and water were added thereto, to separate the solution into two liquid phases. The organic phase was dried over anhydrous magnesium sulfate. Thereafter, the solvent was distilled off under reduced pressure, and the residue was subjected to crystallization from a mixed solvent of ether and hexane, to give 54.6 g of a compound (E-1).

24.9 g of the compound (E-1), 21.6 g of hydrochloride of iminoether, and a 200 ml solution of 10.5 g of p-toluenesulfonic acid monohydrate in ethyl alcohol were stirred for 3 hours while refluxed under heating. After the solution was cooled, 21.6 g of hydrochloride of iminoether was added thereto. The solution was further stirred for 1 hour while refluxed under heating. Ethyl acetate and water were added thereto, to separate the solution into two liquid phases. The organic phase was dried over anhydrous magnesium sulfate. Thereafter, the solvent was distilled off under reduced pressure, and then the residue was subjected to crystallization from a mixed solvent of ether and hexane, to give 33.6 g of a compound (E-2).

To a 300 ml solution of 32.2 g of the compound (E-2) in methylene chloride was dropwise added a 25 ml solution of 15.8 g of bromine in methylene chloride under cooling with ice. The solution was stirred at room temperature for 10 minutes, and then water was added thereto, to separate the solution into two liquid phases. The organic phase was dried over anhydrous magnesium sulfate, and then the solvent was distilled off under reduced pressure. Thereto was added 80 ml of N,N-dimethylacetoamide. The resultant solution was dropwise added to a 300-ml solution of 29.4 g of potassium acetate in N,N-dimethylacetoamide. The solution was stirred at room temperature over night. Ethyl acetate and water were added thereto, to separate the solution into two liquid phases. The organic phase was dried over anhydrous magnesium sulfate. Thereafter, the solvent was distilled off under reduced pressure. Thereto were added 400 ml of ethyl alcohol and 24.4 g of potassium carbonate. The solution was stirred at room temperature for 3 hours. Ethyl acetate and water were added thereto, to separate the solution into two liquid phases. The aqueous phase was extracted with ethyl acetate, and the resultant organic phase was dried over anhydrous magnesium sulfate. The dried organic phase was subjected to crystallization from a mixed solvent of ethyl acetate and hexane, to give 24 g of a compound (E-3).

Into 100 ml of THF was dissolved 2.6 g of triphosgene. Under cooling with water, 8.0 g of 2-alkoxymethyl-5-tetradecanolcarbonylaniline was added thereto. The solution was stirred at 10 to 12° C. for 1 hour. To this solution was dropwise added a mixed solution of 6.1 ml of triethylamine and 50 ml of THF over 10 minutes under cooling with ice. The solution was stirred for 1 hour under cooling with ice. The temperature of the solution was returned to room temperature and further stirred for 1 hour. Thereafter, 6.7 g of the compound (E-3) was added thereto under cooling with ice. Furthermore, a mixed solution of 6.1 ml of triethylamine and 12 ml of THF was dropwise added thereto. The solution was stirred at room temperature for 2 hours. Thereafter, ethyl acetate and water were added thereto, to perform extraction, and then the organic phase was washed with aqueous dilute hydrochloric acid and saturated brine. The resultant solution was dried over anhydrous magnesium sulfate, and the solvent was distilled off under reduced pressure. The residue was purified by column chromatography. The resultant crude product was then subjected to crystallization from a mixed solvent of ethyl acetate and hexane, to give 13.1 g of a compound (E-4).

Into 130 ml of 1,3-dimethyl-2-imidazolidinone was dissolved 13.1 g of the compound (E-4). Thereto was added 3.7 ml of diisopropylethylamine. The resultant solution was stirred at 150° C. for 30 minutes. Ethyl acetate and water were added thereto, to perform extraction, and then the organic phase was washed with aqueous dilute hydrochloric acid and saturated brine. The resultant solution was dried over anhydrous magnesium sulfate, and the solvent was distilled off under reduced pressure. The residue was purified by column chromatography. The resultant crude product was then subjected to crystallization from a solvent, acetonitrile, to give 5.5 g of the coupler (50).

Synthetic Example 7

Synthesis of the Coupler (51)

The coupler (51) was synthesized according to the following route:

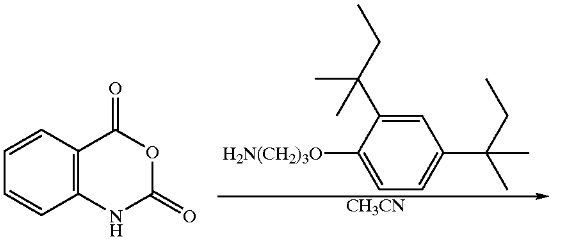

-continued

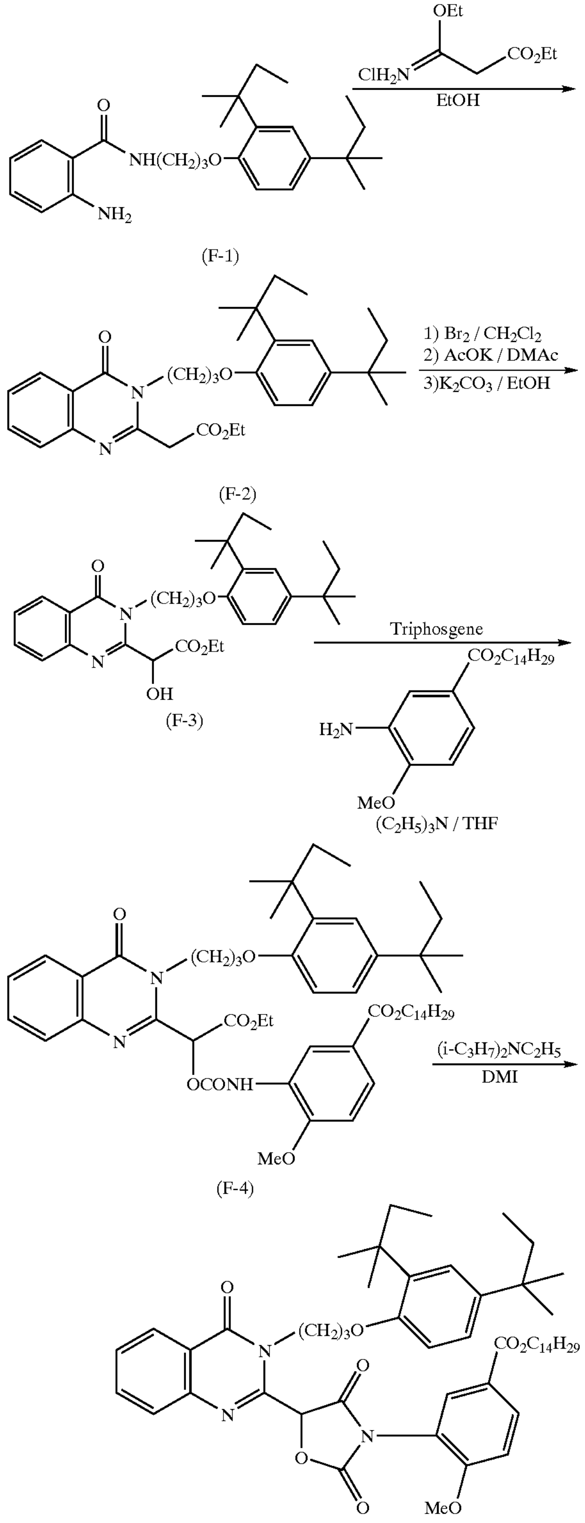

(F-1)
(F-2)
(F-3)
(F-4)
Coupler (51)

To a 200 ml solution of 34.3 g of isatoic anhydride in acetonitrile was added 58.3 g of 3-(2,4-di-t-amyl-phenoxy)-propylamine. The resultant solution was stirred. The temperature of the system was raised to 40° C. The solution was further stirred for 15 minutes. Ethyl acetate and water were added thereto, to separate the solution into two liquid phases. The organic phase was dried over anhydrous magnesium sulfate. Thereafter, the solvent was distilled off under reduced pressure, to give 81.3 g of a compound (F-1).

41.1 g of the compound (F-1) and a 200-ml solution of 39.1 g of hydrochloride of iminoether in ethyl alcohol were stirred at 30° C. for 1 hour. Thereto was added 8.6 g of p-toluenesulfonic acid monohydrate, and then the solution was stirred for 2 hours while refluxed under heating. Ethyl acetate and water were added thereto, to separate the solution into two liquid phases. The organic phase was dried over anhydrous magnesium sulfate. Thereafter, the solvent was distilled off under reduced pressure, and then the residue was subjected to crystallization from a solvent, methyl alcohol, to give 31.8 g of a compound (F-2).

To a 300 ml solution of 25.3 g of the compound (F-2) in methylene chloride was dropwise added a 20 ml solution of 7.9 g of bromine in methylene chloride under cooling with ice. After stirring the resultant solution at room temperature for 15 min, water was added thereto, to separate the solution into two liquid phases. The organic phase was dried over anhydrous magnesium sulfate, and then the solvent was distilled off under reduced pressure. Thereto was added 50 ml of N,N-dimethylacetoamide. The resultant solution was dropwise added to a 200-ml solution of 14.7 g of potassium acetate in N,N-dimethylacetoamide. The solution was stirred at room temperature over night. Ethyl acetate and water were added thereto, to separate the solution into two liquid phases. The organic phase was dried over anhydrous magnesium sulfate. Thereafter, the solvent was distilled off under reduced pressure. Thereto were added 300 ml of ethyl alcohol and 12.2 g of potassium carbonate. The solution was stirred at room temperature for 3 hours. Ethyl acetate and water were added thereto, to separate the solution into two liquid phases. The aqueous phase was extracted with ethyl acetate, and the resultant organic phase was dried over anhydrous magnesium sulfate. The dried organic phase was subjected to crystallization from a mixed solvent of ethyl acetate and hexane, to give 18 g of a compound (F-3).

Into 100 ml of THF was dissolved 2.6 g of triphosgene. Under cooling with water, 8.0 g of 2-alkoxymethyl-5-tetradecanolcarbonylaniline was added thereto. The solution was stirred at 10 to 12° C. for 1 hour. To this solution was dropwise added a mixed solution of 6.1 ml of triethylamine and 50 ml of THF over 10 minutes under cooling with ice. The solution was stirred for 1 hour under cooling with ice. The temperature of the solution was returned to room temperature, and it was further stirred for 1 hour. Thereafter, 10.5 g of the compound (F-3) was added thereto under cooling with ice. Furthermore, a mixed solution of 6.1 ml of triethylamine and 12 ml of THF was dropwise added thereto. The solution was stirred at room temperature for 2 hours. Thereafter, ethyl acetate and water were added thereto, to perform extraction, and then the organic phase was washed with aqueous dilute hydrochloric acid and saturated brine. The resultant solution was dried over anhydrous magnesium sulfate, and the solvent was distilled off under reduced pressure. The residue was purified by column chromatography. The resultant crude product was then subjected to crystallization from a mixed solvent of ethyl acetate and hexane, to give 15.5 g of a compound (F-4).

Into 150 ml of 1,3-dimethyl-2-imidazolidinone was dissolved 15.5 g of the compound (F-4). Thereto was added 3.6 ml of diisopropylethylamine. The solution was stirred at 150° C. for 1 hour. Ethyl acetate and water were added thereto, to perform extraction, and then the organic phase was washed with aqueous dilute hydrochloric acid and saturated brine. The resultant solution was dried over anhydrous magnesium sulfate, and the solvent was distilled off under reduced pressure. The residue was purified by column chromatography. The resultant crude product was then subjected to crystallization from a solvent, acetonitrile, to give 8.8 g of the coupler (51).

Next, the compound represented by formula (IB) of the present invention, which is the second embodiment of the compound represented by formula (I), will be explained in detail.

In the formula (IB), W represents a nitrogen-containing heterocyclic group. The heterocyclic group is a nitrogen-containing heterocyclic group whose ring-constituting atoms (which are atoms to form the ring itself, and which do not include, even if a hydrogen atom or a substituent is present on the ring, the hydrogen atom or the substituent) are preferably composed of atoms selected from nitrogen, oxygen, sulfur and carbon atoms, containing at least one nitrogen atom. The nitrogen-containing heterocyclic group may be substituent with a substituent. The nitrogen-containing heterocyclic group may be condensed to a benzene ring, an alicyclic ring, a heterocyclic ring, or the like. The number of the membered atoms of the ring (in the case that the nitrogen-containing heterocyclic group is condensed with a benzene ring, an alicyclic ring, a heterocyclic ring or the like, the number of the membered atoms of the ring is based on the manner that atoms in the condensed ring moiety are not counted) is preferably from 3 to 8, more preferably from 5 to 6, particularly preferably 5.

In the nitrogen-containing heterocyclic group, its ring moiety may be saturated or unsaturated. In the case that the ring is unsaturated, the ring may be aromatic. The ring is preferably a saturated ring or an aromatic ring (heteroaromatic ring), more preferably an aromatic ring (heteroaromatic ring), and particularly preferably a 5-membered aromatic ring (heteroaromatic ring).

The number of carbon atoms in the nitrogen-containing heterocyclic group is preferably from 0 to 60, more preferably from 1 to 50, and particularly preferably from 3 to 40. The ring-constituting atoms are preferably selected from nitrogen and carbon atoms. In this case, the number of nitrogen atoms is preferably from 1 to 2.

Examples of the nitrogen-containing heterocyclic group include 1-pyrrolidinyl, 1-pyrrolyl, 2-pyrrolyl, pyrrolyl, imidazolyl, 1-imidazolyl, pyrazolyl, 3-, 4- or 5-pyrazolyl, indolidinyl, benzimidazolyl, 1H-indazolyl, 1-indolynyl, indolyl, 2-indolyl, and 3-indolyl groups. Among these groups, preferred are 1-pyrrolyl, 2-pyrrolyl, pyrrolyl, benzimidazolyl, 1H-indazolyl, 1-indolynyl, indolyl, 2-indolyl, and 3-indolyl groups. More preferred are 2-pyrrolyl, 3-pyrrolyl, 1-indolynyl, 2-indolyl, and 3-indolyl groups. Further preferred are 1-indolynyl and 3-indolyl groups.

Examples of a substituent that the nitrogen-containing heterocyclic group may have include halogen atoms (e.g. chlorine, bromine and fluorine atoms); alkyl groups (generally having 1 to 60 carbon atoms, such as methyl, ethyl, propyl, iso-butyl, t-butyl, t-octyl, 1-ethylhexyl, nonyl, cyclohexyl, undecyl, pentadecyl, n-hexadecyl, and 3-decaneamidepropyl); alkenyl groups (generally having 2 to 60 carbon atoms, such as vinyl, allyl and oleyl); cycloalkyl groups (generally having 5 to 60 carbon atoms, such as cyclopentyl, cyclohexyl, 4-t-butylcyclohexyl, 1-indanyl, and cyclododecyl); aryl groups (generally having 6 to 60 carbon atoms, such as phenyl, p-tolyl, and naphthyl); acylamino groups (generally having 2 to 60 carbon atoms, such as acetylamino, n-butaneamido, octanoylamino, 2-hexyldecaneamido, 2-(2',4'-di-t-amylphenoxy)butaneamido, benzoylamino, and nicotineamido); sulfonamido groups (generally having 1 to 60 carbon atoms, such as methanesulfonamido, octanesulfonamido, and benzenesulfonamido); ureido groups (generally having 2 to 60 carbon atoms, such as decylaminocarbonylamino, di-n-octylaminocarbonylamino); urethane groups (generally having 2 to 60 carbon atoms, such as dodecyloxycarbonylamino, phenoxycarbonylamino, and 2-ethylhexyloxycarbonylamino), alkoxy groups (generally having 1 to 60 carbon atoms, such as methoxy, ethoxy, butoxy, n-octyloxy, hexadecyloxy, and methoxyethoxy), aryloxy groups (generally having 6 to 60 carbon atoms, such as phenoxy, 2,4-di-t-amylphenoxy, 4-t-octylphenoxy, and naphthoxy), alkylthio groups (generally having 1 to 60 carbon atoms, such as methylthio, ethylthio, butylthio, and hexadecylthio); arylthio groups (generally having 6 to 60 carbon atoms, such as phenylthio, and 4-dodecyloxyphenylthio); acyl groups (generally having 1 to 60 carbon atoms, such as acetyl, benzoyl, butanoyl, and dodecanoyl); sulfonyl groups (generally having 1 to 60 carbon atoms, such as methanesulfonyl, butanesulfonyl, and toluenesulfonyl); cyano group; carbamoyl groups (generally having 1 to 60 carbon atoms, such as N,N-dicyclohexylcarbamoyl); sulfamoyl groups (generally having 0 to 60 carbon atoms, such as N,N-dimethylsulfamoyl); hydroxyl group; sulfo group; carboxyl group; nitro group; alkylamino groups (generally having 1 to 60 carbon atoms, such as methylamino, diethylamino, octylamino, and octadecylamino); arylamino groups (generally having 6 to 60 carbon atoms, such as phenylamino, naphthylamino, and N-methyl-N-phenylamino); heterocyclic groups (generally having 0 to 60 carbon atoms. Preferred are heterocyclic groups whose ring-constituting heteroatoms are selected from nitrogen, oxygen and sulfur atoms. More preferred are such heterocyclic groups containing, as a ring-constituting atom, a carbon atom besides the heteroatom(s). The number of the membered atoms in the heteroring is preferably from 3 to 8, more preferably from 5 to 6. Examples of the heterocyclic group are the same as described as the examples of W); and acyloxy groups (generally having 1 to 60 carbon atoms, such as formyloxy, acetyloxy, myristoyl, and benzoyloxy).

The substituent that the nitrogen-containing heterocyclic group may have, may be further substituted with a substituent. In the case that the substituent that the nitrogen-containing heterocyclic group may have is an alkyl, cycloalkyl, aryl, acylamino, ureido, urethane, alkoxy, aryloxy, alkylthio, arylthio, acyl, sulfonyl, carbamoyl or sulfamoyl group, examples of a substituent that the above-specified group may have thereon include alkyl, cycloalkyl, aryl, acylamino, ureido, urethane, alkoxy, aryloxy, alkylthio, arylthio, acyl, sulfonyl, cyano, carbamoyl, and sulfamoyl groups.

Among the substituents that the nitrogen-containing heterocyclic group may have, preferred are alkyl, aryl, carbamoyl, sulfamoyl, alkoxycarbonyl, acylamino, sulfoneamido, and cyano groups.

In the formula (IB), X and Y each independently represent =O, =S or =N—R, preferably =O or =N—R, and more preferably =O.

R represents a substituent. Examples of the substituent include alkyl groups (including cycloalkyl groups, and bicycloalkyl groups), alkenyl groups (including cycloalkenyl groups, and bicycloalkenyl groups), alkynyl groups, aryl groups, heterocyclic groups, acyl groups, aryloxycarbonyl groups, alkoxycarbonyl groups, and carbamoyl groups.

More specifically, R represents an alkyl group [a straight-chain, branched or cyclic, substituted or unsubstituted alkyl group; which includes an alkyl group (preferably, an alkyl group having 1 to 30 carbon atoms, such as methyl, ethyl, n-propyl, isopropyl, t-butyl, n-octyl, eicosyl, 2-chloroethyl, 2-cyanoethyl, and 2-ethylhexyl), a cycloalkyl group (preferably, a substituted or unsubstituted cycloalkyl group having 3 to 30 carbon atoms, such as cyclohexyl, cyclopentyl, and 4-n-dodecylcyclohexyl), a bicycloalkyl group (preferably, a substituted or unsubstituted bicycloalkyl group having 5 to 30 carbon atoms, that is, a monovalent group obtained by removing one hydrogen atom from a bicycloalkane having 5 to 30 carbon atoms, such as bicyclo[1,2,2]heptane-2-yl, and bicyclo[2,2,2]octane-3-yl), and an alkyl group having a tricyclo structure or more higher ring structure. An alkyl moiety structure in substituents (for example, an alkyl moiety structure in an alkylthio group) which will be described hereinafter means an alkyl moiety structure embraced in the scope defined by the above concept]; an alkenyl group [a straight-chain, branched or cyclic, substituted or unsubstituted alkenyl group, e.g. an alkenyl group (preferably, a substituted or unsubstituted alkenyl group having 2 to 30 carbon atoms, such as vinyl, ally, prenyl, geranyl, and oleyl), a cycloalkenyl group (preferably, a substituted or unsubstituted cycloalkenyl group having 3 to 30 carbon atoms, that is, a monovalent group obtained by removing one hydrogen atom from a cycloalkene having 3 to 30 carbon atoms, such as 2-cyclopentene-1-yl, and 2-cyclohexene-1-yl), a bicycloalkenyl group (a substituted or unsubstituted bicycloalkenyl group, preferably, a substituted or unsubstituted bicycloalkenyl group having 5 to 30 carbon atoms, that is, a monovalent group obtained by removing one hydrogen atom from a bicycloalkene having a double bond, such as bicyclo[2,2,1]hept-2-ene-1-yl, and bicyclo[2,2,2]oct-2-ene-4-yl)]; an alkynyl group (preferably, a substituted or unsubstituted alkynyl group having 2 to 30 carbon atoms, such as ethynyl, propargyl, trimethylsilylethynyl); an aryl group (preferably, a substituted or unsubstituted aryl group having 6 to 30 carbon atoms, such as phenyl, p-tolyl, naphthyl, m-chlorophenyl, and o-hexadecanoylaminophenyl); a heterocyclic group (preferably, a monovalent group obtained by removing one hydrogen atom from a 5- or 6-membered, substituted or unsubstituted, and aromatic or non-aromatic heterocyclic compound, more preferably a 5- or 6-membered, aromatic heterocyclic group having 3 to 30 carbon atoms, such as 2-furyl, 2-thienyl, 2-pyrimidynyl, and 2-benzothiazolyl); an acyl group (preferably, formyl group, a substituted or unsubstituted alkylcarbonyl group having 2 to 30 carbon atoms, and a substituted or unsubstituted arylcarbonyl group having 7 to 30 carbon atoms, such as acetyl, pivaloyl, 2-chloroacetyl, stearoyl, benzoyl, and p-n-octyloxyphenylcarbonyl); an aryloxycarbonyl group (preferably, a substituted or unsubstituted aryloxycarbonyl group having 7 to 30 carbon atoms, such as phenoxycarbonyl, o-chlorophenoxycarbonyl, m-nitrophenoxycarbonyl, p-t-butylphenoxycarbonyl); an alkoxycarbonyl group (preferably, a substituted or unsubstituted alkoxycarbonyl group having 2 to 30 carbon atoms, such as methoxycarbonyl, ethoxycarbonyl, t-butoxycarbonyl, and n-octadecyloxycarbonyl); or a carbamoyl group (preferably, a substituted or unsubstituted carbamoyl group having 1 to 30 carbon atoms, such as carbamoyl, N-methylcarbamoyl, N,N-dimethylcarbamoyl, N,N-di-n-octylcarbamoyl, and N-(methylsulfonyl)carbamoyl).

About the group having a hydrogen atom, among the above-mentioned functional groups, the hydrogen atom may be removed, to further substitute the group with the above-mentioned substituent. Examples of such functional groups include alkylcarbonylaminosulfonyl, arylcarbonylaminosulfonyl, alkylsulfonylaminocarbonyl, and arylsulfonylaminocarbonyl groups. Specific examples thereof include methylsulfonylaminocarbonyl, p-methylphenylsulfonylaminocarbonyl, acetylaminosulfonyl, and benzoylaminosulfonyl.

Among the above substituents, R is preferably an alkyl group or an aryl group, and most preferably an aryl group.

$Z_B$ represents a substituted aryl group that preferably has 6 to 60 carbon atoms. Examples of the substituent of said aryl group include halogen atoms, alkyl groups (including cycloalkyl groups and bicycloalkyl groups), alkenyl groups (including cycloalkenyl groups and bicycloalkenyl groups), alkynyl groups, aryl groups, heterocyclic groups, cyano group, hydroxyl group, nitro group, carboxyl group, alkoxy groups, aryloxy groups, silyloxy groups, heterocyclic oxy groups, acyloxy groups, carbamoyloxy groups, alkoxycarbonyloxy groups, aryloxycarbonyloxy groups, amino groups (including alkylamino groups and anilino groups), acylamino groups, aminocarbonylamino groups, alkoxycarbonylamino groups, aryloxycarbonylamino groups, sulfamoylamino groups, alkyl- and aryl-sulfonylamino groups, mercapto group, alkylthio groups, arylthio groups, heterocyclic thio groups, sulfamoyl groups, sulfo group, alkyl- and aryl-sulfinyl groups, alkyl- and aryl-sulfonyl groups, acyl groups, aryloxycarbonyl groups, alkoxycarbonyl groups, carbamoyl groups, aryl- and heterocyclic-azo groups, imido groups, phosphio groups, phosphinyl groups, phosphinyloxy groups, phosphinylamino groups, and silyl groups.

The substituent of the substituted aryl group will be described in more detail hereinafter.

Examples of the substituent of the substituted aryl group include halogen atoms (such as chlorine, bromine and iodide atoms); alkyl groups [straight-chain, branched or cyclic, substituted or unsubstituted alkyl; which include alkyl groups (preferably, alkyl groups having 1 to 30 carbon atoms, such as methyl, ethyl, n-propyl, isopropyl, t-butyl, n-octyl, eicosyl, 2-chloroethyl, 2-cyanoethyl, and 2-ethylhexyl), cycloalkyl groups (preferably, substituted or unsubstituted cycloalkyl groups having 3 to 30 carbon atoms, such as cyclohexyl, cyclopentyl, and 4-n-dodecylcyclohexyl), bicycloalkyl groups (preferably, substituted or unsubstituted bicycloalkyl groups having 5 to 30 carbon atoms, that is, monovalent groups obtained by removing one hydrogen atom from bicycloalkane having 5 to 30 carbon atoms, such as bicyclo[1,2,2]heptane-2-yl, and bicyclo[2,2,2]octane-3-yl), and tricyclo structures or more higher ring structures. An alkyl moiety structure in substituents (for example, an alkyl moiety structure in an alkylthio group) which will be described hereinafter means an alkyl moiety structure embraced in the scope defined by the above concept]; alkenyl groups [straight-chain, branched or cyclic, substituted or unsubstituted alkenyl, e.g. alkenyl groups (preferably, substituted or unsubstituted alkenyl groups having 2 to 30 carbon atoms, such as vinyl, ally, prenyl, geranyl, and oleyl), cycloalkenyl groups (preferably, substituted or unsubstituted cycloalkenyl groups having 3 to 30 carbon atoms, that is, monovalent groups obtained by removing one hydrogen atom from cycloalkene having 3 to 30 carbon atoms, such as 2-cyclopentene-1-yl, and 2-cyclohexene-1-yl), and bicycloalkenyl groups (substituted or unsubstituted bicycloalkenyl groups, preferably, substituted or unsubstituted bicycloalkenyl groups having 5 to 30 carbon atoms, that is, monovalent groups obtained by removing one hydrogen atom from bicycloalkene having a double bond, such as bicyclo[2,2,1]hept-2-ene-1-yl, and bicyclo[2,2,2]oct-2-ene-4-yl)]; alkynyl groups (preferably, substituted or unsubstituted alkynyl groups having 2 to 30 carbon atoms, such as ethynyl, propargyl, trimethylsilylethynyl); aryl groups (preferably, substituted or unsubstituted aryl groups having 6 to 30 carbon atoms, such as phenyl, p-tolyl, naphthyl, m-chlorophenyl, o-hexadecanoylaminophenyl); heterocyclic groups (preferably, monovalent groups obtained by removing one hydrogen atom from 5- or 6-membered, substituted or unsubstituted, and aromatic or non-aromatic heterocyclic compounds, more preferably 5- or 6-membered aromatic heterocyclic groups having 3 to 30 carbon atoms, such as 2-furyl, 2-thienyl, 2-pyrimidynyl, and 2-benzothiazolyl); cyano group; hydroxyl group; nitro group; carboxyl group; alkoxy groups (preferably, substituted or unsubstituted alkoxy groups having 1 to 30 carbon atoms, such as methoxy, ethoxy, isopropoxy, t-butoxy, n-octyloxy, and 2-methoxyethoxy); aryloxy groups (preferably, substituted or unsubstituted aryloxy groups having 6 to 30 carbon atoms, such as phenoxy, 2-methylphenoxy, 4-t-butylphenoxy, 3-nitrophenoxy, and 2-tetradecanoylaminophenoxy); silyloxy groups (preferably, silyloxy groups having 3 to 20 carbon atoms, such as trimethylsilyloxy, and t-butyldimethylsilyloxy); heterocyclic oxy groups (preferably, substituted or unsubstituted heterocyclic oxy groups having 2 to 30 carbon atoms, such as 1-phenyltetrazole-5-oxy, and 2-tetrahydropyranyloxy); acyloxy groups (preferably, formyloxy group, substituted or unsubstituted alkylcarbonyloxy groups having 2 to 30 carbon atoms, and substituted or unsubstituted arylcarbonyloxy groups having 6 to 30 carbon atoms, such as formyloxy, acetyloxy, pyvaloyloxy, stearoyloxy, benzoyloxy, p-methoxyphenylcarbonyloxy); carbamoyloxy groups (preferably, substituted or unsubstituted carbamoyloxy groups having 1 to 30 carbon atoms, such as N,N-dimethylcarbamoyloxy, N,N-diethylcarbamoyloxy, morpholinocarbonyloxy, N,N-di-n-octylaminocarbonyloxy, N-n-octylcarbamoyloxy), alkoxycarbonyloxy groups (preferably, substituted or unsubstituted alkoxycarbonyloxy groups having 2 to 30 carbon atoms, such as methoxycarbonyloxy, ethoxycarbonyloxy, t-butoxycarbonyloxy, and n-octylcarbonyloxy); aryloxycarbonyloxy groups (preferably, substituted or unsubstituted aryloxycarbonyloxy groups having 7 to 30 carbon atoms, such as phenoxycarbonyloxy, p-methoxyphenoxycarbonyloxy, p-n-hexadecyloxyphenoxycarbonyloxy); amino groups (preferably, amino group, substituted or unsubstituted alkylamino groups having 1 to 30 carbon atoms, and substituted or unsubstituted anilino groups having 6 to 30 carbon atoms, such as amino, methylamino, dimethylamino, anilino, N-methyl-anilino, and diphenylamino); acylamino groups (preferably, formylamino group, substituted or unsubstituted alkylcarbonylamino groups having 1 to 30 carbon atoms, and substituted or unsubstituted arylcarbonylamino groups having 6 to 30 carbon atoms, such as formylamino, acetylamino, pyvaloylamino, lauroylamino, benzoylamino, 3,4,5-tri-n-octyloxyphenylcarbonylamino); aminocarbonylamino groups (preferably, substituted or unsubstituted aminocarbonylamino groups having 1 to 30 carbon atoms, such as carbamoylamino, N,N-dimethylaminocarbonylamino, N,N-diethylaminocarbonylamino, and morpholinocarbonylamino); alkoxycarbonylamino groups (preferably, substituted or unsubstituted alkoxycarbonylamino groups having 2 to 30 carbon atoms, such as methoxycarbonylamino, ethoxycarbonylamino, t-butoxycarbonylamino, n-octadecyloxycarbonylamino, and N-methyl-methoxycarbonylamino); aryloxycarbonylamino groups (preferably, substituted or unsubstituted aryloxycarbonylamino groups having 7 to 30 carbon atoms, such as phenoxycarbonylamino, p-chlorophenoxycarbonylamino, m-n-octyloxy, and phenoxycarbonylamino); sulfamoylamino groups (preferably, substituted or unsubstituted sulfamoylamino groups having 0 to 30 carbon atoms, such as sulfamoylamino, N,N-dimethylaminosulfonylamino, and N-n-octylaminosulfonylamino); alkyl- and aryl-sulfonylamino groups (preferably, substituted or unsubstituted alkylsulfonylamino groups having 1 to 30 carbon atoms, and substituted or unsubstituted arylsulfonylamino groups having 6 to 30 carbon atoms, such as methylsulfonylamino, butylsulfonylamino, phenylsulfonylamino, 2,3,5-trichlorophenylsulfonylamino, p-methylphenylsulfonylamino); mercapto group; alkylthio groups (preferably, substituted or unsubstituted alkylthio groups having 1 to 30 carbon atoms, such as methylthio, ethylthio, and n-hexadecylthio); arylthio groups (preferably, substituted or unsubstituted arylthio groups having 6 to 30 carbon atoms, such as phenylthio, p-chlorophenylthio, and m-methoxyphenylthio); heterocyclic thio groups (preferably, substituted or unsubstituted heterocyclic thio groups having 2 to 30 carbon atoms, such as 2-benzothiazolylthio, and 1-phenyltetrazole-5-ylthio); sulfamoyl groups (preferably, substituted or unsubstituted sulfamoyl groups having 0 to 30 carbon atoms, such as N-ethylsulfamoyl, N-(3-dodecyloxypropyl)sulfamoyl; N,N-dimethylsulfamoyl, N-acetylsulfamoyl, N-benzoylsulfamoyl, N-(N'-phenylcarbamoyl)sulfamoyl); sulfo group; alkyl- and aryl-sulfinyl groups (preferably, substituted or unsubstituted alkylsulfinyl groups having 1 to 30 carbon atoms, and substituted or unsubstituted arylsulfinyl groups having 6 to 30 carbon atoms, such as methylsulfinyl, ethylsulfinyl, phenylsulfinyl, and p-methylphenylsulfinyl); alkyl- and aryl-sulfonyl groups (preferably, substituted or unsubstituted alkylsulfonyl groups having 1 to 30 carbon atoms, and substituted or unsubstituted arylsulfonyl groups having 6 to 30 carbon atoms, such as methylsulfonyl, ethylsulfonyl, phenylsulfonyl, and p-methylphenylsulfonyl); acyl groups (preferably, formyl group, substituted or unsubstituted alkylcarbonyl groups having 2 to 30 carbon atoms, and substituted or unsubstituted arylcarbonyl groups having 7 to 30 carbon atoms, such as acetyl, pyvaloyl, 2-chloroacetyl, stearoyl, benzoyl, and p-n-octyloxyphenylcarbonyl); aryloxycarbonyl groups (preferably, substituted or unsubstituted aryloxycarbonyl groups having 7 to 30 carbon atoms, such as phenoxycarbonyl, o-chlorophenoxycarbonyl, m-nitrophenoxycarbonyl, and p-t-butylphenoxycarbonyl); alkoxycarbonyl groups (preferably, substituted or unsubstituted alkoxycarbonyl groups having 2 to 30 carbon atoms, such as methoxycarbonyl, ethoxycarbonyl, t-butoxycarbonyl, and n-octadecyloxycarbonyl); carbamoyl groups (preferably, substituted or unsubstituted carbamoyl groups having 1 to 30 carbon atoms, such as carbamoyl, N-methylcarbamoyl, N,N-dimethylcarbamoyl), N,N-di-n-octylcarbamoyl, N-(methylsulfonyl)carbamoyl); aryl azo groups and heterocyclic azo groups (preferably, substituted or unsubstituted aryl azo groups having 6 to 30 carbon atoms, and substituted or unsubstituted heterocyclic azo groups having 3 to 30 carbon atoms, such as phenylazo, p-cholorophenylazo, 5-ethylthio-1,3,4-thiadiazole-2-ylazo); imido groups (preferably, N-succimido, and N-phthalimido); phosphino groups (preferably, substituted or unsubstituted phosphino groups having 2 to 30 carbon atoms, such as dimethylphosphino, diphenylphosphino, and methylphenoxyphosphino); phosphinyl groups (preferably, substituted or unsubstituted phosphinyl groups having 2 to 30 carbon atoms, such as phosphinyl, dioctyloxyphosphinyl, and diethoxyphosphinyl); phosphinyloxy groups (preferably, substituted or unsubstituted phosphinyloxy groups having 2 to 30 carbon atoms, such as diphenoxyphosphinyloxy, and dioctyloxyphosphinyloxy); phosphinylamino groups (preferably, substituted or unsubstituted phosphinylamino groups having 2 to 30 carbon atoms, such as dimethoxyphoshinylamino, and dimethylaminophoshinylamino); and silyl groups (preferably, substituted or unsubstituted silyl groups having 3 to 30 carbon atoms, such as trimethylsilyl, t-butyldimethylsilyl, and phenyldimethylsilyl).

About groups having a hydrogen atom, among the above-mentioned functional groups, it is allowable to remove the hydrogen atom, to further substitute with any one of the groups as described above. Examples of such functional groups include alkylcarbonylaminosulfonyl, arylcarbonylaminosulfonyl, alkylsulfonylaminocarbonyl, and arylsulfonylaminocarbonyl groups. More specific examples thereof include methylsulfonylaminocarbonyl, p-methylphenylsulfonylaminocarbonyl, acetylaminosulfonyl, and benzoylaminosulfonyl.

Preferred are halogen atoms, and alkyl, aryl, carbamoyl, sulfamoyl, alkoxycarbonyl, acylamino, sulfonamido, sulfonyl, alkoxy and aryloxy groups.

$Z_B$ is particularly preferably a phenyl group substituted with a halogen atom or an alkoxy group on, at least, the 2-position thereof. This phenyl group may also have one or more additional substituents on the 3- to 6-positions thereof, and the phenyl group also having a substituent on the 5-position thereof in addition to the above substituents is particularly preferred.

The coupler of the present invention, represented by the above formula, may be made to form a dimer or a higher polymer, or it may be bonded to a polymer chain, via W, R or $Z_B$.

Specific examples of the coupler of the present invention will be described hereinafter, but the present invention is not limited to these examples.

In the following chemical formulae, -ph represents a phenyl group ($—C_6H_5$).

(1)'

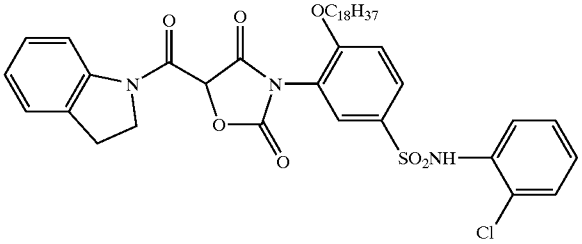

(2)'

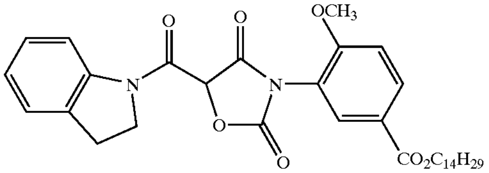

(3)'

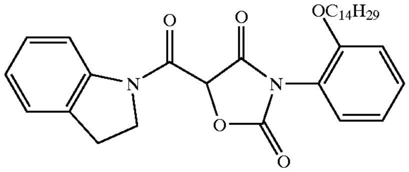

(4)'

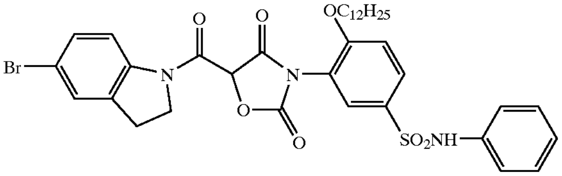

-continued
(5)'
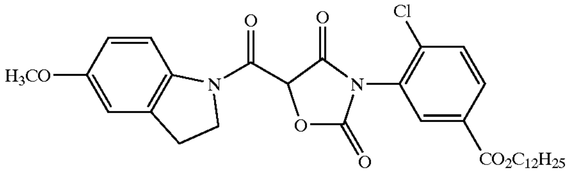
(6)'
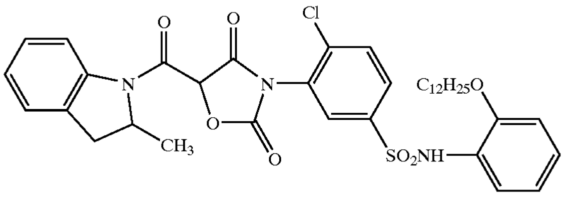
(7)'
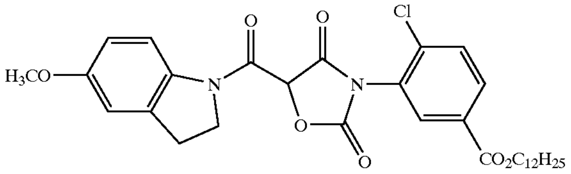
(8)'
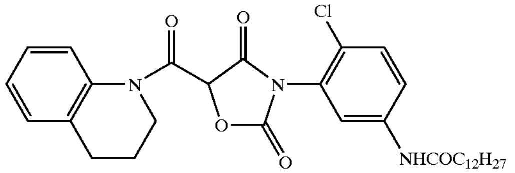
(9)'
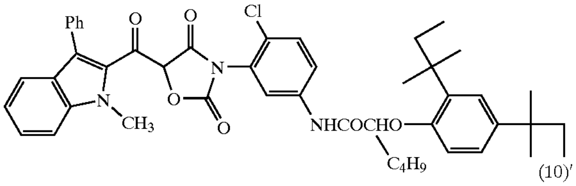
(10)'
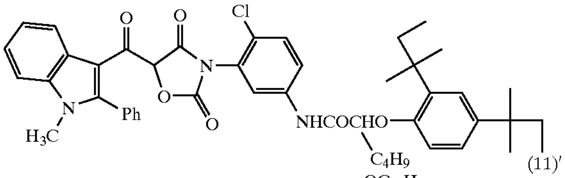
(11)'
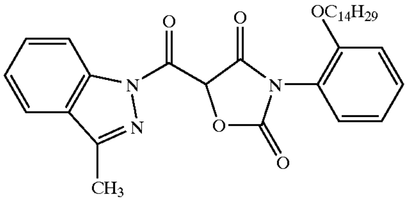
(12)'
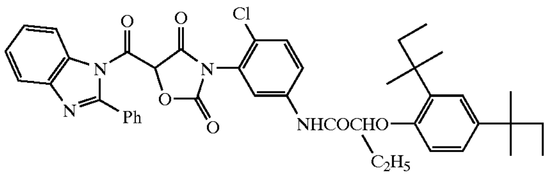
-continued
(13)'
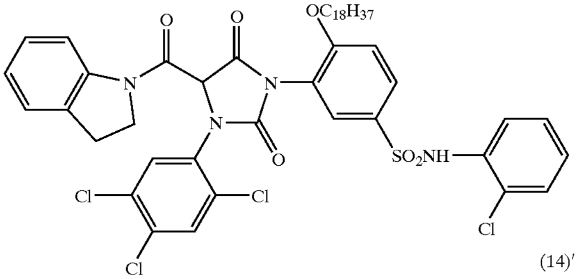
(14)'
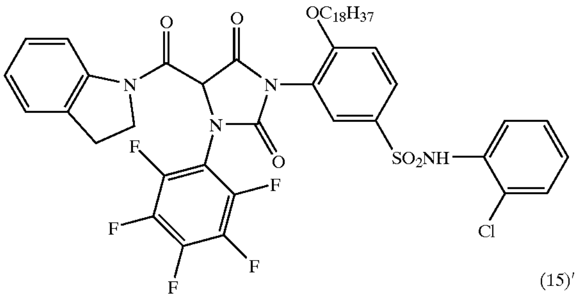
(15)'
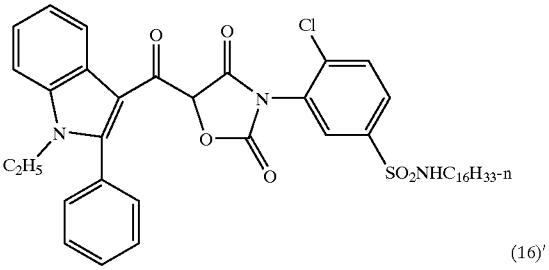
(16)'
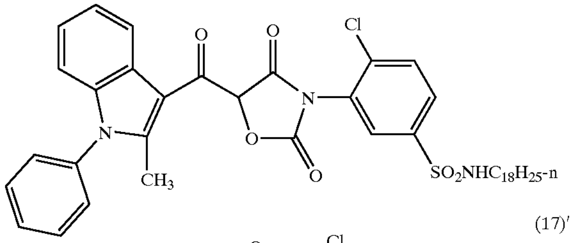
(17)'
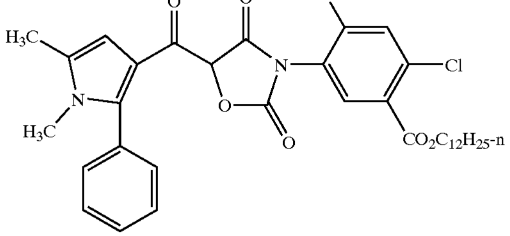
(18)'
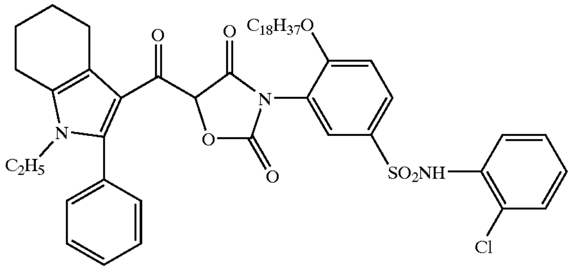

-continued
(19)'
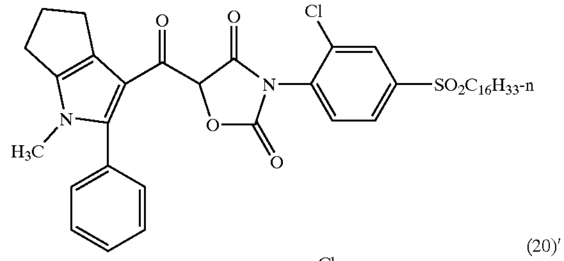
(20)'
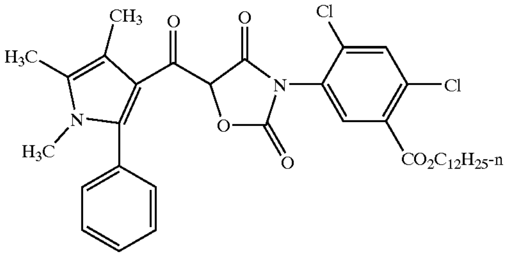
(21)'
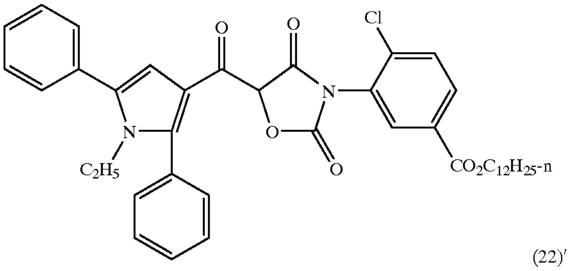
(22)'
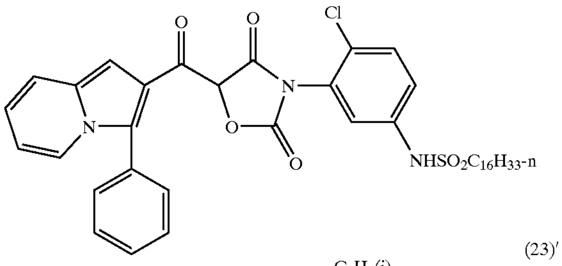
(23)'
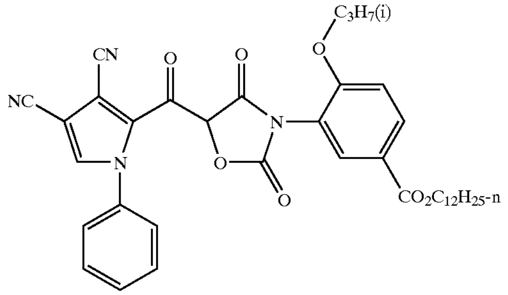
(24)'
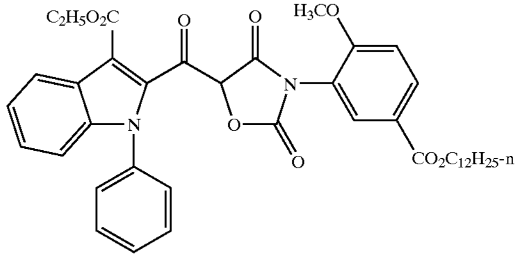
-continued
(25)'
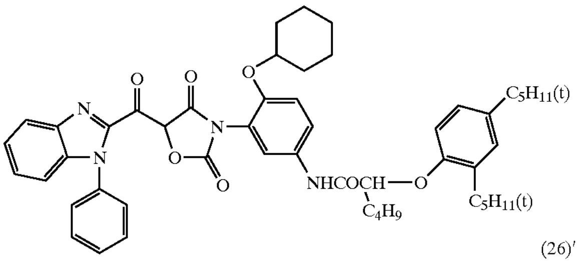
(26)'
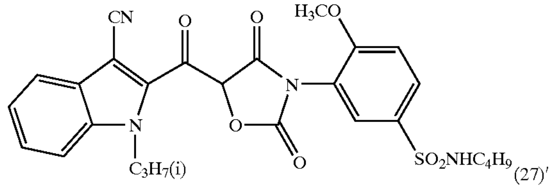
(27)'
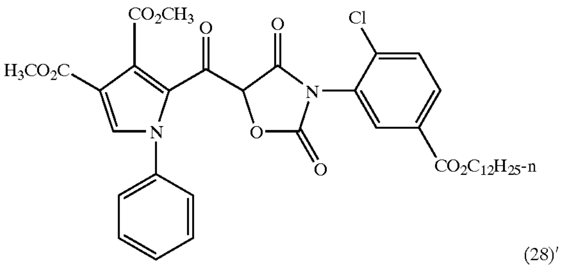
(28)'
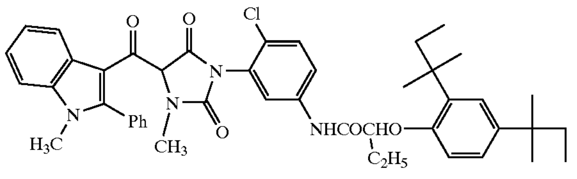
The coupler of the present invention is a new dye-forming coupler, and can be synthesized from inexpensive raw materials in relatively short steps. The followings will show specific examples of the synthesis process.
Synthetic Example 2-1
Synthesis of the Coupler (1)'
The coupler (1)' was synthesized through the following route:
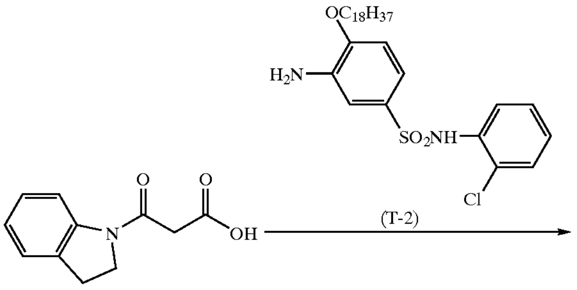

-continued

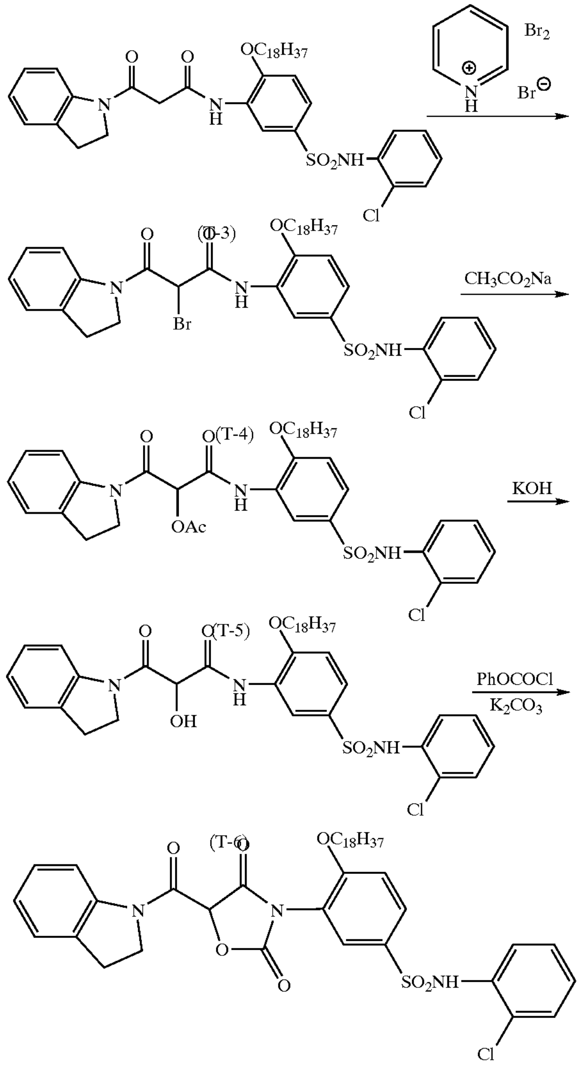

Coupler (1)'

Synthesis of the Compound (T-3)

Into 170 ml of dimethylformamide were dissolved 26.0 g (0.13 mole) of the compound (T-1), and 64.0 g (0.12 mole) of the compound (T-2), and then thereto was dropwise added 31 g (0.15 mole) of dicyclohexylcarbodiimide dissolved in 50 ml of dimethylformamide. The resultant solution was stirred at room temperature for 3 hours. Thereafter, to the reaction system were added 3 ml of acetic acid and 12 ml of methanol, and then the solution was stirred for 30 minutes. Precipitated dicyclohexylurea was removed by filtration, and 500 ml of methanol was added to the filtrate. The resultant solution was heated to 50° C., and subsequently 12 ml of water was added thereto. The solution was then cooled at room temperature. Precipitated crystals were collected by filtration, and recrystallized from 150 ml of methanol, to give 73 g (yield: 82%) of the compound (T-3) as white crystals.

Synthesis of the Compound (T-4)

Into 300 ml of chloroform was dissolved 45 g (0.059 mol) of the compound (T-3), and then 20 g (0.059 mol) of pyridiumperbromide hydrobromide was added thereto, while stirring. At room temperature, the resultant solution was further stirred for 2 hours. Subsequently, the reaction solution was washed with water and saturated brine, and then the organic phase was dried over magnesium sulfate. The magnesium sulfate was removed by filtration and then chloroform was distilled off under reduced pressure. The residue was purified by column chromatography, to give 40 g (yield: 83%) of the compound (T-4) as white crystals.

Synthesis of the Compound (T-5)

Into 120 ml of dimethylformamide was dissolved 3.9 g (0.048 mole) of sodium acetate, and then to this solution was dropwise added 35 g (0.043 mol) of the compound (T-4) dissolved in 120 ml of methylene chloride, while stirring at room temperature. The resultant solution was further stirred at room temperature for 5 hours, and subsequently 200 ml of ethyl acetate was added thereto. The solution was washed with aqueous dilute hydrochloric acid and saturated brine. The organic phase was dried and ethyl acetate was distilled off under reduced pressure. The residue was purified by column chromatography, to give 25 g (yield: 73%) of the compound (T-5) as white crystals.

Synthesis of the Compound (T-6)

Into 250 ml of methanol was dissolved 2 g of potassium hydroxide, and then 25 g (0.031 mole) of the compound (T-5) was added to the solution, while stirring at room temperature. The resultant solution was stirred at room temperature for 2 hours, and then 2.5 ml of concentrated hydrochloric acid was added thereto. Precipitated crystals were collected by filtration. The resultant crystals were recrystallized from acetonitrile, to give 22 g (yield: 92%) of the compound (T-6) as white crystals.

Synthesis of the Coupler (1)'

Into 70 ml of dimethylformamide was dissolved 10 g (0.013 mole) of the compound (T-6), and then 5.5 g (0.040 mole) of potassium carbonate was added thereto. While this solution was cooled with ice and stirred, 2 ml (0.016 mole) of phenyl chlorocarbonate was dropwise added thereto. After the completion of dropwise addition, the temperature of the solution was raised to room temperature. The solution was further stirred at room temperature for 8 hours, and then 100 ml of ethyl acetate was added thereto. The resultant solution was washed with dilute hydrochloric acid and saturated brine. The organic phase was dried and then ethyl acetate was distilled off under reduced pressure. The residue was purified by column chromatography, to give 2.4 g (yield: 23%) of the target coupler (1)' as white crystals.

Synthetic Example 2-2

Synthesis of the Coupler (3)'

The coupler (3)' was synthesized through the following route:

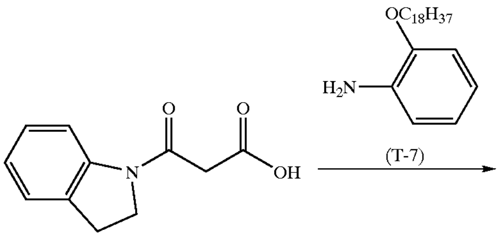

(T-1)

-continued

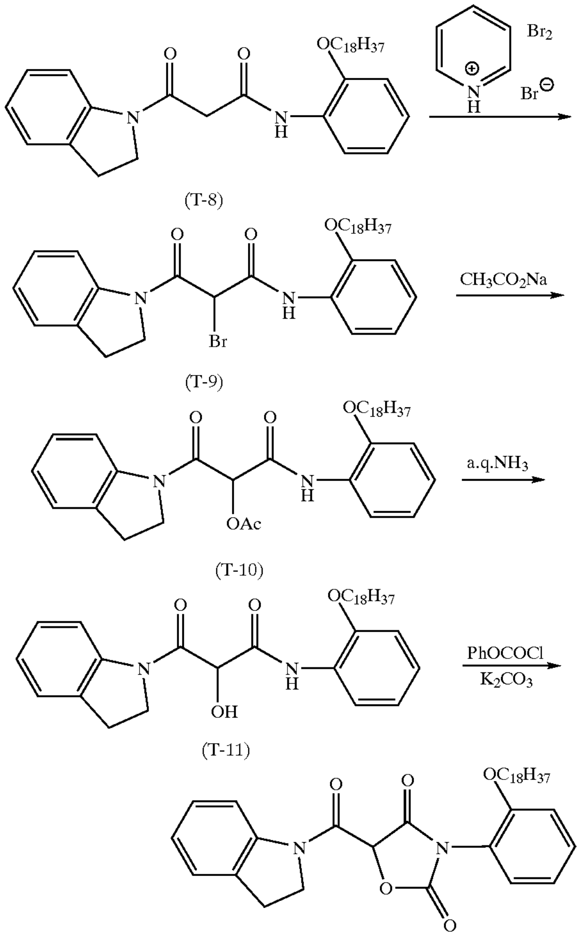

(T-8)

(T-9)

(T-10)

(T-11)

Coupler (3)'

Synthesis of the Compound (T-8)

Into 200 ml of dimethylformamide, were dissolved 20 g (0.098 mole) of the compound (T-1) and 30 g (0.098 mole) of the compound (T-7), and then thereto was dropwise added 24 g (0.12 mole) of dicyclohexylcarbodiimide dissolved in 50 ml of dimethylformamide. The resultant solution was stirred at room temperature for 3 hours. Thereafter, to the reaction system was added 500 ml of chloroform, following further stirring for 30 minutes. Precipitated dicyclohexylurea was removed by filtration, and 3 ml of acetic acid and 5 ml of methanol were added to the filtrate, following further stirring for 30 minutes, and then the reaction solution was washed with aqueous dilute hydrochloric acid and saturated brine. The organic phase was dried and then chloroform was distilled off under reduced pressure. The residue was recrystallized from acetonitrile, to give 30 g (yield: 62%) of the compound (T-8) as white crystals.

Synthesis of the Compound (T-9)

Into 400 ml of chloroform was dissolved 29 g (0.059 mol) of the compound (T-8), and then 22 g (0.069 mol) of pyridiumperbromide hydrobromide was added thereto, while stirring. At room temperature, the resultant solution was further stirred for 1 hour. The reaction solution was washed with water and saturated brine, and then the organic phase was dried over magnesium sulfate. The magnesium sulfate was removed by filtration and then chloroform was distilled off under reduced pressure. The residue was purified by column chromatography, to give 26 g (yield: 77%) of the compound (T-9) as white crystals.

Synthesis of the Compound (T-10)

Into 200 ml of dimethylformamide was dissolved 4.0 g (0.049 mole) of sodium acetate, and then thereto was dropwise added 25 g (0.044 mol) of the compound (T-9) dissolved in 100 ml of methylene chloride, while stirring at room temperature. The resultant solution was further stirred at room temperature for 6 hours, and then 200 ml of ethyl acetate was added thereto. The resultant solution was washed with aqueous dilute hydrochloric acid and saturated brine. The organic phase was dried and then ethyl acetate was distilled off under reduced pressure. The residue was purified by column chromatography, to give 24 g (yield: 98%) of the compound (T-10) as white crystals.

Synthesis of the Compound (T-11)

Into 200 ml of methanol was suspended 24 g (0.043 g) of the compound (T-10), and then 6.5 ml of 25% aqueous ammonia was added thereto. The reaction liquid was stirred for 3 hours, and then 7 ml of concentrated hydrochloric acid and 200 ml of water were added to the reaction system. Precipitated crystals were collected by filtration and were successively washed with water and methanol. The resultant crystals were recrystallized from acetonitrile, to give 17 g (yield: 78%) of the compound (T-11) as white crystals.

Synthesis of the Coupler (3)'

Into 200 ml of N-methyl-2-pyrrolidone was dissolved 15 g (0.030 mole) of the compound (T-11), and then 12.2 g (0.088 mole) of potassium carbonate was added thereto. While this solution was cooled with ice and stirred, 7.5 ml (0.059 mole) of phenyl chlorocarbonate was dropwise added thereto. After the completion of the dropwise addition, the temperature of the reaction liquid was raised to room temperature, followed by further stirring at room temperature for 8 hours. Then, the reaction solution was poured into ice water to which 5 ml of concentrated hydrochloric acid had been added, and then 300 ml of ethyl acetate was added thereto, followed by stirring. The organic phase was washed with dilute hydrochloric acid and saturated brine. The washed organic phase was dried and then ethyl acetate was distilled off under reduced pressure. The residue was purified by column chromatography, to give 7.9 g (yield: 50%) of the target coupler (3)' as white crystals.

The mechanism of color-forming reaction of the dye-forming coupler represented by formula (I) of the present invention will be explained below, referring to the coupler of the formula (IB) as an example.

The dye-forming coupler represented by formula (IB) of the present invention reacts with an oxidized product of an aromatic primary amine developing agent, to form a dye according to the following reaction mechanism.

Color-forming reaction mechanism

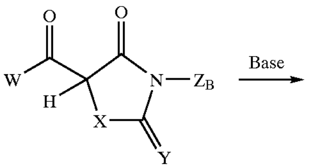

(IB)

-continued

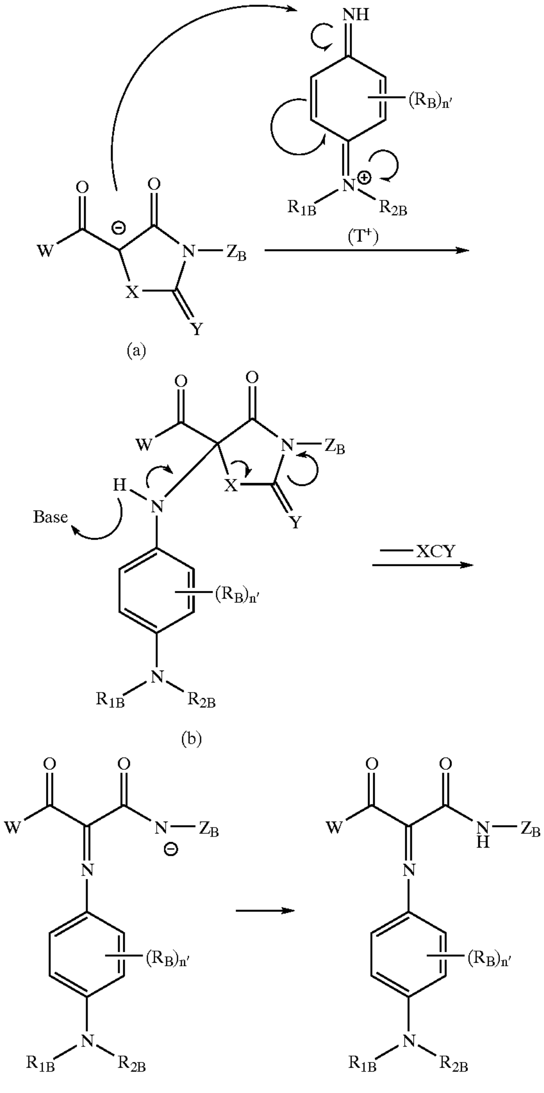

(a) (T+) (b) (c) Dye

In the above-mentioned reaction scheme, the oxidized product of the aromatic primary amine developing agent is represented as ($T^+$). The formula ($T^+$) is described on the assumption that typically $R_B$, $R_{1B}$ and $R_{2B}$ each independently represent a substituent and n' is an integer of 0 or 1 to 4. The "Base" represents a base.

The hydrogen atom on the carbon atom substituted with the oxygen atom (X) and the WCO— group, in the dye-forming coupler (IB), is withdrawn by a base, to form an anion. This anion (a) is subjected to an ordinary coupling reaction with the oxidized product ($T^+$) of an aromatic primary amine developing agent, to form an intermediate (b). Subsequently, the hydrogen atom on the nitrogen atom substituted with the carbon atom in the formula (IB) by the coupling reaction, in the intermediate (b), is withdrawn by the base, so that the oxygen atom (X) splits off from the carbon atom substituted with ($T^+$). As a result, the 5-membered ring is opened so that XCY is removed (when X and Y each are, for example, an oxygen atom, $CO_2$ is removed (decarboxylation)). In this way, an intermediate (c) is given. A hydrogen atom is supplied to the intermediate (c), from a solvent, such as water, in the reaction system, so that the intermediate (c) turns to a dye (Dye). Therefore, this dye-forming coupler is classified into a 2-equivalent coupler.

(Silver Halide Photographic Light-sensitive Material)

The light-sensitive material of the present invention is a silver halide photographic light-sensitive material, in which at least one light-sensitive layer is formed on a support, and the light-sensitive material contains the dye-forming coupler that is the compound represented by formula (I) of the present invention (that is, the compound represented by formula (IA) or (IB)), in at least one layer of the light-sensitive layer(s). The coupler is generally contained in a hydrophilic colloid layer composed of an ordinary gelatin binder. An ordinary light-sensitive material can be made by providing light-sensitive emulsion layers (light-sensitive layers) composed of at least one blue-sensitive silver halide emulsion layer, at least one green-sensitive silver halide emulsion layer, and at least one red-sensitive silver halide emulsion layer, on a support. The order of these light-sensitive layers may be selected arbitrarily. An infrared ray-sensitive silver halide emulsion layer may be used instead of at least one of the above-mentioned light-sensitive emulsion layers. Color reproduction based on subtractive color processes can be performed by incorporating, into each of these light-sensitive emulsion layers, a silver halide emulsion having sensitivity in the corresponding wavelength range, and a coupler for forming a dye having a color complementary to the color of sensitizing light. However, the light-sensitive emulsion layer and the developed hue of the coupler may not have a corresponding relationship as described above.

The dye-forming coupler represented by formula (I) can be incorporated into any one of the light-sensitive emulsion layers (preferably, the blue-sensitive silver halide emulsion layer or the green-sensitive silver halide emulsion layer, particularly preferably the blue-sensitive silver halide emulsion layer).

The dye-forming coupler represented by formula (I) is useful as various types of dye-forming couplers without particular limitation. The dye-forming coupler is useful mainly as a yellow coupler or a magenta coupler, particularly as a yellow coupler, for example, in conventional color light-sensitive materials, when combined with a p-phenylenediamine color-developing agent. Therefore, in the case that a p-phenylenediamine is used as a color-developing agent for the silver halide photographic light-sensitive material of the present invention, the dye-forming coupler represented by formula (I) is incorporated preferably into the yellow coupler- or magenta coupler-containing color-forming layer, particularly preferably into the yellow color-forming layer. That is, the coupler of the present invention may be contained in any one of the light-sensitive emulsion layers, but it is contained preferably in the blue-sensitive silver halide emulsion layer or green-sensitive silver halide emulsion layer, particularly preferably in the blue-sensitive silver halide emulsion layer. In systems wherein a color-developing agent other than p-phenylenediamines is used, the dye-forming coupler represented by formula (I) is useful as a dye-forming coupler that can give a dye having various types of hue.

In the silver halide photographic light-sensitive material of the present invention, the coupler is added preferably in an amount of $1\times10^{-3}$ to 1 mole, more preferably in an amount of $2\times10^{-3}$ to $3\times10^{-1}$ mole, per mole of silver halide.

The coupler of the present invention may be incorporated in a light-sensitive material by various known dispersion processes. It is preferred to use an oil-in-water dispersion process in which first a compound is dissolved in a high-boiling-point organic solvent (in combination with a low-boiling-point organic solvent as occasion demands), thereby forming a solution and then the resulting solution is emulsified and dispersed in an aqueous gelatin solution, which is then added to a silver halide emulsion. Examples of the high-boiling-point organic solvent for use in the oil-in-water dispersion process are described in, for example, JP-A-5-313327, JP-A- 5-323539, JP-A-5-323541, JP-A-6-258803, JP-A-8-262662, and U.S. Pat. No. 2,322,027. Further, the steps, effects and specific examples of latex polymers for impregnation, which are used in the latex dispersion process as one of polymer dispersion process, are described in, for example, U.S. Pat. No. 4,199,363, West German Patent Application (OLS) Nos. 2,541,274 and 2,541,230, JP-B-53-41091 ("JP-B" means examined Japanese patent publication), and European Patent Publication No. 029104. Further, dispersion processes using an organic solvent-soluble polymer are described in, for example, PCT International Publication WO 88/00723 and JP-A-5-150420. Methacrylate-series or acrylamide-series polymers are preferred. In particular, the use of acrylamide-series polymers is preferred, in view of enhancing image-fastness.

The term "high boiling point" herein used refers to a boiling point of 175° C. or more at ordinary pressure.

Examples of the high-boiling-point solvent for use in the present invention are described in, for example, U.S. Pat. No. 2,322,027. Specific examples of the high-boiling-point organic solvent having a boiling point of 175° C. or more at ordinary pressure include phthalic acid esters {e.g., dibutyl phthalate, dicyclohexyl phthalate, di-2-ethylhexyl phthalate, decyl phthalate, bis(2,4-di-tert-amylphenyl) phthalate, bis(2,4-di-tert-amylphenyl) iso-phthalate, bis(1,1-di-ethylpropyl) phthalate}, esters of phosphoric acid or phosphonic acid (e.g., triphenyl phosphate, tricresyl phosphate, 2-ethylhexyldiphenyl phosphate, tricyclohexyl phosphate, tri-2-ethlhexyl phosphate, tridodecyl phosphate, tributoxyethyl phosphate, trichloropropyl phosphate, di-2-ethylhexylphenyl phosphonate), benzoic acid esters (e.g., 2-ethylhexyl benzoate, dodecyl benzoate, 2-ethylhexyl p-hydroxybenzoate), amides (e.g., N,N-diethyldodecaneamide, N,N-diethyllaurylamide, N-tetradecylpyrrolidone), sulfonamides (e.g., N-butylbenzenesulfonamide), alcohols and phenols (e.g., isostearyl alcohol, 2,4-di-tert-amylphenol), aliphatic carboxylic acid esters (e.g., bis-(2-ethylhexyl) sebacate, dioctyl azelate, glycerol tributylate, isostearyl lactate, trioctyl citrate), aniline derivatives (e.g., N,N-dibutyl-2-butory-5-tert-octylaniline), hydrocarbons (e.g., paraffin, dodecylbenzene, diisopropylnaphthalate), and chlorinated paraffins. In particular, the foregoing phosphoric acid esters, and hydrogen-providing compounds described in JP-A-6-258803 and JP-A-8-262662 are preferably used, since they help to provide an excellent hue.

In order to reduce a load to environment, it is preferred to use compounds described in European Patent Nos. EP-969320A1 and EP-969321A1, in place of the foregoing phthalic acid esters. In addition to the above-mentioned compounds, tributyl citrate, pentaglycelol triesters and the like may be used.

The dielectric constant of the high-boiling-point organic solvent varies depending on the purpose for use, but it is preferably in the range of 2.0 to 7.0, more preferably in the range of 3.0 to 6.0.

The high-boiling-point organic solvent is used preferably in an amount of 0 to 10 times of the mass of the coupler, more preferably in an amount of 0 to 4 times thereof.

Further, as an auxiliary solvent, an organic solvent having a boiling point of 30° C. or more, preferably in the range of from 50° C. to about 160° C. may be used. Typical examples of the auxiliary solvent include ethyl acetate, butyl acetate, ethyl propionate, methyl ethyl ketone, cyclohexane, 2-ethoxyethyl acetate and dimethylformamide.

All or a part of the auxiliary solvent may be removed from an emulsified dispersion by means of a vacuum distillation, a noodle washing, an ultrafiltration, or the like, as occasion demands for the purpose of improving storage stability with the lapse of time in the state of the emulsified dispersion, or inhibiting a fluctuation in photographic properties or improving storage stability with the lapse of time of the final coating composition in which the emulsified dispersion is mixed with a silver halide emulsion.

The average particle size of the oleophilic fine particle dispersion thus obtained is preferably in the range of 0.001 to 1.0 μm, more preferably in the range of 0.05 to 0.30 μm, and most preferably in the range of 0.08 to 0.20 μm. The average particle size can be determined with a measuring device such as Coulter submicron particle analyzer model N4 (trade name, made by Coulter Electronics Co., Ltd.). If the average particle size of the oleophilic fine particles dispersion is too large, such problems easily arise that a color-formation efficiency of a coupler is lessened, or gloss on the surface of a light-sensitive material deteriorates. In contrast, if the average particle size is too small, viscosity of the dispersion increases and consequently a handling becomes difficult at the time of production.

The amount to be used (in terms of weight ratio) of a dispersion of oleophilic fine particles composed of the coupler of the present invention to a dispersion medium is preferably in the range of 2 to 0.1, more preferably in the range of 1.0 to 0.2, per 1 part by weight of the dispersion medium. Examples of the dispersion medium include gelatin that is a typical example, and in addition thereto mention can be made of hydrophilic polymers, such as polyvinyl alcohol. The oleophilic fine-particle dispersion may contain various compounds, together with the coupler of the present invention, according to the purpose of use.

Other known photographic materials and additives may be used in the silver halide photographic light-sensitive material of the present invention.

For example, as a photographic support (base), a transmissive type support and a reflective type support may be used. As the transmissive type support, it is preferred to use transparent supports, such as a cellulose nitrate film, and a transparent film of polyethylene terephthalate, or a polyester of 2,6-naphthalenedicarboxylic acid (NDCA) and ethylene glycol (EG), or a polyester of NDCA, terephthalic acid and EG, provided thereon with an information-recording layer such as a magnetic layer. As the reflective type support, it is especially preferable to use a reflective support having a substrate laminated thereon with a plurality of polyethylene layers or polyester layers (water-proof resin layers or laminate layers), at least one of which contains a white pigment such as titanium oxide.

A more preferable reflective support for use in the present invention is a support having a paper substrate provided with a polyolefin layer having fine holes, on the same side as silver halide emulsion layers. The polyolefin layer may be composed of multi-layers. In this case, it is more preferable for the support to be composed of a fine hole-free polyolefin (e.g., polypropylene, polyethylene) layer adjacent to a gelatin layer on the same side as the silver halide emulsion layers, and a fine hole-containing polyolefin (e.g., polypropylene, polyethylene) layer closer to the paper substrate. The density of the multi-layer or single-layer of polyolefin layer(s) existing between the paper substrate and photographic constituting layers is preferably in the range of 0.40 to 1.0 g/ml, more preferably in the range of 0.50 to 0.70 g/ml. Further, the thickness of the multi-layer or single-layer of polyolefin layer(s) existing between the paper substrate and photographic constituting layers is preferably in the range of 10 to 100 μm, more preferably in the range of 15 to 70 μm. Further, the ratio of thickness of the polyolefin layer(s) to the paper substrate is preferably in the range of 0.05 to 0.2, more preferably in the range 0.1 to 0.5.

Further, it is also preferable for enhancing rigidity (mechanical strength) of the reflective-support, by providing a polyolefin layer on the surface of the foregoing paper substrate opposite to the side of the photographic constituting layers, i.e., on the back surface of the paper substrate. In this case, it is preferable that the polyolefin layer on the back surface be polyethylene or polypropylene, the surface of which is matted, with the polypropylene being more preferable. The thickness of the polyolefin layer on the back surface is preferably in the range of 5 to 50 μm, more preferably in the range of 10 to 30 μm, and further the density thereof is preferably in the range of 0.7 to 1.1 g/ml. As to the reflective support for use in the present invention, preferable embodiments of the polyolefin layer provide on the paper substrate include those described in JP-A-10-333277, JP-A-10-333278, JP-A-11-52513, JP-A-11-65024, European Patent Nos. 0880065 and 0880066.

Further, it is preferred that the above-described water-proof resin layer contains a fluorescent whitening agent. Further, the fluorescent whitening agent also may be dispersed in a hydrophilic colloid layer of the light-sensitive material. Preferred fluorescent whitening agents that can be used, include benzoxazole series, coumarin series, and pyrazoline series compounds. Further, fluorescent whitening agents of benzoxazolylnaphthalene series and benzoxazolyl-stilbene series are more preferably used. The amount of the fluorescent whitening agent to be used is not particularly limited, and preferably in the range of 1 to 100 $mg/m^2$. When a fluorescent whitening agent is mixed with a water-proof resin, a mixing ratio of the fluorescent whitening agent to be used to the water-proof resin is preferably in the range of 0.0005 to 3% by weight, and more preferably in the range of 0.001 to 0.5% by weight of the resin.

Further, a transmissive type support or the foregoing reflective type support each having coated thereon a hydrophilic colloid layer containing a white pigment may be used as the reflective type support.

Furthermore, a reflective type support having a mirror plate reflective metal surface or a secondary diffusion reflective metal surface may be employed as the reflective type support.

As the support for use in the light-sensitive material of the present invention, a support of the white polyester type, or a support provided with a white pigment-containing layer on the same side as the silver halide emulsion layer, may be adopted for display use. Further, it is preferable for improving sharpness that an antihalation layer is provided on the silver halide emulsion layer side or the reverse side of the support. In particular, it is preferable that the transmission density of support is adjusted to the range of 0.35 to 0.8 so that a display may be enjoyed by means of both transmitted and reflected rays of light.

In the light-sensitive material of the present invention, in order to improve, e.g., sharpness of an image, a dye (particularly an oxonole-series dye) that can be discolored by processing, as described in European Patent No. 0337490 A2, pages 27 to 76, is preferably added to the hydrophilic colloid layer such that an optical reflection density at 680 nm in the light-sensitive material is 0.70 or more. It is also preferable to add 12% by weight or more (more preferably 14% by weight or more) of titanium oxide that is surface-treated with, for example, dihydric to tetrahydric alcohols (e.g., trimethylolethane) to a water-proof resin layer of the support.

The light-sensitive material of the present invention preferably contains, in their hydrophilic colloid layers, dyes (particularly oxonole dyes and cyanine dyes) that can be discolored by processing, as described in European Patent No. 0337490 A2, pages 27 to 76, in order to prevent irradiation or halation or enhance safelight safety (immunity). Further, dyes described in European Patent No. 0819977 are also preferably used in the present invention.

Among these water-soluble dyes, some deteriorate color separation or safelight safety when used in an increased amount. Preferable examples of the dye which can be used and which does not deteriorate color separation include water-soluble dyes described in JP-A-5-127324, JP-A-5-127325 and JP-A-5-216185.

In the present invention, it is possible to use a colored layer that can-be discolored during processing, in place of the water-soluble dye, or in combination with the water-soluble dye. The colored layer capable of being discolored with a processing to be used may contact with a light-sensitive emulsion layer directly, or indirectly through an interlayer containing an agent for preventing color-mixing during processing, such as hydroquinone and gelatin. The colored layer is preferably provided as a lower layer (closer to a support) with respect to the light-sensitive emulsion layer that develops the same primary color as the color of the colored layer. It is possible to provide colored layers independently, each corresponding to respective primary colors. Alternatively, only one layer selected from the above colored layers may be provided. In addition, it is possible to provide a colored layer subjected to coloring so as to match a plurality of primary-color regions. With respect to the optical reflection density of the colored layer, at the wavelength which provides the highest optical density in a range of wavelengths used for exposure (a visible light region from 400 nm to 700 nm for an ordinary printer exposure, and the wavelength of the light generated from the light source in the case of scanning exposure), the optical density is preferably within the range of 0.2 to 3.0, more preferably 0.5 to 2.5, and particularly preferably 0.8 to 2.0.

The colored layer described above may be formed by a known method. For example, there are a method in which a dye in a state of a dispersion of solid fine particles is incorporated in a hydrophilic colloid layer, as described in JP-A-2-282244, from page 3, upper right column to page 8, and JP-A-3-7931, from page 3, upper right column to page 11, left under column; a method in which an anionic dye is mordanted in a cationic polymer, a method in which a dye is adsorbed onto fine grains of silver halide or the like and fixed in the layer, and a method in which a colloidal silver is used, as described in JP-A-1-239544. As to a method of dispersing fine-powder of a dye in solid state, for example, JP-A-2-308244, pages 4 to 13 describes a method in which solid fine particles of dye which is at least substantially water-insoluble at the pH of 6 or less, but at least substantially water-soluble at the pH of 8 or more, are incorporated. The method of mordanting an anionic dye in a cationic polymer is described, for example, in JP-A-2-84637, pages 18 to 26. U.S. Pat. Nos. 2,688,601 and 3,459,563 disclose a method of preparing colloidal silver for use as a light absorber. Among these methods, preferred are the methods of incorporating fine particles of dye and of using colloidal silver.

Silver halide grains in the silver halide emulsion which can be used in the present invention, are preferably cubic or tetradecahedral crystal grains substantially having {100} planes (these grains may be rounded at the apexes thereof and further may have planes of higher order), or octahedral crystal grains. Alternatively, a silver halide emulsion in which the proportion of tabular grains having an aspect ratio of 2 or more and composed of {100} or {111} planes accounts for 50% or more in terms of the total projected area, can also be preferably used. The term "aspect ratio" refers to the value obtained by dividing the diameter of the circle having an area equivalent to the projected area of an individual grain by the thickness of the grain. In the present invention, cubic grains, or tabular grains having {100} planes as major faces, or tabular grains having {111} planes as major faces are preferably used.

As a silver halide emulsion which can be used in the present invention, for example, a silver chloride, silver bromide, silver iodobromide, or silver chloro(iodo)bromide emulsion may be used. It is preferable for a rapid processing to use a silver chloride or silver chlorobromide emulsion having a silver chloride content of 95 mole % or greater, more preferably a silver halide emulsion having a silver chloride content of 98 mole % or greater. Especially preferred of these silver halide emulsions are those containing silver chloride grains having a silver bromide localized phase on the surface thereof, since both high sensitivity and stabilization of photographic properties are attained.

The silver bromide localized phase is preferably formed by epitaxial growth of the localized phase having a total silver bromide content of at least 10 mole % in the silver bromide localized phase. A silver bromide content of the silver bromide localized phase is preferably in the range of 10 to 60 mole %, and most preferably in the range of 20 to 50 mole %. The silver bromide localized phase is preferably composed of silver having population of 0.1 to 5 mole %, more preferably 0.3 to 4 mole %, to the molar amount of entire silver which constitutes silver halide grains for use in the present invention. The silver bromide localized phase is preferably doped with complex ions of a metal of Group VIII in the periodic table, such as iridium (III) chloride, iridium (III) bromide, iridium (IV) chloride, sodium hexachloroiridate (III), potassium hexachloroiridate (IV), hexaammineiridium (IV) salts, trioxalatoiridium (III) salt, and trioxalatoiridium (IV) salt. The amount of these compounds to be added can be varied in a wide range depending on the purposes for use, and it is preferably in the range of $10^{-9}$ to $10^{-2}$ mole, per mole of silver halide.

In a silver halide emulsion for use in the present invention, various kinds of polyvalent metal ion impurities other than iridium may be incorporated, during grain formation or in the course of physical ripening of the emulsion. As for examples of the impurities to be used, salts or complex salts of metals of Group VIII of the periodic table, such as iron, ruthenium, osmium, rhenium, rhodium, cadmium, zinc, lead, copper and thallium, may be used in combination thereof. In the present invention, compounds of metals, such as iron, ruthenium, osmium and rhenium, which have at least four cyano ligands, are particularly preferred, since high-illumination-intensity sensitivity is further enhanced and latent-image sensitization is also inhibited. Iridium compounds provide an outstanding effect on the high-illumination intensity exposure suitability. The amount of these compounds to be added can be varied in a wide range depending on the purposes, and it is preferably in the range of $10^{-9}$ mole to $10^{-2}$ mole, per mole of silver halide.

The silver halide grains contained in the silver halide emulsion for use in the present invention have an average grain size (the grain size herein refers to the diameter of a circle equivalent to the projected area of an individual grain, and the number average is taken as the average grain size) of preferably from 0.1 μm to 2 μm.

With respect to the distribution of sizes of these grains, a so-called monodisperse emulsion having a variation coefficient (the value obtained by dividing the standard deviation of the grain size distribution by the average grain size) of 20% or less, more preferably 15% or less, and further preferably 10% or less, is preferred. For obtaining wide latitude, it is also preferred to blend the above-described monodisperse emulsions in the same layer or to form a multilayer structure by multilayer-coating of the monodisperse emulsions.

Various compounds or precursors thereof can be contained in the silver halide emulsion for use in the present invention to prevent fogging from occurring or to stabilize photographic performance during manufacture, storage or photographic processing of the photographic material. Specific examples of compounds useful for the above purposes are disclosed in JP-A-62-215272, pages 39 to 72, and they can be preferably used. In addition, 5-arylamino-1,2,3,4-thiatriazole compounds (in which the aryl residual group has at least one electron-attractive group), as disclosed in European Patent No. 0447647, are also preferably used.

Further, in the present invention, in order to enhance stability of the silver halide emulsion, it is preferable to use hydroxamic acid derivatives described in JP-A-11-109576, cyclic ketones having a double bond both ends of which are substituted with an amino group or a hydroxyl group, in adjacent to a carbonyl group, as described in JP-A-11-327094 (particularly those represented by formula (SI) and the descriptions of paragraph numbers 0036 to 0071 of JP-A-11-327094 can be incorporated herein by reference), catechols and hydroquinones each substituted with a sulfo group, as described in JP-A-11-143011 (e.g., 4,5-dihydroxy-1,3-benzenedisulfonic acid, 2,5-dihydroxy-1,4-benzenedisulfonic acid, 3,4-dihydroxybenzenesulfonic acid, 2,3-dihydroxybenzenesulfonic acid, 2,5-dihydroxybenzenesulfonic acid, 3,4,5-trihydroxybenzenesulfonic acid, and salts thereof), water-soluble reducing agents represented by any of formulae (I) to (III) of JP-A-11-102045, and hydroxylamines represented by the formula (A) in U.S. Pat. No. 5,556,741 (the descriptions of column 4, line 56 to column 11, line 22 in the U.S. Pat. No. 5,556,741 can be preferably applied to the present invention, and incorporated herein by reference).

Spectral sensitization is generally carried out, for the purpose of imparting spectral sensitivity in a desired light wavelength region to the light-sensitive emulsion in each layer of the photographic material of the present invention.

Spectral sensitizing dyes which are used in the photographic material of the present invention for spectral sensitization of blue, green and red light regions, include, for example, those disclosed by F. M. Harmer, in *Heterocyclic Compounds-Cyanine Dyes and Related Compounds*, John Wiley & Sons, New York, London (1964). Specific examples of the compounds and spectral sensitization processes that are preferably used in the present invention include those described in JP-A-62-215272, from page 22, right upper column to page 38. In addition, the spectral sensitizing dyes described in JP-A-3-123340 are very preferred as red-sensitive spectral sensitizing dyes for silver halide emulsion grains having a high silver chloride content from the viewpoint of stability, adsorption strength and the temperature dependency of exposure, and the like.

The amount of these spectral sensitizing dyes to be added can be varied in a wide range depending on the occasion, and it is preferably in the range of $0.5\times10^{-6}$ mole to $1.0\times10^{-2}$ mole, more preferably in the range of $1.0\times10^{-6}$ mole to $5.0\times10^{-3}$ mole, per mole of silver halide.

The silver halide emulsion that can be used in the present invention is generally chemically sensitized. Chemical sensitization can be performed by utilizing a sulfur sensitization, represented by the addition of an unstable sulfur compound, noble metal sensitization represented by gold sensitization, and reduction sensitization, each singly or in combination thereof. Compounds that are preferably used in chemical sensitization include those described in JP-A-62-215272, from page 18, right lower column to page 22, right upper column. Of these chemical sensitization, gold-sensitized silver halide emulsion are particularly preferred, since fluctuation in photographic properties which occurs when scanning exposure to laser beams or the like is conducted, can be further reduced by gold sensitization. In order to conduct gold sensitization, compounds such as chloroauric acid or a salt thereof, gold thiocyanates, gold thiosulfates, and colloidal gold sulfide may be used. The amount of these compounds to be added can be varied in a wide range depending on the occasion, and it is generally in the range of $5\times10^{-7}$ mole to $5\times10^{-3}$ mole, preferably in the range of $1.0\times10^{-6}$ mole to $1\times10^{-4}$ mole, per mole of silver halide. In the present invention, gold sensitization may be used in combination with other sensitizing methods, for example, sulfur sensitization, selenium sensitization, tellurium sensitization, reduction sensitization, or noble metal sensitization using a noble metal compound other than gold compounds.

The silver halide photographic light-sensitive material of the present invention can be used for a color negative film, a color positive film, a color reversal film, a color reversal photographic printing paper, a color photographic printing paper and the like. Among these materials, the light-sensitive material of the present invention is preferably used for a color photographic printing paper.

The color photographic printing paper preferably has at least one yellow color-forming silver halide emulsion layer, at least one magenta color-forming silver halide emulsion layer, and at least one cyan color-forming silver halide emulsion layer, on a support. Generally, these silver halide emulsion layers are in the order, from the support, of the yellow color-forming silver halide emulsion layer, the magenta color-forming silver halide emulsion layer and the cyan color-forming silver halide emulsion layer.

However, another layer arrangement which is different from the above, may be adopted.

When, for example, the coupler represented by formula (I) functions as a yellow coupler, a yellow coupler-containing silver halide emulsion layer may be disposed at any position on a support. However, in the case where silver halide tabular grains are contained in the yellow coupler-containing layer, it is preferable that the yellow coupler-containing layer is positioned more apart from a support than at least one of a magenta coupler-containing silver halide emulsion layer and a cyan coupler-containing silver halide emulsion layer. Further, it is preferable that the yellow coupler-containing silver halide emulsion layer is positioned most apart from a support of other silver halide emulsion layers, from the viewpoint of color-development acceleration, desilvering acceleration, and reduction in a residual color due to a sensitizing dye. Further, it is preferable that the cyan coupler-containing silver halide emulsion layer is disposed in the middle of other silver halide emulsion layers, from the viewpoint of reduction in a blix fading. On the other hand, it is preferable that the cyan coupler-containing silver halide emulsion layer is the lowest layer, from the viewpoint of reduction in a light fading. Further, each of a yellow-color-forming layer, a magenta-color-forming layer and a cyan-color-forming layer may be composed of two or three layers. It is also preferable that a color-forming layer is formed by disposing a silver halide emulsion-free layer containing a coupler in adjacent to a silver halide emulsion layer, as described in, for example, JP-A-4-75055, JP-A-9-114035, JP-A-10-246940, and U.S. Pat. No. 5,576,159.

Preferred examples of silver halide emulsions and other materials (additives or the like) for use in the present invention, photographic constitutional layers (arrangement of the layers or the like), and processing methods for processing the photographic materials and additives for processing are disclosed in JP-A-62-215272, JP-A-2-33144 and European Patent No. 0355660 A2. Particularly, those disclosed in European Patent No. 0355660 A2 are preferably used. Further, it is also preferred to use silver halide color photographic light-sensitive materials and processing methods therefor disclosed in, for example, JP-A-5-34889, JP-A-4-359249, JP-A-4-313753, JP-A-4-270344, JP-A-5-66527, JP-A-4-34548, JP-A-4-145433, JP-A-2-854, JP-A-1-158431, JP-A-2-90145, JP-A-3-194539, JP-A-2-93641 and European Patent Publication No. 0520457 A2.

In particular, as the above-described reflective support and silver halide emulsion, as well as the different kinds of metal ions to be doped in the silver halide grains, the storage stabilizers or antifogging agents of the silver halide emulsion, the methods of chemical sensitization (sensitizers), the methods of spectral sensitization (spectral sensitizing dyes), the cyan, magenta, and yellow couplers and the emulsifying and dispersing methods thereof, the dye stability-improving agents (stain inhibitors and discoloration inhibitors), the dyes (colored layers), the kinds of gelatin, the layer structure of the light-sensitive material, and the film pH of the light-sensitive material, those described in the patent publications as shown in the following Table 1 are preferably used in the present invention.

TABLE 1

| Element | JP-A-7-104448 | JP-A-7-77775 | JP-A-7-301895 |
|---|---|---|---|
| Reflective-type bases | Column 7, line 12 to Column 12, line 19 | Column 35, line 43 to Column 44, line 1 | Column 5, line 40 to Column 9, line 26 |
| Silver halide emulsions | Column 72, line 29 to Column 74, line 18 | Column 44, line 36 to Column 46, line 29 | Column 77, line 48 to Column 80, line 28 |
| Different metal ion species | Column 74, lines 19 to 44 | Column 46, line 30 to Column 47, line 5 | Column 80, line 29 to Column 81, line 6 |
| Storage | Column 75, lines 9 to | Column 47, lines 20 to | Column 18, line 11 to |

TABLE 1-continued

| Element | JP-A-7-104448 | JP-A-7-77775 | JP-A-7-301895 |
|---|---|---|---|
| stabilizers or antifoggants | 18 | 29 | Column 31, line 37 (Especially, mercaptoheterocyclic compounds) |
| Chemical sensitizing methods (Chemical sensitizers) | Column 74, line 45 to Column 75, line 6 | Column 47, lines 7 to 17 | Column 81, lines 9 to 17 |
| Spectrally sensitizing methods (Spectral sensitizers) | Column 75, line 19 to Column 76, line 45 | Column 47, line 30 to Column 49, line 6 | Column 81, line 21 to Column 82, line 48 |
| Cyan couplers | Column 12, line 20 to Column 39, line 49 | Column 62, line 50 to Column 63, line 16 | Column 88, line 49 to Column 89, line 16 |
| Yellow couplers | Column 87, line 40 to Column 88, line 3 | Column 63, lines 17 to 30 | Column 89, lines 17 to 30 |
| Magenta couplers | Column 88, lines 4 to 18 | Column 63, line 3 to Column 64, line 11 | Column 31, line 34 to Column 77, line 44 and column 88, lines 32 to 46 |
| Emulsifying and dispersing methods of couplers | Column 71, line 3 to Column 72, line 11 | Column 61, lines 36 to 49 | Column 87, lines 35 to 48 |
| Dye-image-preservability improving agents (antistaining agents) | Column 39, line 50 to Column 70, line 9 | Column 61, line 50 to Column 62, line 49 | Column 87, line 49 to Column 88, line 48 |
| Anti-fading agents | Column 70, line 10 to Column 71, line 2 | | |
| Dyes (coloring layers) | Column 77, line 42 to Column 78, line 41 | Column 7, line 14 to Column 19, line 42, and Column 50, line 3 to Column 51, line 14 | Column 9, line 27 to Column 18, line 10 |
| Gelatins | Column 78, lines 42 to 48 | Column 51, lines 15 to 20 | Column 83, lines 13 to 19 |
| Layer construction of light-sensitive materials | Column 39, lines 11 to 26 | Column 44, lines 2 to 35 | Column 31, line 38 to Column 32, line 33 |
| Film pH of light-sensitive materials | Column 72, lines 12 to 28 | | |
| Scanning exposure | Column 76, line 6 to Column 77, line 41 | Column 49, line 7 to Column 50, line 2 | Column 82, line 49 to Column 83, line 12 |
| Preservatives in developing solution | Column 88, line 19 to Column 89, line 22 | | |

As other cyan, magenta and yellow couplers which can be used in combination in the present invention, those disclosed in JP-A-62-215272, page 91, right upper column line 4 to page 121, left upper column line 6, JP-A-2-33144, page 3, right upper column line 14 to page 18, left upper column bottom line, and page 30, right upper column line 6 to page 35, right under column, line 11, European Patent No. 0355, 660 (A2), page 4 lines 15 to 27, page 5 line 30 to page 28 bottom line, page 45 lines 29 to 31, page 47 line 23 to page 63 line 50, are also advantageously used.

Further, it is preferred for the present invention to add compounds represented by formula (II) or (III) in WO 98/33760 or compounds represented by formula (D) described in JP-A-$10^{-221825.}$ In the silver halide photographic light-sensitive material of the present invention, the dye-forming coupler represented by formula (I) may be used alone or in combination with another coupler different from the coupler of formula (I). Other yellow couplers that can be used together with the coupler of the present invention (preferably, in the case that the coupler of the present invention is used as a yellow coupler) are as follows: the compounds described in the above-mentioned table, acylacetoamide yellow couplers having a 3-, 4, or 5-membered ring in an acyl group, as described in EP 0447969A1; malonedianilide yellow couplers having a cyclic structure, as described in EP 0482552A1; pyrrole-2 or 3-yl- or indole-2 or 3-yl-carbonylacetanilide couplers, as described in EP953870A1, EP953871A1, EP953872A1, EP953873A1, EP953874A1, EP953875A1, and the like; and acylacetoamide yellow couplers having a dioxane structure, as described in U.S. Pat. No. 5,118,599. Among these compounds, an acylacetoamide-type yellow coupler wherein its acyl group is a 1-alkylcyclopropane-1-carbonyl group, or a malonedianilide-type yellow coupler wherein one of its anilides constitutes an indoline ring is particularly preferred to use in combination with the coupler of the present invention.

The cyan coupler used in the present invention is preferably a phenol-series or naphthol-series cyan coupler, or a heterocyclic coupler.

The phenol coupler is preferably, for example, the cyan coupler represented by formula (ADF), as described in JP-A-10-333297, as well as any coupler in the above-mentioned table.

A 2,5-diacylaminophenol coupler, which is improved in hue and fastness of the resulting dye and which is described in U.S. Pat. No. 5,888,716, is preferably used.

As the heterocyclic coupler, the followings are preferred to use in combination with the coupler of the present invention: pyrroloazole-type cyan couplers described in EP 0488248 and EP0491197A1, and pyrazoloazole-type cyan couplers having a hydrogen bond group or an electron withdrawing group at its 6 position, as described in U.S. Pat. Nos. 4,873,183 and 4,916,051, particularly preferably pyrazoloazole-type cyan couplers having a carbamoyl group at its 6 position, as described in JP-A-8-171185, JP-A-8-311360 and JP-A-8-339060.

Among these cyan couplers, pyrroloazole-series cyan couplers represented by formula (I), as described in JP-A-11-282138, are particularly preferred. The descriptions in paragraph Nos. 0012 to 0059 of this publication, as well as the exemplified cyan couplers (1) to (47), can be applied to the present invention, and are preferably incorporated herein by reference.

In addition, the coupler of the present invention can also be used together with a diphenylimidazole-series cyan coupler described in JP-A-2-33144; a 3-hydroxypyridine-series cyan coupler (particularly a 2-equivalent coupler formed by allowing a coupler (42) of a 4-equivalent coupler to have a chlorine splitting-off group, and couplers (6) and (9), enumerated as specific examples are preferable) described in EP 0333185 A2; a cyclic active methylene-series cyan coupler (particularly couplers 3, 8, and 34 enumerated as specific examples are preferable) described in JP-A-64-32260; a pyrrolopyrozole-type cyan coupler described in European Patent No. 0456226 A1; or a pyrroloimidazole-type cyan coupler described in European Patent No. 0484909.

As the magenta coupler that can be used in the present invention, use can be made of a 5-pyrazolone-series magenta coupler or a pyrazoloazole-series magenta coupler, such as those described in the above-mentioned patent publications in the above Table. Among these, preferred are pyrazolotriazole couplers in which a secondary or tertiary alkyl group is directly bonded to the 2-, 3- or 6-position of the pyrazolotriazole ring, as described in JP-A-61-65245; pyrazoloazole couplers having a sulfonamido group in its molecule, as described in JP-A-61-65246; pyrazoloazole couplers having an alkoxyphenylsulfonamido ballasting group, as described in JP-A-61-147254; and pyrazoloazole couplers having an alkoxy or aryloxy group on its 6-position, as described in European Patent Nos. 0226849 A2 and 0294785 A, in view of the hue and stability of image to be formed therefrom and color-forming property of the couplers.

Particularly as the magenta coupler, pyrazoloazole couplers represented by formula (M-I), as described in JP-A-8-122984, are preferred. The descriptions of paragraph Nos. 0009 to 0026 of the patent publication can be entirely applied to the present invention and therefore are incorporated herein by reference.

In addition, pyrazoloazole couplers having a steric hindrance group at both the 3- and 6-positions, as described in European Patent Nos. 845384 and 884640, are also preferably used.

It is preferred that magenta or cyan couplers, as well as the (yellow) coupler of the present invention, are also pregnated into a loadable latex polymer (as described, for example, in U.S. Pat. No. 4,203,716) in the presence (or absence) of the high-boiling-point organic solvent described in the foregoing table, or they are dissolved in the presence (or absence) of the foregoing high-boiling-point organic solvent with a polymer insoluble in water but soluble in an organic solvent, and then emulsified and dispersed into an aqueous hydrophilic colloid solution.

The water-insoluble but organic solvent-soluble polymers that can be preferably used, include the homo-polymers and co-polymers disclosed in U.S. Pat. No. 4,857,449, from column 7 to column 15 and WO 88/00723, from page 12 to page 30. The use of methacrylate-series or acrylamide-series polymers, especially acrylamide-series polymers are more preferable in view of color-image stabilization and the like.

To suppress Blix discoloration (leuco dye reciprocity failure) by a bleaching solution or bleach-fixing solution, it is preferred to use a polymer described in JP-A-8-62797, JP-A-9-17240 and JP-A-9-329861, in the hydrophilic colloid layer.

In the present invention, known color mixing-inhibitors may be used. Among these compounds, those described in the following patent publications are preferred.

For example, high molecular weight redox compounds described in JP-A-5-333501; phenidone- or hydrazine-series compounds as described in, for example, WO 98/33760 and U.S. Pat. No. 4,923,787; and white couplers as described in, for example, JP-A-5-249637, JP-A-10-282615 and German Patent No. 1962914 A1, may be used. Further, in order to accelerate developing speed by increasing the pH of a developing solution, redox compounds described in, for example, German Patent Nos. 19,618,786 A1 and 19,806,846 A1, European Patent Nos. 0,839,623 A1 and 0,842,975 A1, and French Patent No. 2,760,460 A1, are also preferably used.

In the present invention, as an ultraviolet ray absorbent, it is preferred to use compounds having a high molar extinction coefficient. Examples of these compounds include those having a triazine skeleton. Among these compounds, use can be made of those described, for example, in JP-A-46-3335, JP-A-55-152776, JP-A-5-197074, JP-A-5-232630, JP-A-5-307232, JP-A-6-211813, JP-A-8-53427, JP-A-8-234364, JP-A-8-239368, JP-A-9-31067, JP-A-10-115898, JP-A-10-147577, JP-A-10-182621, JP-T-8-501291 ("JP-T" means searched and published International patent application), European Patent No. 0,711,804 A1 and German Patent No. 19,739,797A.

In the present invention, examples of a decoloration inhibitor (anti-fading agent), a hue adjusting agent, and the like other than those described in the above Table, include vinyl compounds represented by formula (II), aniline derivatives represented by formula (III) having an oxygen-nitrogen bond or substituted with an alkoxy group, non-diffusible phenydone derivatives represented by formula (IV), nondiffusion carboxylic acids represented by formula (V), non-diffusible arylcarbamoyl derivatives represented by formula (VI), arylamide derivatives represented by formula (VII), and cyclic imide derivatives represented by formula (VIII), each of which are described in JP-A-11-258748, and all of them can be preferably used.

As the binder or protective colloid that can be used in the light-sensitive material of the present invention, gelatin is used advantageously, but another hydrophilic colloid can be used singly or in combination with gelatin. It is preferable for the gelatin for use in the present invention that the content of heavy metals, such as Fe, Cu, Zn and Mn, as impurities therein, is reduced to 5 ppm or below, more preferably 3 ppm or below.

Further, the amount of calcium contained in the light-sensitive material is preferably 20 $mg/m^2$ or less, more preferably 10 $mg/m^2$ or less, and most preferably 5 $mg/m^2$ or less.

In the present invention, it is preferred to add an antibacterial (fungi-preventing) agent and antimold agent, as described in JP-A-63-271247, in order to destroy various kinds of molds and bacteria which propagate in a hydrophilic colloid layer and deteriorate the image.

Further, the pH of the film of the light-sensitive material is preferably in the range of 4.0 to 7.0, more preferably in the range of 4.0 to 6.5.

The light-sensitive material of the present invention can preferably be used, in addition to the printing system using a general negative printer, in a scanning exposure system using a cathode ray tube (CRT).

The cathode ray tube exposure apparatus is simpler and more compact, and therefore less expensive than a laser-emitting apparatus. Further, optical axis and color (hue) can easily be adjusted.

In a cathode ray tube that is used for image-wise exposure, various light-emitting substances which emit a light in the spectral region, are used as occasion demands. For example, any one of red-light-emitting substances, green-light-emitting substances, blue-light-emitting substances, or a mixture of two or more of these light-emitting substances may be used. The spectral regions are not limited to the above red, green and blue, and fluorophoroes which can emit a light in a region of yellow, orange, purple or infrared can be used. Particularly, a cathode ray tube that emits a white light by means of a mixture of these light-emitting substances is often used.

In the case where the light-sensitive material has a plurality of light-sensitive layers each having different spectral sensitivity distribution from each other and also the cathode ray tube has fluorescent substances which emit light in a plurality of spectral regions, exposure to a plurality of colors may be carried out at the same time. Namely, color image signals may be input into a cathode ray tube, to allow light to be emitted from the surface of the tube. Alternatively, a method in which an image signal of each of colors is successively input and light of each of colors is emitted in order, and then exposure is carried out through a film capable of cutting a color other than the emitted color, i.e., a surface successive exposure, may be used. Generally, among these methods the surface successive exposure is preferred from the viewpoint of high quality enhancement, because a cathode ray tube having high resolution can be used.

The light-sensitive material of the present invention can preferably be used in the digital scanning exposure system using monochromatic high density light, such as a gas laser, a light-emitting diode, a semiconductor laser, a second harmonic generation light source (SHG) comprising a combination of nonlinear optical crystal with a semiconductor or a solid state laser using a semiconductor laser as an excitation light source. It is preferred to use a semiconductor laser, or a second harmonic generation light source (SHG) comprising a combination of nonlinear optical crystal with a solid state laser or a semiconductor laser, to make a system more compact and inexpensive. In particular, to design a compact and inexpensive apparatus having a longer duration of life and high stability, use of a semiconductor laser is preferable; and it is preferred that at least one of exposure light sources should be a semiconductor laser.

When such a scanning exposure light source is used, the maximum spectral sensitivity wavelength of the light-sensitive material of the present invention can be arbitrarily set up in accordance with the wavelength of a scanning exposure light source to be used. Since oscillation wavelength of a laser can be made half, using a SHG light source obtainable by a combination of a nonlinear optical crystal with a semiconductor laser or a solid state laser using a semiconductor as an excitation light source, blue light and green light can be obtained. Accordingly, it is possible to have the spectral sensitivity maximum of a photographic material in normal three wavelength regions of blue, green and red.

The exposure time in such a scanning exposure is defined as the time necessary to expose the size of the picture element (pixel) with the density of the picture element being 400 dip, and preferred exposure time is $10^{-4}$ sec or less and more preferably $10^{-6}$ sec or less.

The scanning exposure system that can preferably be used for the present invention is described in detail in the patent publications as shown in the above table.

With respect to the processing of the photographic material of the present invention, processing materials and processing methods, as disclosed in JP-A-2-207250, from page 26, right under column, line 1 to page 34, right upper column, line 9, and JP-A-4-97355, from page 5, left upper column, line 17 to page 18, right under column, line 20, can be preferably applied. Further, as preservatives which are used in the developing solution, compounds described in the patent publications as shown in the above table can be preferably used.

The present invention is preferably applied to a light-sensitive material having rapid processing suitability.

The term "color-developing time" as used herein refers to a period of time required from the beginning of dipping a light-sensitive material into a color-developing solution until the light-sensitive material is dipped into a blix solution in the subsequent processing step. In the case where a processing is carried out using, for example, an autoprocessor, the color-developing time is the sum total of a time in which a light-sensitive material has been dipped in a color-developing solution (so-called "time in the solution") and a time in which the light-sensitive material has been conveyed in air toward a bleach-fixing bath in the step subsequent to color development (so-called "time in the air"). Likewise, the term "blix time" as used herein refers to a period of time required from the beginning of dipping a light-sensitive material into a blix solution until the light-sensitive material is dipped into a washing bath or a stabilizing bath in the subsequent processing step. Further, the term "washing or stabilizing time" as used herein refers to a period of time required from the beginning of dipping a light-sensitive material into a washing solution or a stabilizing solution until the end of the dipping toward a drying step (so-called "time in the solution").

In the present invention, the color-developing time is preferably 60 sec or less, more preferably from 50 sec to 6 sec, further preferably from 30 sec to 6 sec. Likewise, the blix time is preferably 60 sec or less, more preferably from 50 sec to 6 sec, further preferably from 30 sec to 6 sec. Further, the washing or stabilizing time is preferably 150 sec or less, more preferably from 130 sec to 6 sec.

Examples of a development method applicable to the photographic material of the present invention after exposure, include a conventional wet system, such as a development method using a developing solution containing an alkali agent and a developing agent, and a development method wherein a developing agent is incorporated in the photographic material and an activator solution, e.g., a developing agent-free alkaline solution is employed for the development, as well as a heat development system using no processing solution. In particular, the activator method using a developing agent-free alkaline solution is preferred over the other methods, because the processing solution contains no developing agent, thereby it enables easy management and handling of the processing solution, and reduction in waste disposal load to make for environmental preservation.

The preferable developing agents or their precursors to be incorporated in the photographic materials in the case of adopting the activator method include the hydrazine compounds described in, for example, JP-A-8-234388, JP-A-9-152686, JP-A-9-152693, JP-A-9-211814 and JP-A-9-160193.

Further, the processing method in which the photographic material reduced in the amount of silver to be applied undergoes the image amplification processing using hydrogen peroxide (intensification processing), can be employed preferably. In particular, it is preferably to apply this processing method to the activator method. Specifically, the image-forming methods utilizing an activator solution containing hydrogen peroxide, as disclosed in JP-A-8-297354 and JP-A-9-152695 can be preferably used.

The processing with an activator solution is generally followed by a desilvering step in the activator method, but the desilvering step can be omitted in the case of applying the image amplification processing method to photographic materials of a low silver amount. In such a case, washing or stabilization processing can follow the processing with an activator solution to result in simplification of the processing process. On the other hand, when the system of reading the image information from photographic materials by means of a scanner or the like is employed, the processing form requiring no desilvering step can be applied, even if the photographic materials are those of a high silver amount, such as photographic materials for shooting.

The activator solution, desilvering solution (bleach-fixing solution), washing solution and stabilizing solution for use in the present invention can contain known ingredients and can be used in conventional manners. Preferably, those described in *Research Disclosure,* Item 36544, pp. 536–541 (September 1994), and JP-A-8-234388 can be used in the present invention.

It is preferred to use a band stop filter, as described in U.S. Pat. No. 4,880,726, when the photographic material of the present invention is subjected to exposure with a printer. Color mixing of light can be excluded and color reproducibility is remarkably improved by the above means.

In the present invention, a yellow microdot pattern may be previously formed by pre-exposure before giving an image information, to thereby perform copy restraint, as described in European Patent Nos. 0789270 A1 and 0789480 A1.

The light-sensitive material of the present invention can be preferably used as a light-sensitive material for the advanced photo-system, which has a magnetic recording layer. The light-sensitive material of the present invention can be preferably used in a system wherein a small amount of water is used to perform heat-development, or in a complete dry system wherein no water is used to perform heat-development. Detailed descriptions on these systems are found, for example, in JP-A-6-35118, JP-A-6-17528, JP-A-56-146133, JP-A-60-119557, and JP-A-1-161236.

In the present invention, the wording "a silver halide photographic light-sensitive material" means to include not only a light-sensitive material for forming a color image but also a light-sensitive material for forming a monotone image, an example of which is a black and white image.

In case where the coupler of the present invention is applied to a color paper, light-sensitive material and the like described in JP-A-11-7109, particularly descriptions in paragraph numbers 0071 to 0087 in JP-A-11-7109 are preferable, and therefore the above descriptions in JP-A-11-7109 are incorporated herein by reference.

In case where the coupler of the present invention is applied to a color negative film, the descriptions at paragraph Nos. 0115 to 0217 of the specification of JP-A-11-305396 can be preferably applied thereto, and therefore incorporated herein by reference.

In case where the coupler of the present invention is applied to a color reversal film, the descriptions at paragraph Nos. 0018 to 0021 of the specification of JP-A-11-84601 can be preferably applied thereto, and therefore incorporated herein by reference.

(Method for Producing an Azomethine Dye)

The method for producing an azomethine dye according to the present invention is characterized by using a compound represented by the formula (I), that is, the dye-forming coupler, and the production method preferably uses a compound represented by the formula (IA).

The compound represented by formula (IA) is useful for synthesizing an azomethine dye wherein an aromatic ring is directly bonded thereto.

More specifically, by coupling reaction of the compound represented by formula (IA) with an oxidized product of a p-phenylenediamine derivative, particularly preferably an N,N-disubstituted-p-phenylenediamine derivative, an azomethine dye wherein an aromatic ring is directly bonded thereto can easily be obtained.

As described below, from the compound represented by formula (IA) and a compound represented by the following formula (A), a dye represented by the following formula (D) can easily be produced in one step.

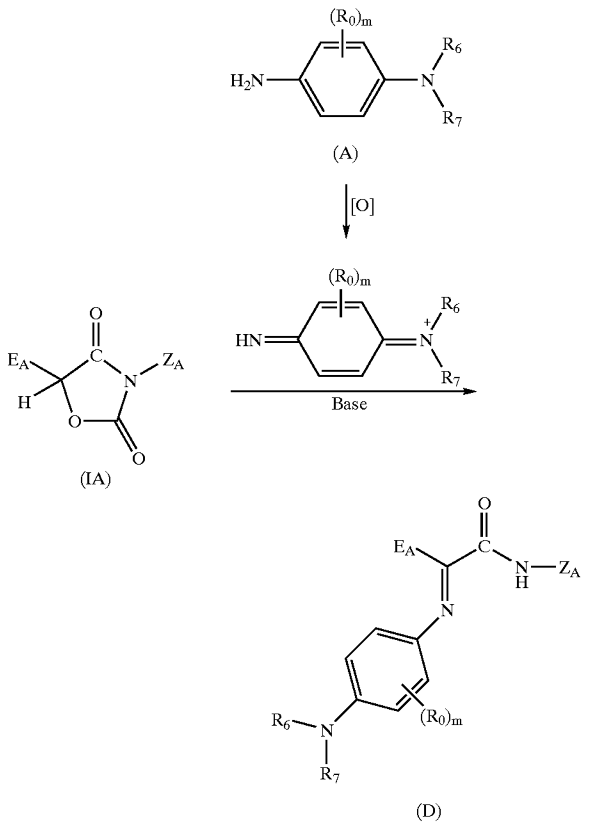

(A) (IA) (D)

In the above-mentioned reaction, a hydrogen atom is first dissociated from the compound represented by formula (IA). This portion undergoes coupling-reaction with an oxidized product, which is resulted from oxidization of the compound represented by formula (A) with an oxidizer. Thereafter, the $CO_2$ moiety is eliminated therefrom, to form the azomethine dye represented by formula (D). The above-mentioned reaction used in the method for producing an azomethine dye of the present invention is characterized in that the compound represented by formula (IA) reacts with the oxidized product of the compound represented by formula (A), to cleave the 5-membered ring moiety, whereby $CO_2$ eliminates from an nitrogen atom. With respect to an obtainable dye represented by formula (D), its performance as a dye, which is a target of the present invention, is remarkably improved by the elimination of $CO_2$ from the nitrogen atom.

In the formula (D), $R_0$, $R_6$ and $R_7$ each independently represent a substituent, and m is an integer of 0, or 1 to 4.

Examples of the substituent represented by $R_0$, $R_6$ and $R_7$ are the same as described as the examples of the substituent that the aryl or heterocyclic group represented by $E_A$ or $Z_A$ in the formula (IA) may have. $R_0$ is preferably a substituted or unsubstituted alkyl group having 1 to 30 carbon atoms, a substituted or unsubstituted alkenyl group having 1 to 30 carbon atoms, a substituted or unsubstituted aryl group having 6 to 30 carbon atoms, a substituted or unsubstituted alkoxy group having 1 to 30 carbon atoms, or a halogen atom. $R_6$ and $R_7$ each are preferably a substituted or unsubstituted alkyl group having 1 to 30 carbon atoms, or a substituted or unsubstituted aryl group having 6 to 30 carbon atoms m is preferably 0 or 1.

More preferably, $R_0$ is an unsubstituted alkyl group having 1 to 4 carbon atoms, and $R_6$ and $R_7$ each are a substituted or unsubstituted alkyl group having 1 to 4 carbon atoms. The substituent thereof is preferably a hydroxyl group or a methanesulfonylamino group.

Particularly preferably, $R_0$ is a methyl group, $R_6$ is an ethyl group, and $R_7$ is a β-methanesulfonamidoethyl group or a β-hydroxyethyl group.

The azomethine dye represented by formula (D) can easily be synthesized, for example, by dissolving the dye-forming coupler represented by formula (IA) and a p-phenylenediamine derivative represented by the formula (A) in a solvent, and adding an oxidizer to the resultant solution, as described in the following examples. $R_0$, $R_6$ and $R_7$ in the formula (A) have the same meanings as $R_0$, $R_6$ and $R_7$ in the formula (D).

The solvent that can be used in the production process may be polar or nonpolar, if the compound represented by formula (IA) and the compound represented by formula (A) can be dissolved in this solvent. Examples thereof include chloroform, ethyl acetate, ethanol, and N,N-dimethylformamide. The amount to be used of the compound represented by formula (A) to the compound represented by formula (IA) is generally from 0.1 to 10, preferably from 0.5 to 5, and more preferably from 0.8 to 1.5, in terms of molar ratio. As a base, use can be made, for example, of sodium carbonate, potassium carbonate, sodium hydrogencarbonate, potassium hydrogencarbonate, sodium hydroxide, and potassium hydroxide. Regarding the amount of the base to be used, the amount necessary for dissociating the compound represented by formula (IA) is used. When the compound represented by formula (A) is in a salt form, the amount necessary for further removing this base is also used. As the oxidizer, any oxidizer may be used. Examples thereof include persulfates, manganese dioxide, silver halides, and ferric chloride. The reaction temperature is generally in the range from −10 to 100° C., preferably from room temperature to 80° C., and more preferably from room temperature to 50° C.

The following will illustrate examples of the dye represented by formula (D), which can be produced by the azomethine dye-producing method of the present invention, but the present invention is not limited to these specific examples.

(D-1)

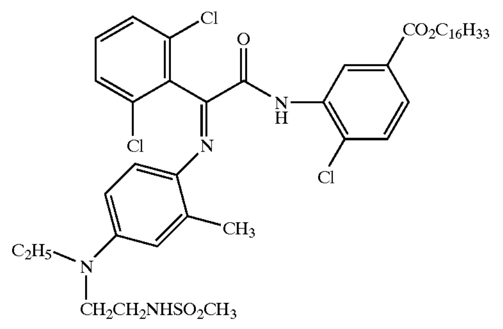

(D-2)

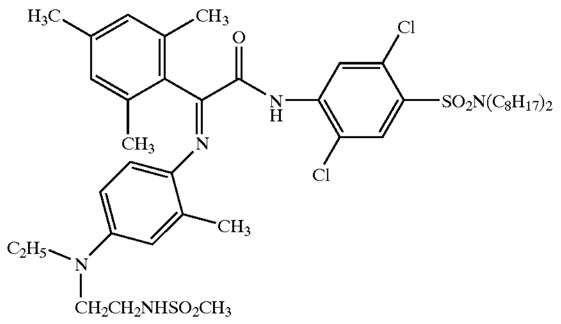

(D-3)

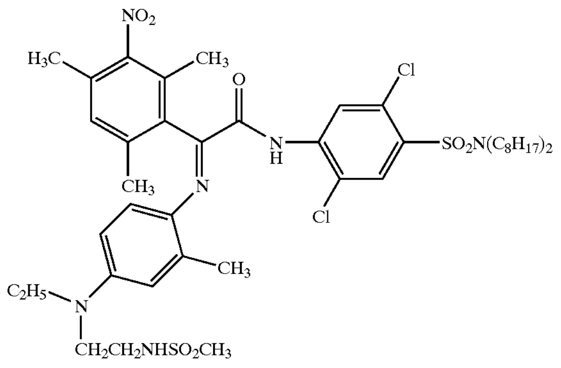

(D-4)

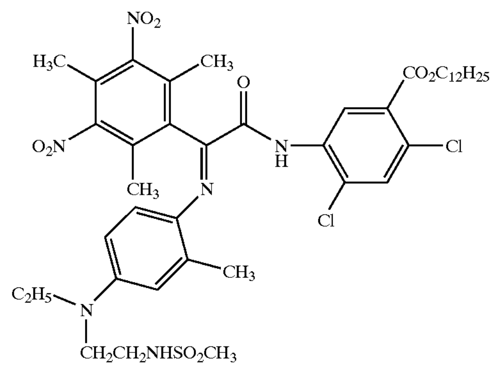

-continued
(D-5)
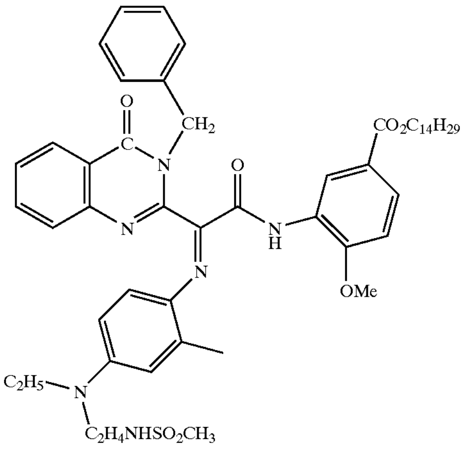
(D-6)
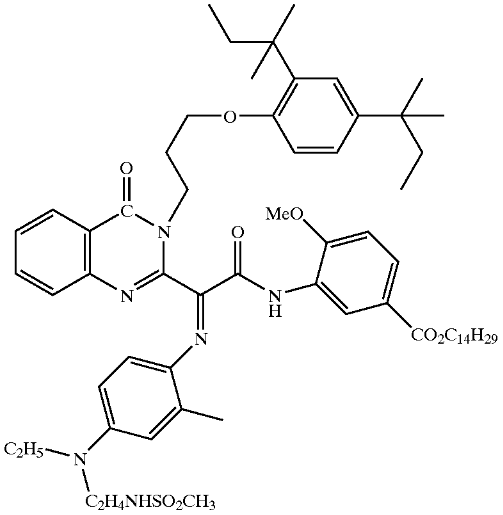
(D-7)
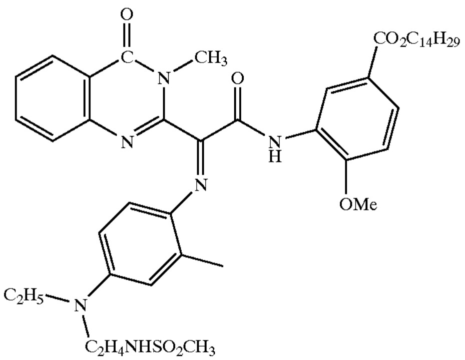
-continued
(D-8)
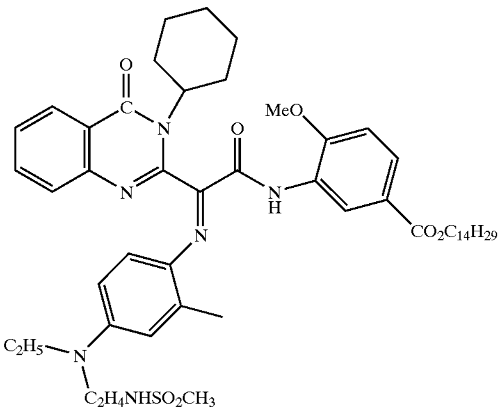
(D-9)
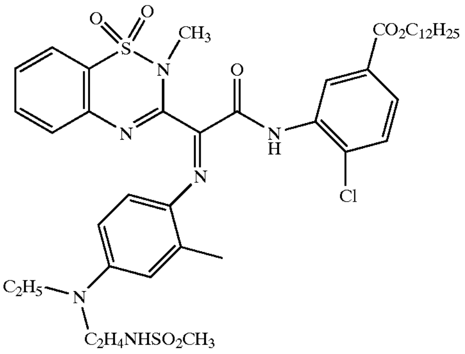
(D-10)
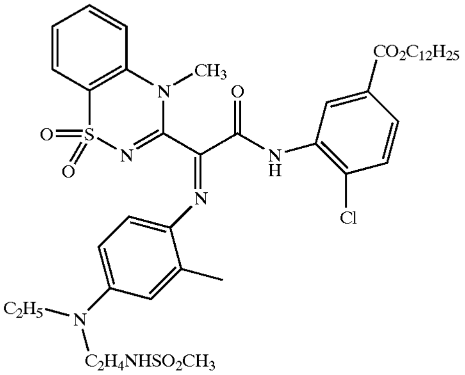
(D-11)
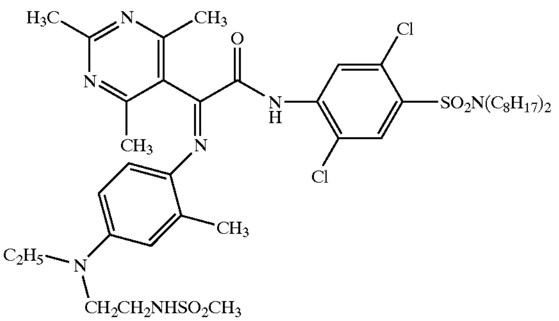

-continued
(D-12)
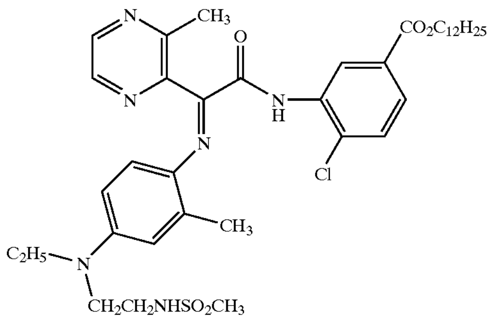
(D-13)
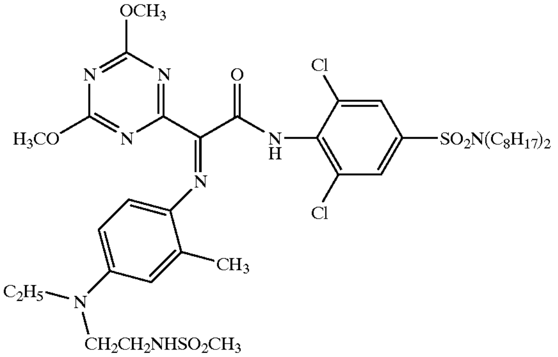
(D-14)
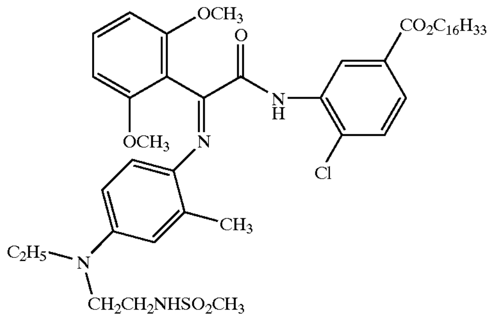
(D-15)
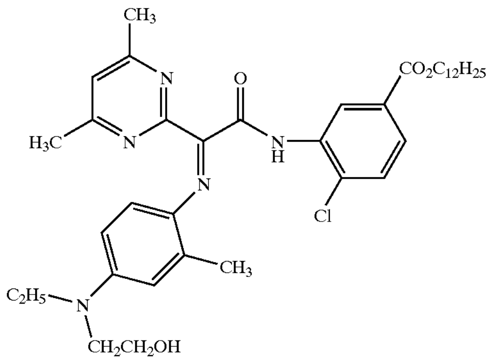
-continued
(D-16)
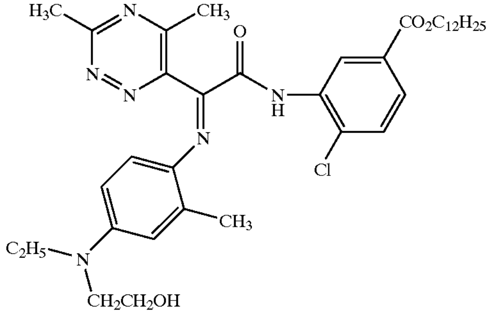
(D-17)
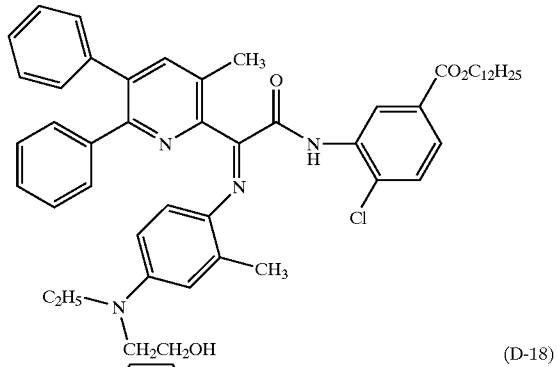
(D-18)
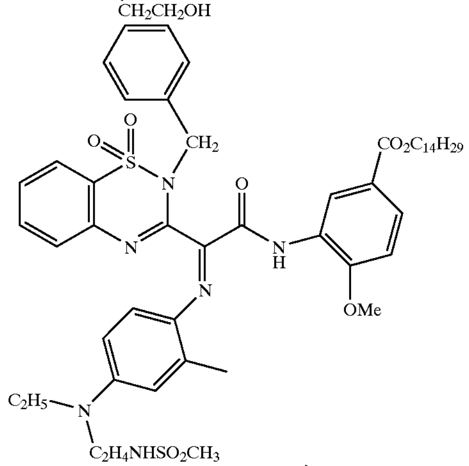
(D-19)
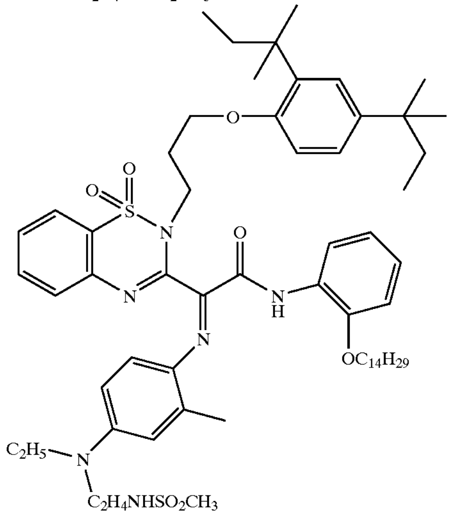

-continued (D-20)

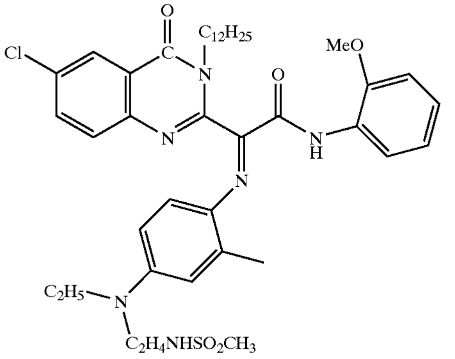

(D-21)

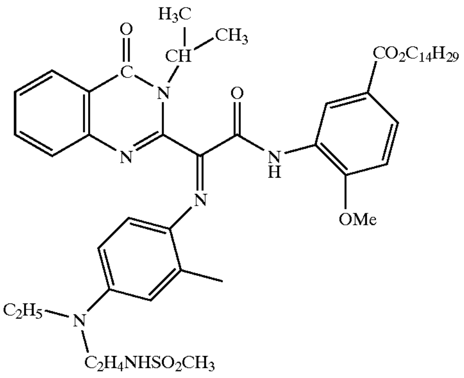

(D-22)

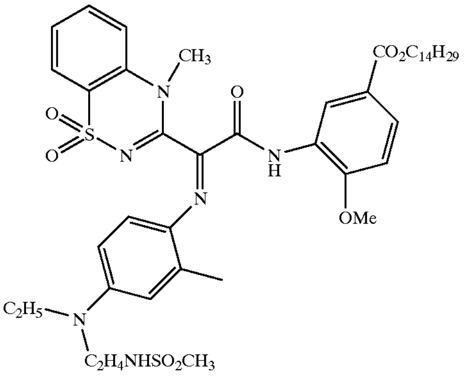

(D-23)

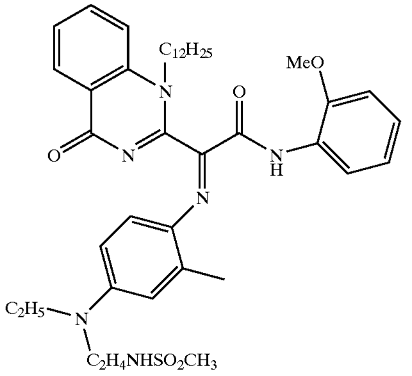

-continued (D-24)

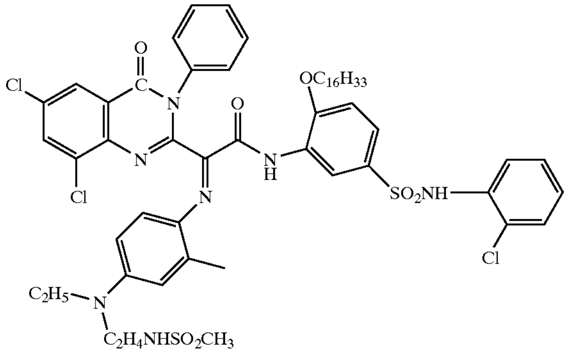

The dye-forming coupler of the present invention can give a dye excellent in hue, quite large in molecular extinction coefficient, and excellent in storage stability. Further, the dye-forming coupler of the present invention can give a dye excellent in color-forming property. The dye-forming coupler of the present invention is particularly preferable as a yellow coupler, and the dye-forming coupler can be produced at a low cost in a short/simple production process.

The silver halide photographic light-sensitive material of the present invention is excellent in color reproduction and sharpness, and also in color-image fastness. Further, the light-sensitive material of the present invention can also attain quite high color density.

Further, according to the method of the present invention for producing an azomethine dye, it is possible to simply produce the azomethine dye quite high in molecular extinction coefficient, and excellent in hue and storability.

The present invention will now be described in more detail with reference to the following examples, but the invention is not limited to those.

EXAMPLE

Comparative Example 1

1. Preparation of a Dye for Comparison (CD-1)

To a mixture of 0.85 g of the following coupler for comparison (C-1), 0.80 g of N-ethyl-N-(β -methanesulfoneamidoethyl)-3-methyl-4-aminoaniline sulfate, 3.75 g of sodium carbonate, 60 ml of THF and 50 ml of water, was gradually added a solution of 1.45 g of ammonium persulfate dissolved in 10 ml of water, at room temperature under stirring. The reaction liquid was stirred for 1 hour and then the THF phase was separated. The THF phase was purified by silica gel chromatography, to give a dye for comparison (CD-1), which was the following yellow azomethine dye for comparison.

Coupler for Comparison (C-1)

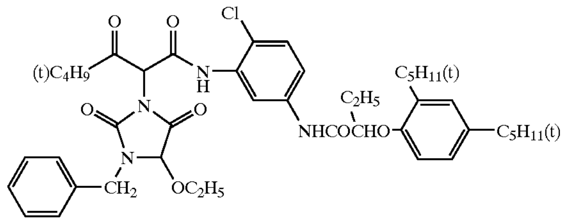

Dye for Comparison (CD-1)

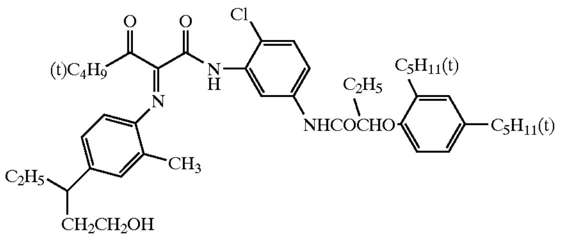

Examples 1 to 10

1. Preparation of Dyes (D-1) to (D-10)

The dyes (D-1) to (D-10) were synthesized in the same manner as in Comparative Example 1, except that in "1. Preparation of a dye for comparison (CD-1)" in Comparative Example 1, the above-mentioned exemplified couplers (7), (10), (16), (18), (50), (51), (53), (73), (83) and (84) in the present invention were used, respectively, instead of the coupler for comparison (C-1), to give the following dye D-1 wherein the coupler (7) was used, dye D-2 wherein the coupler (10) was used, dye D-3 wherein the coupler (16) was used, dye D-4 wherein the coupler (18) was used, dye D-5 wherein the coupler (50) was used, dye D-6 wherein the coupler (51) was used, dye D-7 wherein the coupler (53) was used, dye D-8 wherein the coupler (73) was used, dye D-9 wherein the coupler (83) was used, and dye D-10 wherein the coupler (84) was used, each of which was the azomethine dye obtained from the dye-forming coupler of the present invention.

(D-1)

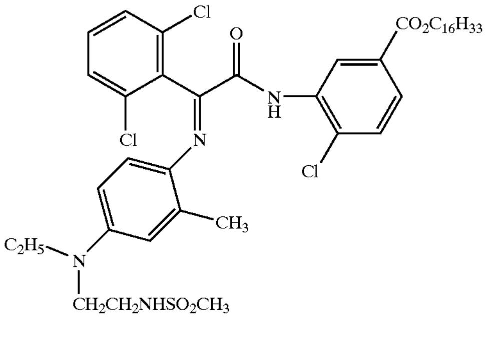

(D-2)

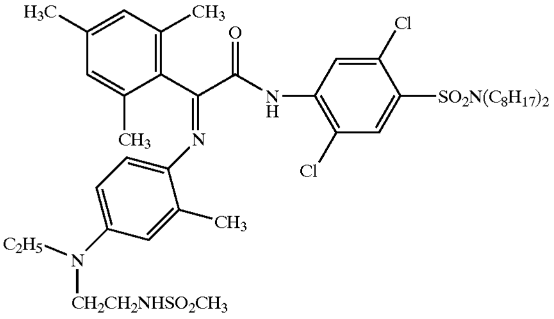

-continued (D-3)

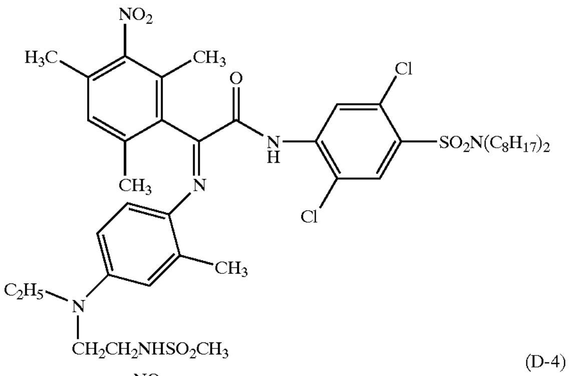

(D-4)

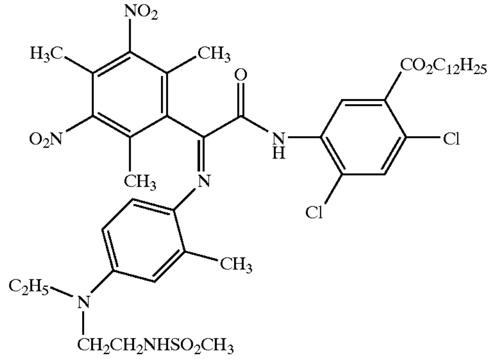

(D-5)

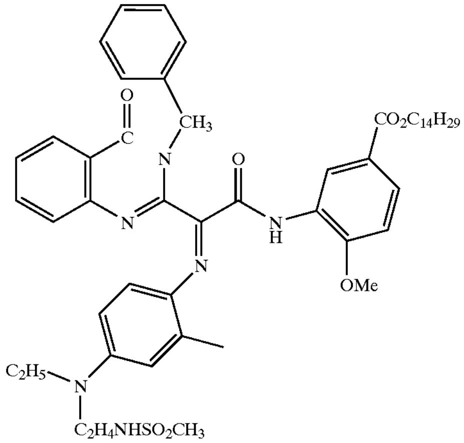

(D-6)

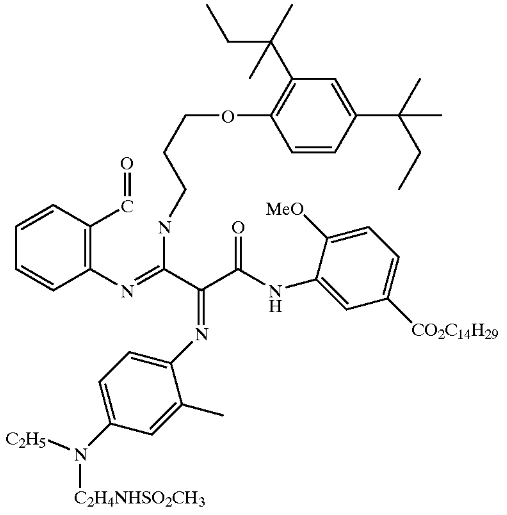

-continued (D-7)

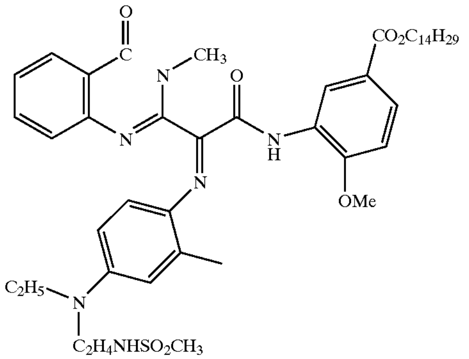

(D-8)

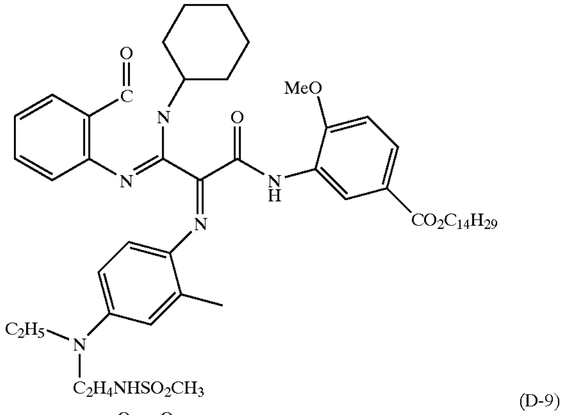

(D-9)

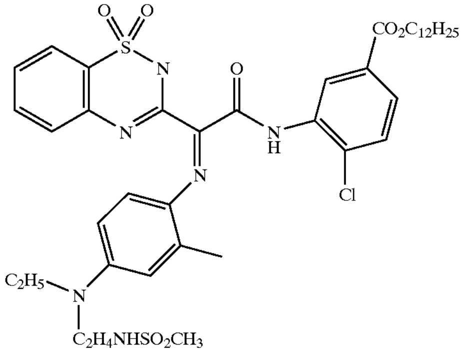

(D-10)

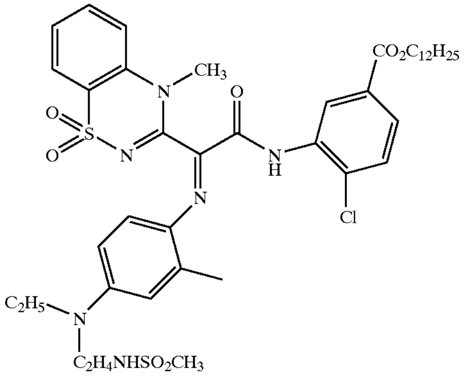

<Measurement of Molecular Extinction Coefficient>

With regard to each of the dye for comparison (CD-1) and the dyes (D-1) to (D-10) obtained in the above Comparative Example 1 and Examples 1 to 10, the molecular extinction coefficient was measured in the following manner.

1.5 mg of any one of the dye for comparison (CD-1) and the dyes (D-1) to (D-10) was precisely weighted in a 100 ml measuring flask, and then 100 ml of ethyl acetate was added thereto, to dissolve the dye, then the resultant solution was diluted with ethyl acetate, to prepare a sample solution 101 wherein the dye for comparison (CD-1) was used, a sample solution 102 wherein the dye (D-1) was used, a sample solution 103 wherein the dye (D-2) was used, a sample solution 104 wherein the dye (D-3) was used, a sample solution 105 wherein the dye (D-4) was used, a sample solution 106 wherein the dye (D-5) was used, a sample solution 107 wherein the dye (D-6) was used, a sample solution 108 wherein the dye (D-7) was used, a sample solution 109 wherein the dye (D-8) was used, a sample solution 110 wherein the dye (D-9) was used, and a sample solution 111 wherein the dye (D-10) was used, respectively.

Each of the resultant sample solutions 101 to 111 was put in a quartz cell of 1-cm thickness, and then the visible absorption spectrum thereof was measured with an ultraviolet/visible spectrophotometer made by Shimadzu Corp, to calculate the molecular extinction coefficient thereof. The obtained molecular extinction coefficients are shown in Table 2.

TABLE 2

| | Sample Solution No. | Kind of Coupler | Kind of dye | Molecular extinction coefficient |
|---|---|---|---|---|
| Comparative Example 1 | 101 | Coupler for comparison (C-1) | CD-1 | $1.65 \times 10^4$ |
| Example 1 | 102 | Coupler(7) | D-1 | $2.11 \times 10^4$ |
| Example 2 | 103 | Coupler(10) | D-2 | $2.44 \times 10^4$ |
| Example 3 | 104 | Coupler(16) | D-3 | $2.68 \times 10^4$ |
| Example 4 | 105 | Coupler(18) | D-4 | $2.72 \times 10^4$ |
| Example 5 | 106 | Coupler(50) | D-5 | $2.69 \times 10^4$ |
| Example 6 | 107 | Coupler(51) | D-6 | $2.85 \times 10^4$ |
| Example 7 | 108 | Coupler(53) | D-7 | $2.61 \times 10^4$ |
| Example 8 | 109 | Coupler(73) | D-8 | $2.46 \times 10^4$ |
| Example 9 | 110 | Coupler(83) | D-9 | $2.92 \times 10^4$ |
| Example 10 | 111 | Coupler(84) | D-10 | $3.07 \times 10^4$ |

It can be understood from the results in Table 2 that the dyes obtained from the dye-forming coupler of the present invention have a quite larger molecular extinction coefficient than the dye obtainable from the dye-forming coupler for comparison. Since the molecular extinction coefficient of the dye obtainable from the dye-forming coupler of the present invention is so large, a thinner layer containing such a dye-forming coupler makes it possible to exhibit the same level of density as in the conventional technique. This means that color reproduction and sharpness of an image obtainable from a silver halide photographic light-sensitive material in which said coupler of the present invention is used are highly improved.

<Acid-induced Fading Test of Dyes>

Each of the dye for comparison (CD-1) and the dyes (D-1) to (D-10) obtained in the above Comparative Example 1 and Examples 1 to 10 was subjected to an acid-induced fading test in the following manner.

Into 15 ml of NMP (1-methyl-2-pyrrolidinone, for peptide synthesis, purity: 99%), was dissolved 1.0 mg of any one of the dye for comparison (CD-1) or the dyes (D-1) to (D-10), to prepare a sample solution 201 wherein the dye for comparison (CD-1) was used, a sample solution 202 wherein the dye (D-1) was used, a sample solution 203 wherein the dye (D-2) was used, a sample solution 204 wherein the dye (D-3) was used, a sample solution 205 wherein the dye (D-4) was used, a sample solution 206 wherein the dye (D-5) was used, a sample solution 207 wherein the dye (D-6) was used, a sample solution 208 wherein the dye (D-7) was used, a sample solution 209 wherein the dye (D-8) was used, a sample solution 210 wherein the dye (D-9) was used, and a sample solution 211 wherein the dye (D-10) was used, respectively.

Phosphoric acid was added to a solution prepared by mixing 0.49 g of boric acid, 8 ml of a 1-N aqueous acetic acid solution, and 16 ml of a 1-N aqueous phosphoric acid solution in a 200-ml measuring flask (Britton-Robinson buffer solution, which will be referred to as B.R. buffer A solution hereinafter), to adjust the pH of the resultant solution to 1.15. The temperature of the solution was kept at a constant temperature of 60° C. This buffer solution was added to each of the previously-prepared sample solutions 201 to 211 until the total amount would be 25 ml. Visible absorption spectra of the solution immediately after the preparation thereof and the solution after the storage thereof at 60° C. for 4 hours were measured with the ultraviolet/visible spectrometer made by Shimadzu Corp. Thus, respective absorbances were calculated at a maximum absorption wavelength.

The ratio of the concentration of the dye in the sample before the acid-induced fading test to the concentration of the dye in the sample after the acid-induced fading test (that is, remaining ratio (%)) was calculated, using the ratio of the absorbance of the sample before the acid-induced fading test to the absorbance of the sample after the acid-induced fading test. This ratio was used as an index for evaluation of fastness of a dye to acid. The results are shown in Table 3.

TABLE 3

| | Sample Solution No. | Kind of Coupler | Kind of dye | Remaining ratio (%) |
|---|---|---|---|---|
| Comparative Example 1 | 201 | Coupler for comparison (C-1) | CD-1 | 15 |
| Example 1 | 202 | Coupler(7) | D-1 | 97 |
| Example 2 | 203 | Coupler(10) | D-2 | 99 |
| Example 3 | 204 | Coupler(16) | D-3 | 98 |
| Example 4 | 205 | Coupler(18) | D-4 | 97 |
| Example 5 | 206 | Coupler(50) | D-5 | 96 |
| Example 6 | 207 | Coupler(51) | D-6 | 98 |
| Example 7 | 208 | Coupler(53) | D-7 | 93 |
| Example 8 | 209 | Coupler(73) | D-8 | 98 |
| Example 9 | 210 | Coupler(83) | D-9 | 92 |
| Example 10 | 211 | Coupler(84) | D-10 | 98 |

As is apparent from the results in Table 3, the dyes obtained from the dye-forming couplers of the present invention are quite excellent in fastness to acid.

Comparative Example 2

1. Preparation of an Emulsified Dispersion of the Coupler for Comparison (C-1)

Into 10 ml of ethyl acetate were dissolved 0.88 g of the coupler for comparison (C-1) and 2.6 g of tricresyl phosphate while heating. (This will be referred to as an oil phase solution.) Separately, 4.2 g of gelatin was added to 25 ml of water at room temperature, to swell the gelatin sufficiently. Thereafter, the resultant admixture was heated to 40° C., so that the gelatin was completely dissolved in water. While the temperature of this gelatin solution was kept at about 40° C., were added thereto 3 ml of a 5% aqueous sodium dodecylbenzenesulfonate solution and the previously-prepared oil phase solution. The resultant admixture was emulsified and dispersed with a homogenizer, to prepare an emulsified dispersion.

2. Preparation of a Light-Sensitive Material for Comparison

The thus-obtained emulsified dispersion of the coupler for comparison (C-1) was used, to produce a coating solution having the following composition. This coating solution was applied onto a polyethylene-laminated paper having an undercoat layer, in the manner that the amount of the silver halide emulsion would be 0.33 mmol/m$^2$ in terms of silver and the amount of the coupler would be 1 mmol/m$^2$. Gelatin was applied, as a protective layer, onto the resultant surface of the paper in the manner that the amount of the gelatin would be 2 g/m$^2$, to produce a sample 301 as a light-sensitive material for comparison.

| (Composition of the coating solution) | |
|---|---|
| Emulsion: silver chlorobromide<br>(This was composed of cubic grains, the substrate of which was silver chloride. A part of its surface locally contained 0.3 mol % (in total) of silver bromide. The average grain size thereof was 60 μm. Each of sensitizing dyes A, B and C was added thereto in an amount of 1.4 × $10^{-4}$ mole per mole of silver halide, to give spectral sensitivity.) | 13 g |
| 10% Gelatin | 28 g |
| Emulsified dispersion of the coupler for comparison (C-1) | 22 g |
| Water | 37 ml |
| 4% Sodium 1-hydroxy-3,5-dichloro-s-triazine aqueous solution | 5 ml |

(Sensitizing dye A)

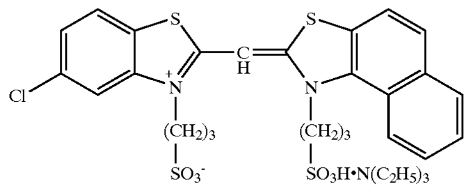

(Sensitizing dye B)

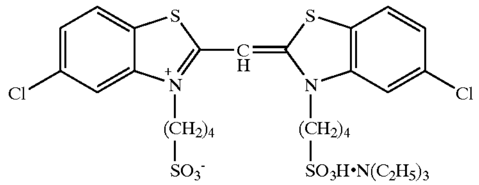

(Sensitizing dye C)

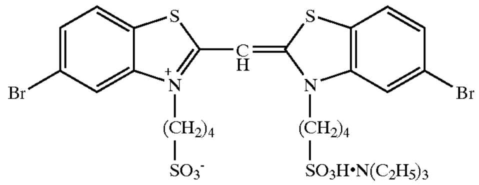

Examples 11 to 20

1. Preparation of Emulsified Dispersions of the Couplers (7), (10), (16), (18), (50), (51), (53), (73), (83) and (84)

The emulsified dispersions of the coupler of the present invention were prepared in the same manner as in Comparative Example 2, except that in "1. Preparation of an emulsified dispersion of a coupler for comparison (C-1)" in Comparative Example 2, any one of the above-mentioned exemplified couplers (7), (10), (16), (18), (50), (51), (53), (73), (83) and (84) in the present invention was used instead of the coupler for comparison (C-1), respectively, to prepare samples 302 to 311.

2. Preparation of Light-sensitive Materials of the Present Invention

The light-sensitive material samples 302 to 311 according to the present invention were prepared in the same manner as in Comparative Example 2, except that in "2. Preparation of a light-sensitive material for comparison" in Comparative Example 2, any one of the above-mentioned emulsified dispersions of the exemplified coupler (7), (10), (16), (18), (50), (51), (53), (73), (83) or (84) in the present invention was used instead of the emulsified dispersion of coupler for comparison (C-1), respectively, to produce the sample 302 wherein the coupler (7) was used, the sample 303 wherein the coupler (10) was used, the sample 304 wherein the coupler (16) was used, the sample 305 wherein the coupler (18) was used, the sample 306 wherein the coupler (50) was used, the sample 307 wherein the coupler (51) was used, the sample 308 wherein the coupler (53) was used, the sample 309 wherein the coupler (73) was used, the sample 310 wherein the coupler (83) was used, and the sample 311 wherein the coupler (84) was used.

<Color-image Fastness Evaluation Test>

Each of the samples 301 to 311, which were obtained in the above Comparative Example 2 and Examples 11 to 20, was subjected to a color-image fastness evaluation test in the following manner. Specifically, each of the samples was wedge-exposed to white light, followed by color-development through the following processing steps.

(Processing steps)

| Step | Temperature | Time |
|---|---|---|
| Color developing | 38.5° C. | 45 seconds |
| Bleach-fixing | 30 to 36° C. | 45 seconds |
| Stabilization (1) | 30 to 37° C. | 20 seconds |
| Stabilization (2) | 30 to 37° C. | 20 seconds |
| Stabilization (3) | 30 to 37° C. | 20 seconds |
| Drying | 70 to 85° C. | 70 seconds |

The respective steps of the color developing, the bleach-fixing, and the stabilization (1), (2) and (3) were carried out by immersing each of the samples into the following respective processing solutions under the above-mentioned conditions.

(Color-developing solution in the color-developing step)

| | |
|---|---|
| Water | 800 ml |
| Dimethylpolysiloxane-series surfactant (Silicone KF351A (trade name), manufactured by Shin-Etsu Chemical Co., Ltd.) | 0.1 g |
| Triethanolamine | 11.6 g |
| Ethylenediaminetetraacetic acid | 4.0 g |
| Sodium 4,5-dihydroxybenzene-1,3-disulfonate | 0.5 g |
| Potassium chloride | 10.0 g |
| Potassium bromide | 0.040 g |
| Triazinylaminostylbene-series fluorescent whitening agent (Hakkol FWA-SF (trade name), manufactured by Showa Chemicals Inc.) | 2.5 g |
| Sodium sulfite | 0.1 g |
| Disodium N,N-bis(sulfonatoethyl)hydroxylamine | 8.5 g |
| N-ethyl-N-(β-methanesulfonamidoethyl)-3-methyl-4-aminoaniline · 3/2 · sulfate · monohydrate | 5.0 g |
| Potassium carbonate | 26.3 g |
| Water to make | 1000 ml |

-continued

| | |
|---|---|
| pH (adjusted with potassium hydroxide and sulfuric acid at 25° C.) | 10.15 |
| (Bleach-fixing solution in the bleach-fixing step) | |
| Water | 800 ml |
| Iron (III) ammonium ethylenediaminetetraacetate | 47.0 g |
| Ethylenediaminetetraacetic acid | 1.4 g |
| m-Carboxymethylbenzenesulfinic acid | 8.3 g |
| Nitric acid (67%) | 16.5 g |
| Imidazole | 14.6 g |
| Ammonium thiosulfate aq. solution (750 g/liter) | 107 ml |
| Ammonium sulfite | 16.0 g |
| Potassium metabisulfite | 23.1 g |
| Water to make | 1000 ml |
| pH (adjusted with acetic acid and ammonia at 25° C.) | 6.0 |
| (Stabilizing solution in the stabilization (1) to (3) steps) | |
| Sodium chlorinated-isocyanurate | 0.02 g |
| Deionized water (electroconductivity: 5 μS/cm or less) | 1000 ml |
| pH | 6.5 |

Each of the processed samples formed yellow color, and the resultant hue of the samples 302 to 311 of the light-sensitive materials of the present invention were quite sharp, compared to that of the sample 301 of the light-sensitive material for comparison.

Then, each of the samples 301 to 311 subjected to the color-development processing was subjected to a wet heat-induced fading test under the conditions of temperature 80° C. and relative humidity 80%.

The developed color densities of each of the samples before and after the wet heat-induced fading test were measured with a TCD-type densitometer made by Fuji Photo Film Co., Ltd. The ratio between the developed color densities of a point having a developed color density of 2.0 before and after the wet heat-induced fading test (remaining ratio (%)) was calculated. This was used as an index for evaluating color-image fastness. The results are shown in Table 4.

TABLE 4

| | Sample No. | Kind of Coupler | Kind of dye | Remaining ratio (%) |
|---|---|---|---|---|
| Comparative Example 2 | 301 | Coupler for comparison (C-1) | CD-1 | 80 |
| Example 11 | 302 | Coupler(7) | D-1 | 99 |
| Example 12 | 303 | Coupler(10) | D-2 | 99 |
| Example 13 | 304 | Coupler(16) | D-3 | 99 |
| Example 14 | 305 | Coupler(18) | D-4 | 99 |
| Example 15 | 306 | Coupler(50) | D-5 | 99 |
| Example 16 | 307 | Coupler(51) | D-6 | 99 |
| Example 17 | 308 | Coupler(53) | D-7 | 99 |
| Example 18 | 309 | Coupler(73) | D-8 | 99 |
| Example 19 | 310 | Coupler(83) | D-9 | 98 |
| Example 20 | 311 | Coupler(84) | D-10 | 99 |

As is apparent from the results in Table 4, the light-sensitive materials of the present invention are excellent in fastness to humidity and heat.

Example 21

Surfaces of a support made of paper whose both the two surfaces were coated with a polyethylene resin were subjected to corona discharging treatment, and then a gelatin undercoat layer containing sodium dedecylbenzenesulfonate was provided on the support. Furthermore, photographic constituting layers composed of the 1st to 7th layers were successively provided by coating onto the undercoat layer. In this way, a sample (001) of a silver halide color photographic light-sensitive material having the following layer structure was made. Coating solutions for the respective photographic constituting layers were prepared as follows.

Preparation of a coating solution for the first layer

Into 23 g of a solvent (Solv-1) and 80 ml of ethyl acetate were dissolved 62 g of a yellow coupler (ExY), 8 g of a color-image stabilizer (Cpd-1), 4 g of a color-image stabilizer (Cpd-2), 8 g of a color-image stabilizer (Cpd-3) and 2 g of a color-image stabilizer (Cpd-8). This solution was emulsified and dispersed in 220 g of a 23.5 mass % aqueous gelatin solution containing 4 g of sodium dodecylbenzenesulfonate with a high-speed stirring emulsifier (dissolver). Water was added thereto, to prepare 900 g of an emulsified dispersion A.

On the other hand, a silver chlorobromide emulsion A (cubic; a 3:7 mixture of a large-size emulsion A having an average grain size of 0.72 μm, and a small-size emulsion A having an average grain size of 0.60 μm (in terms of mol of silver). The deviation coefficients of the grain size distribution were 0.08 and 0.10, respectively. Each size emulsion had 0.3 mol % of silver bromide locally contained in part of the grain surface whose substrate was made up of silver chloride) was prepared. To the large-size emulsion A of this emulsion, had been added $1.4 \times 10^{-4}$ mol, per mol of silver halide, of each of blue-sensitive sensitizing dyes A, B, and C shown below; and to the small-size emulsion A of this emulsion, had been added $1.7 \times 10^{-4}$ mol, per mol of silver halide, of each of the blue-sensitive sensitizing dyes A, B, and C shown below. Further, the chemical ripening of this emulsion was carried out optimally with a sulfur sensitizer and a gold sensitizer being added.

The above emulsified dispersion A and this silver chlorobromide emulsion A were mixed and dissolved, and the first-layer coating solution was prepared so that it would have the composition shown below. The coating amount of the emulsion is in terms of silver.

Preparation of Coating Solutions for the Second Layer to Seventh Layer

The coating solutions for the second layer to the seventh layer were prepared in the similar manner as that for the first-layer coating solution. As a gelatin hardener for each layer, 1-oxy-3,5-dichloro-s-triazine sodium salt was used. Further, to each layer, were added Ab-1, Ab-2, Ab-3, and Ab-4, so that the total amounts would be 15.0 mg/m$^2$, 60.0 mg/m$^2$, 5.0 mg/m$^2$, and 10.0 mg/m$^2$, respectively.

| | $R_1$ | $R_2$ |
|---|---|---|
| a | $—CH_3$ | $—NHCH_3$ |
| b | $—CH_3$ | $—NH_2$ |
| c | —H | $—NH_2$ |
| d | —H | $—NHCH_3$ |

-continued

| $R_1$ | $R_2$ |
|---|---|

(Ab-1) Antiseptic

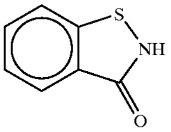

(Ab-2) Antiseptic

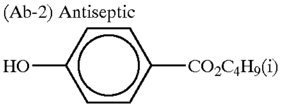

(Ab-3) Antiseptic

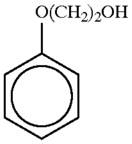

(Ab-4) Antiseptic

A mixture in 1:1:1:1(molar ratio) of a,b,c and d

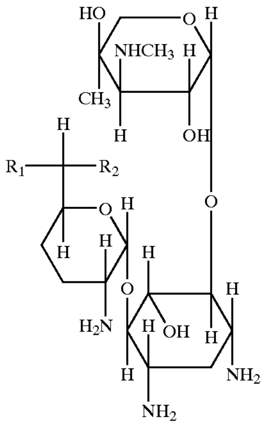

For the silver chlorobromide emulsion of the respective light-sensitive emulsion layer, the following spectral sensitizing dyes were used.

Blue-sensitive Emulsion Layer (Sensitizing dye A)

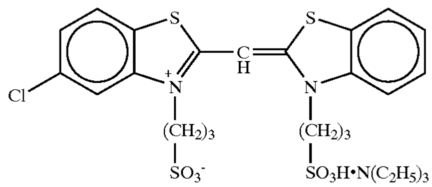

(Sensitizing dye B)

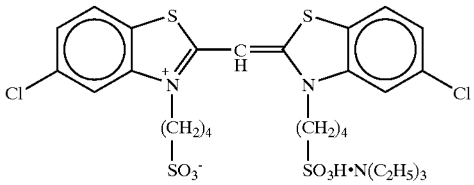

-continued (Sensitizing dye C)

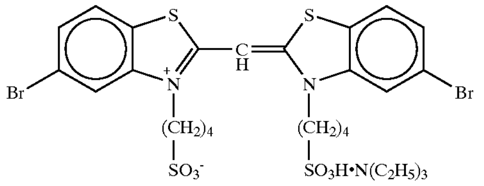

(The sensitizing dyes A, B, and C were added to the large-size emulsion in an amount of $1.4\times10^{-4}$ mol, respectively per mol of silver halide, and to the small-size emulsion in an amount of $1.7\times10^{-4}$ mol respectively per mol of silver halide.)

Green-Sensitive Emulsion Layer (The sensitizing dye D was added to the large-size emulsion in an amount of $3.0\times10^{-4}$ mol, and to the small-size emulsion in an amount of $3.6\times10^{-4}$ mol, per mol of the silver halide; the sensitizing dye E was added to the large-size emulsion in an amount of $4.0\times10^{-5}$ mol, and to the small-size emulsion in an amount of $7.0\times10^{-5}$ mol, per mol of the silver halide; and the sensitizing dye F was added to the large-size emulsion in an amount of $2.0\times10^{-4}$ mol, and to the small-size emulsion in an amount of $2.8\times10^{-4}$ mol, per mol of the silver halide.) Red-Sensitive Emulsion Layer (Sensitizing dye G)

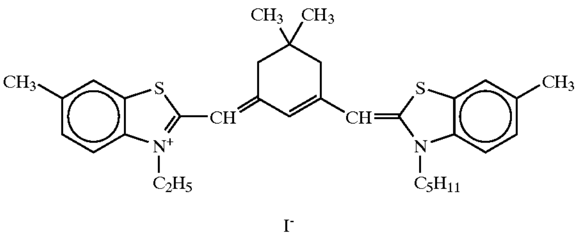

(Sensitizing dye D)

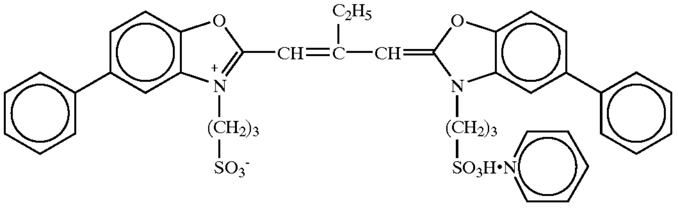

(Sensitizing dye E)

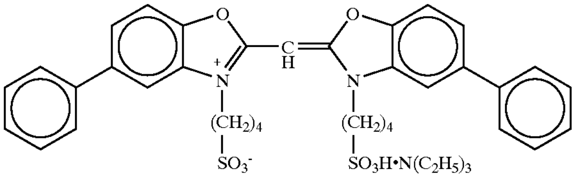

(Sensitizing dye F)

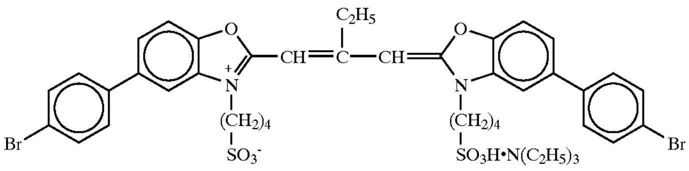

-continued (Sensitizing dye H)

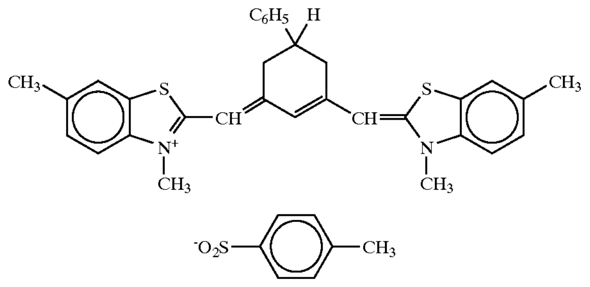

(The sensitizing dyes G, and H were added to the large-size emulsion in an amount of $6.0\times10^{-5}$ mol, respectively per mol of silver halide, and to the small-size emulsion in an amount of $9.0\times10^{-5}$ mol respectively per mol of silver halide.)

Further, the following compound I was added to the red-sensitive emulsion layer in an amount of $2.6\times10^{-3}$ mol per mol of the silver halide.

(Compound I)

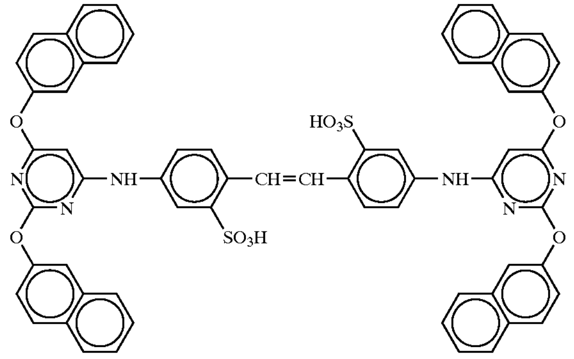

Further, to the blue-sensitive emulsion layer, the green-sensitive emulsion layer, and the red-sensitive emulsion layer, was added 1-(3-methylureidophenyl)-5-mercaptotetrazole in amounts of $3.3\times10^{-4}$ mol, $1.0\times10^{-3}$ mol, and $5.9\times10^{-4}$ mol, respectively, per mol of the silver halide. Further, the compound was also added to the second layer, the forth layer, the sixth layer, and the seventh layer, in amounts of 0.2 mg/$m^2$, 0.2 mg/$m^2$, 0.6 mg/$m^2$, and 0.1 mg/$m^2$, respectively.

Further, to the blue-sensitive emulsion layer and the green-sensitive emulsion layer, was added 4-hydroxy-6-methyl-1,3,3a,7-tetrazaindene in amounts of $1\times10^{-4}$ mol and $2\times10^{-4}$ mol, respectively, per mol of the silver halide.

Further, to the red-sensitive emulsion layer, was added a copolymer of methacrylic acid and butyl acrylate (1:1 in weight ratio; average molecular weight, 200,000 to 400,000) in an amount of 0.05 g/$m^2$.

Further, to the second layer, the fourth layer, and the sixth layer, was added a mixture of disodium catechol-3,5-disulfonate and 2,6-bishydroxyamino-4-dimetylamino-1,3,5-triazine (9:1 in molar ratio) in amounts of 6 mg/$m^2$, 6 mg/$m^2$, and 18 mg/$m^2$, respectively.

Further, in order to prevent irradiation, the following dyes (coating amounts are shown in parentheses) were added to the emulsion layers.

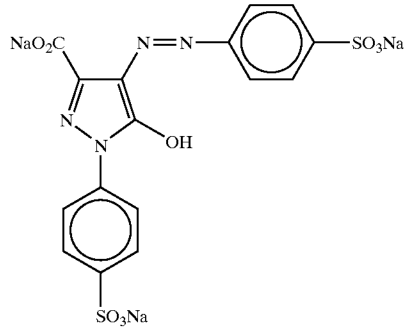

(10 mg/$m^2$)

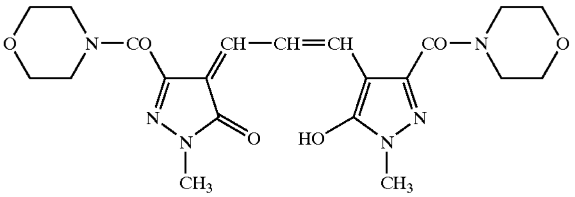

(20 mg/$m^2$)

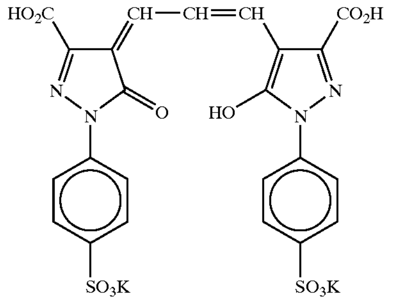

(5 mg/$m^2$)

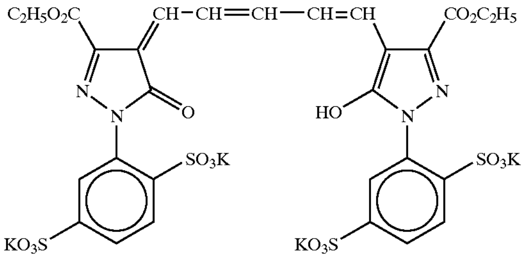

(20 mg/$m^2$)

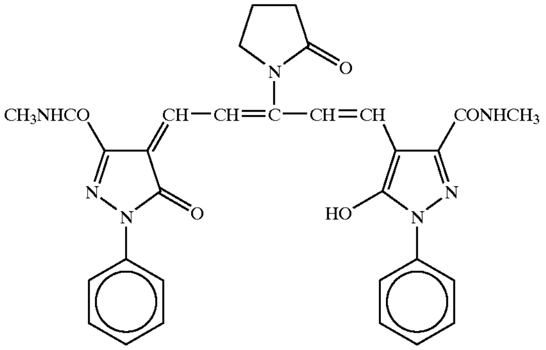

(20 mg/$m^2$)

(Layer Constitution)

The composition of each layer is shown below. The numbers show coating amounts ($g/m^2$). In the case of the silver halide emulsion, the coating amount is in terms of silver.

Support

Polyethylene Resin Laminated Paper

{The polyethylene resin on the first layer side contained a white pigment ($TiO_2$; content of 16 wt %, ZnO; content of 4 wt %), a fluorescent whitening agent (a mixture of 4,4'-bis(benzoxazolyl)stilbene and 4,4'-bis(5-methylbenzoxazolyl)stilbene mixed in a ratio of 8/2; content of 0.05 wt %) and a bluish dye (ultramarine)}

| | |
|---|---|
| First Layer (Blue-Sensitive Emulsion Layer) | |
| A silver chlorobromide emulsion A (cubic, a 3:7 mixture of a large-size emulsion A having an average grain size of 0.72 μm, and a small-size emulsion A having an average grain size of 0.60 μm (in terms of mol of silver). The deviation coefficients of the grain size distribution were 0.08 and 0.10, respectively. Each emulsion had 0.3 mol % of silver bromide contained locally in part of the grain surface whose substrate was made up of silver chloride) | 0.26 |
| Gelatin | 1.35 |
| Yellow coupler (ExY) | 0.62 |
| Color-image stabilizer (Cpd-1) | 0.08 |
| Color-image stabilizer (Cpd-2) | 0.04 |
| Color-image stabilizer (Cpd-3) | 0.08 |
| Color-image stabilizer (Cpd-8) | 0.02 |
| Solvent (Solv-1) | 0.23 |
| Second Layer (Color-Mixing Inhibiting Layer) | |
| Gelatin | 0.99 |
| Color-mixing inhibitor (Cpd-4) | 0.09 |
| Color-image stabilizer (Cpd-5) | 0.018 |
| Color-image stabilizer (Cpd-6) | 0.13 |
| Color-image stabilizer (Cpd-7) | 0.01 |
| Solvent (Solv-1) | 0.06 |
| Solvent (Solv-2) | 0.22 |
| Third Layer (Green-Sensitive Emulsion Layer) | |
| A silver chlorobromide emulsion B (cubic, a 1:3 mixture of a large-size emulsion B having an average grain size of 0.45 μm, and a small-size emulsion B having an average grain size of 0.35 μm (in terms of mol of silver). The deviation coefficients of the grain size distribution were 0.10 and 0.08, respectively. Each emulsion had 0.4 mol % of silver bromide contained locally in part of the grain surface whose substrate was made up of silver chloride) | 0.14 |
| Gelatin | 1.36 |
| Magenta coupler (ExM) | 0.15 |
| Ultraviolet absorbing agent (UV-1) | 0.05 |
| Ultraviolet absorbing agent (UV-2) | 0.03 |
| Ultraviolet absorbing agent (UV-3) | 0.02 |
| Ultraviolet absorbing agent (UV-4) | 0.03 |
| Ultraviolet absorbing agent (UV-6) | 0.01 |
| Color-image stabilizer (Cpd-2) | 0.02 |
| Color-image stabilizer (Cpd-4) | 0.002 |
| Color-image stabilizer (Cpd-6) | 0.09 |
| Color-image stabilizer (Cpd-8) | 0.02 |
| Color-image stabilizer (Cpd-9) | 0.03 |
| Color-image stabilizer (Cpd-10) | 0.01 |
| Color-image stabilizer (Cpd-11) | 0.0001 |
| Solvent (Solv-3) | 0.11 |
| Solvent (Solv-4) | 0.22 |
| Solvent (Solv-5) | 0.20 |
| Fourth Layer (Color-Mixing Inhibiting Layer) | |
| Gelatin | 0.71 |
| Color-mixing inhibitor (Cpd-4) | 0.06 |
| Color-image stabilizer (Cpd-5) | 0.013 |
| Color-image stabilizer (Cpd-6) | 0.10 |
| Color-image stabilizer (Cpd-7) | 0.007 |

-continued

| | |
|---|---|
| Solvent (Solv-1) | 0.04 |
| Solvent (Solv-2) | 0.16 |
| Fifth Layer (Red-Sensitive Emulsion Layer) | |
| A silver chlorobromide emulsion C (cubic, a 1:4 mixture of a large-size emulsion C having an average grain size of 0.50 μm, and a small-size emulsion C having an average grain size of 0.41 μm (in terms of mol of silver). The deviation coefficients of the grain size distribution were 0.09 and 0.11, respectively. Each emulsion had 0.5 mol % of silver bromide contained locally in part of the grain surface whose substrate was made up of silver chloride) | 0.20 |
| Gelatin | 1.11 |
| Cyan coupler (ExC-2) | 0.13 |
| Cyan coupler (ExC-3) | 0.03 |
| Color-image stabilizer (Cpd-1) | 0.05 |
| Color-image stabilizer (Cpd-6) | 0.05 |
| Color-image stabilizer (Cpd-7) | 0.02 |
| Color-image stabilizer (Cpd-9) | 0.04 |
| Color-image stabilizer (Cpd-10) | 0.01 |
| Color-image stabilizer (Cpd-14) | 0.01 |
| Color-image stabilizer (Cpd-15) | 0.03 |
| Color-image stabilizer (Cpd-16) | 0.05 |
| Color-image stabilizer (Cpd-17) | 0.05 |
| Color-image stabilizer (Cpd-18) | 0.06 |
| Color-image stabilizer (Cpd-19) | 0.06 |
| Solvent (Solv-5) | 0.15 |
| Solvent (Solv-8) | 0.05 |
| Solvent (Solv-9) | 0.10 |
| Sixth Layer (Ultraviolet Absorbing Layer) | |
| Gelatin | 0.66 |
| Ultraviolet absorbing agent (UV-1) | 0.19 |
| Ultraviolet absorbing agent (UV-2) | 0.06 |
| Ultraviolet absorbing agent (UV-3) | 0.06 |
| Ultraviolet absorbing agent (UV-4) | 0.05 |
| Ultraviolet absorbing agent (UV-5) | 0.08 |
| Ultraviolet absorbing agent (UV-6) | 0.01 |
| Solvent (Solv-7) | 0.25 |
| Seventh Layer (Protective Layer) | |
| Gelatin | 1.00 |
| Acryl-modified copolymer of polyvinyl alcohol (modification degree: 17%) | 0.04 |
| Liquid paraffin | 0.02 |
| Surface-active agent (Cpd-13) | 0.01 |

(ExY) Yellow coupler

A mixture in 60:40 (molar ratio) of

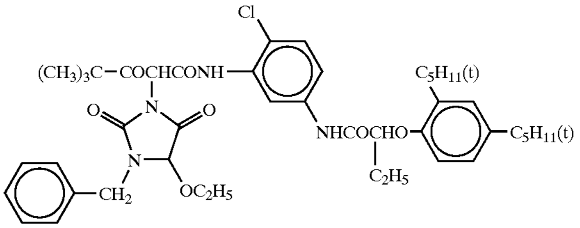

and

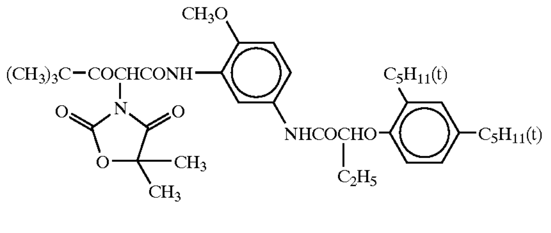

-continued (ExM) Magenta coupler

A mixture in 60:40 (molar ratio) of

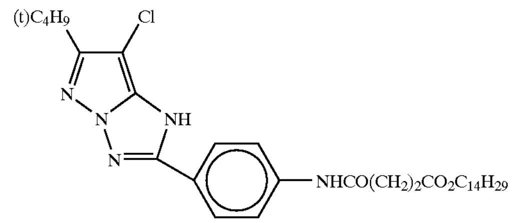

and

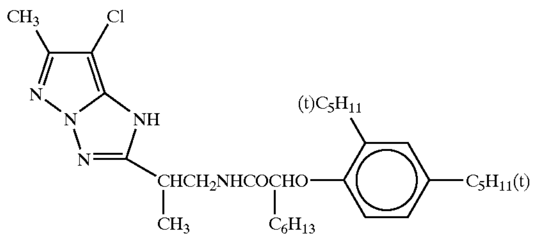

(ExC-1) Cyan coupler

A mixture in 15:85 (molar ratio) of

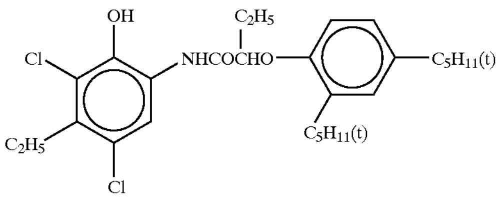

and

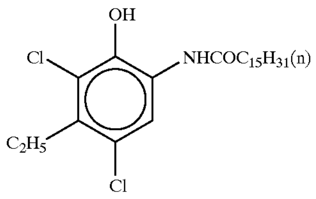

(ExC-2) Cyan coupler

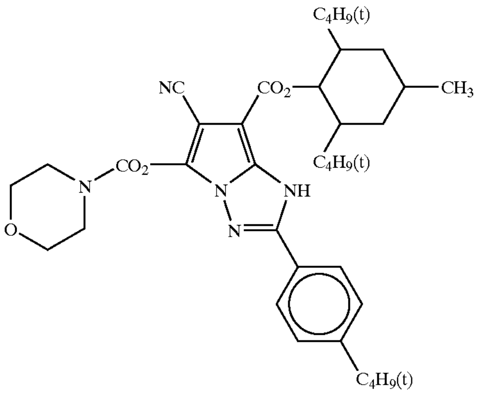

-continued (ExC-3) Cyan coupler

A mixture in 50:25:25 (molar ratio) of

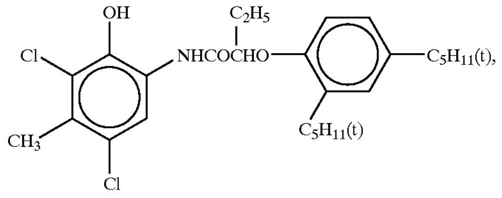

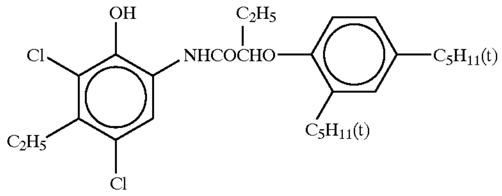

and

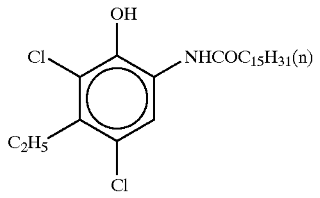

(Cpd-1) Color-image stabilizer

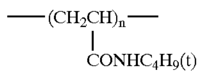

number-average molecular weight 60,000

(Cpd-2) Color-image stabilizer

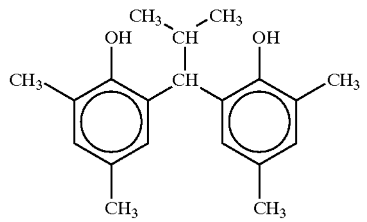

(Cpd-3) Color-image stabilizer

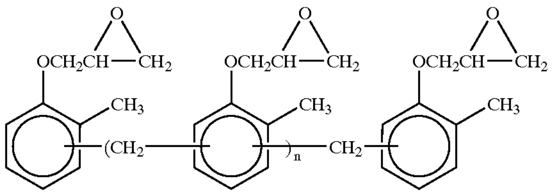

n = 7 ~ 8 (average value)

(Cpd-4) Color-mixing inhibitor

A mixture in 1:1:1 (molar ratio) of

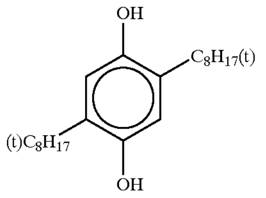

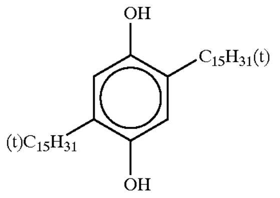

-continued
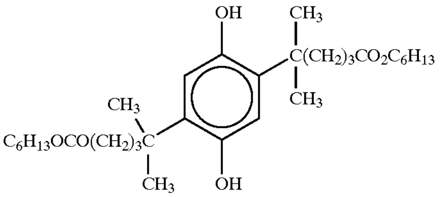
(Cpd-5) Color-mixing inhibiting auxiliary
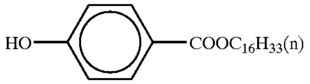
(Cpd-6) Stabilizer
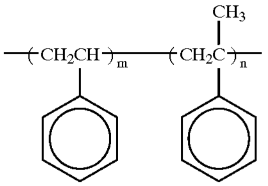
number-average molecular weight 600
m/n = 10/90
(Cpd-7) Color-mixing inhibitor
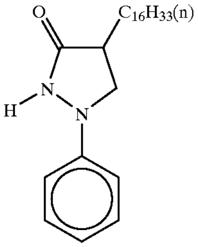
(Cpd-8) Color-image stabilizer
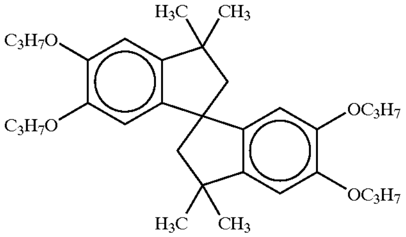
(Cpd-9) Color-image stabilizer
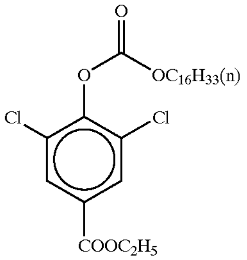
(Cpd-10) Color-image stabilizer
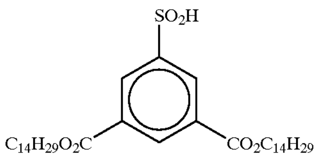
-continued
(Cpd-11)
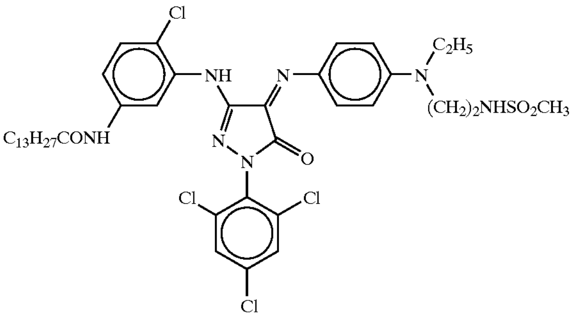
(Cpd-12)
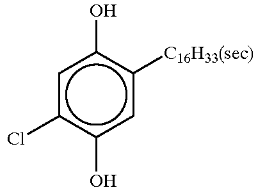
(Cpd-13)
A mixture in 7:3 (molar ratio) of
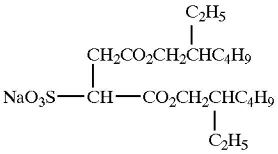
and
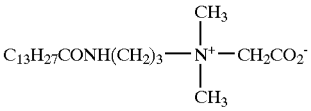
(Cpd-14)
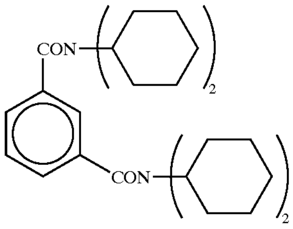
(Cpd-15)
A mixture in 1:1 (molar ratio) of
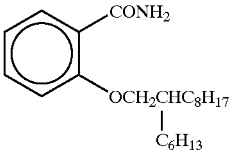
and
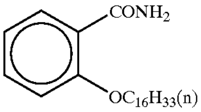
(Cpd-16)
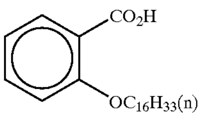
(Cpd-17)
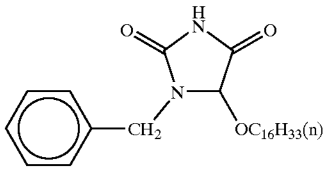

-continued (Cpd-18)

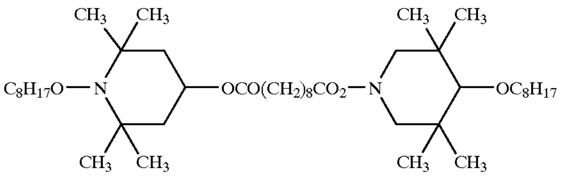

(Cpd-19)

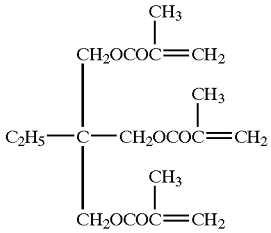

(UV-1) Ultraviolet absorbing agent

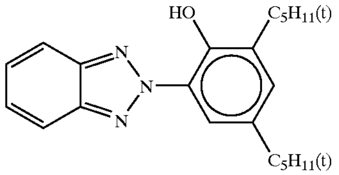

(UV-2) Ultraviolet absorbing agent

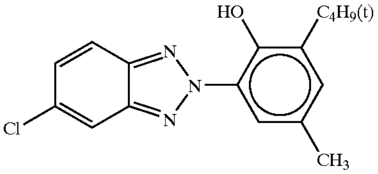

(UV-3) Ultraviolet absorbing agent

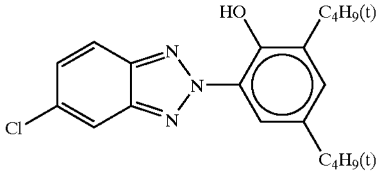

(UV-4) Ultraviolet absorbing agent

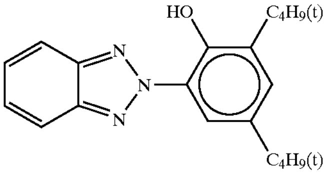

(UV-5) Ultraviolet absorbing agent

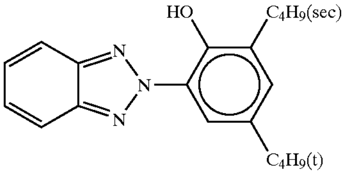

-continued (UV-6) Ultraviolet absorbing agent

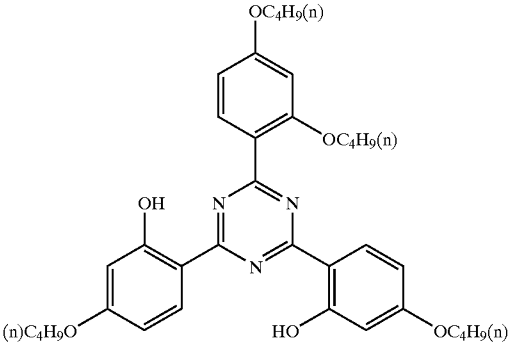

(Solv-1)

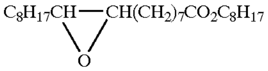

(Solv-2)

A mixture in 1:1 (mass ratio) of

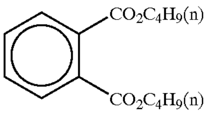

and

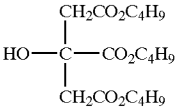

(Solv-3)

$C_4H_9OCO(CH_2)_8CO_2C_4H_9$ (Solv-4)

$O{=}P(OC_6H_{13}(n))_3$ (Solv-5)

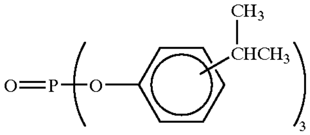

(Solv-6)

A mixture in 1:1 (mass ratio) of

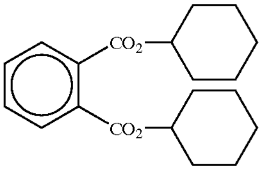

and

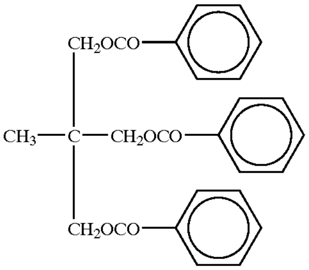

(Solv-7)

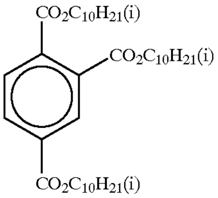

(Solv-8)

$C_8H_{17}OCO(CH_2)_8CO_2C_8H_{17}$

-continued (Solv-9)

A mixture in 1:1 (mass ratio) of

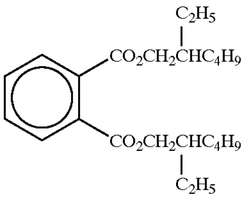

and

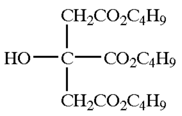

A light-sensitive material 401 was produced in the same manner as described above, except that the yellow coupler in the emulsified dispersion A for the first layer of the silver halide color photographic light-sensitive material (001) produced as above was replaced by an equimole amount of the coupler for comparison (C-1) used in the above-mentioned Comparative Example 1. Light-sensitive materials (402) to (411) were produced in the same manner as the light-sensitive material 401, except that the coupler for comparison (C-1) was replaced by an equimole amount of any one of the dye-forming couplers (7), (10), (16), (18), (50), (51), (53), (73), (83) and (84) of the present invention, respectively.

The average particle sizes of the thus-prepared yellow-coupler-containing oleophilic fine-particle dispersions each were in the range of 0.10 to 0.20 μm.

The above-described light-sensitive material (001) was stored in the condition of 25° C.—55% RH, for 10 days, and then, made into a roll with a width of 127 mm; the rolled light-sensitive material was exposed to light imagewise, using a mini-lab printer processor PP1258AR, trade name, manufactured by Fuji Photo Film Co., Ltd.; and then, the continuously processing (running test) in the following processing steps was carried out, until the replenishment reached to be equal to twice the color-development tank volume.

| Processing step | Temperature | Time | Replenishment rate* |
|---|---|---|---|
| Color development | 38.5° C. | 45 sec | 45 ml |
| Bleach-fixing | 38.0° C. | 45 sec | 35 ml |
| Rinse (1) | 38.0° C. | 20 sec | — |
| Rinse (2) | 38.0° C. | 20 sec | — |
| Rinse (3) | **38.0° C. | 20 sec | — |
| Rinse (4) | **38.0° C. | 30 sec | 121 ml |

*Replenishment rate per $m^2$ of the light-sensitive material to be processed.
**A rinse cleaning system RC50D, manufactured by Fuji Photo Film Co., Ltd., was installed in the rinse (3), and the rinse solution was taken out from the rinse (3) and sent to a reverse osmosis membrane module (RC50D) by using a pump.The permeated water obtained in that tank was supplied to the rinse (4), and the concentrated water was returned to the rinse (3). Pump pressure was controlled such that the water to be permeated in the reverse osmosis module would be maintained in an amount of 50 to 300 ml/min, and the rinse solution was circulated under controlled temperature for 10 hours a day. (The rinse was made in a tank counter-current system from (1) to (4).)

The composition of each processing solution was as follows.

| | (Tank solution) | (Replenisher) |
|---|---|---|
| (Color developer) | | |
| Water | 800 ml | 800 ml |
| Dimethylpolysiloxane-series surfactant (Silicone KF351A/trade name, Shin-Etsu Chemical Co., Ltd.) | 0.1 g | 0.1 g |
| Triethanolamine | 11.6 g | 11.6 g |
| Ethylenediamine tetraacetic acid | 4.0 g | 4.0 g |
| Sodium 4,5-dihydroxybenzene-1,3-disulfonate | 0.5 g | 0.5 g |
| Potassium chloride | 10.0 g | — |
| Potassium bromide | 0.040 g | 0.010 g |
| Triazinylaminostilbene-series fluorescent whitening agent (Hakkol FWA-SF/trade name, Showa Chemical Industry Co., Ltd.) | 2.5 g | 5.0 g |
| Sodium sulfite | 0.1 g | 0.1 g |
| Disodium-N,N-bis(sulfonatoethyl) hydroxylamine | 8.5 g | 11.1 g |
| N-ethyl-N-(β-methanesulfonamidoethyl)-3-methyl-4-amino-4-aminoaniline · 3/2 sulfate · 1 hydrate | 5.0 g | 15.7 g |
| Potassium carbonate | 26.3 g | 26.3 g |
| Water to make | 1000 ml | 1000 ml |
| pH (25° C./adjusted using potassium hydroxide and sulfuric acid) | 10.15 | 12.50 |
| (Bleach-fixing solution) | | |
| Water | 800 ml | 800 ml |
| Ammonium iron (III) ethylenediaminetetraacetate | 47.0 g | 94.0 g |
| Ethylenediamine tetraacetic acid | 1.4 g | 2.8 g |
| m-Carboxymethylbenzenefulfinic acid | 8.3 g | 16.5 g |
| Nitric acid (67%) | 16.5 g | 33.0 g |
| Imidazole | 14.6 g | 29.2 g |
| Ammonium thiosulfate (750 g/l) | 107 ml | 214 ml |
| Ammonium sulfite | 16.0 g | 32.0 g |
| Potassium methbisulfite | 23.1 g | 46.2 g |
| Water to make | 1000 ml | 1000 ml |

-continued

| | (Tank solution) | (Replenisher) |
|---|---|---|
| pH (25 °C./adjusted using acetic acid and ammonia) | 6.0 | 6.0 |
| (Rinse solution) | | |
| Sodium chlorinated-isocyanurate | 0.02 g | 0.02 g |
| Deionized water (conductivity: 5 μS/cm or less) | 1000 ml | 1000 ml |
| pH | 6.5 | 6.5 |

Then, each of the samples was subjected to gradation exposure using a sensitometer (Model FWH, produced by Fuji Photo Film Co., Ltd., whose light source had a color temperature of 3,200° K) through three-color separation optical wedges for sensitometry. The exposure was carried out under the condition such that the exposure time was 0.1 seconds and the exposure amount was 250 1×·sec.

Separately, the respective light-sensitive materials were subjected to the following scanning exposure.

For the scanning exposure, a scanning exposure equipment shown in FIG. 1 in JP-A-8-16238 was used. About light sources, a semiconductor laser was used to obtain a 688-nm light source (R light). The semiconductor laser was combined with SHG to obtain a 532-nm light source (G light) and a 473-nm light source (B light). An external modulator was used to modulate the light quantity of the R light. The modulated light was caused to be reflected on a rotary polyhedron. Using the reflected light, each sample was subjected to scanning exposure while the sample was moved perpendicularly to the scanning direction. The scanning exposure was carried out at 400 dpi. The average exposure time was $8\times10^{-8}$ seconds per pixel. To suppress fluctuation in light quantity from the semiconductor laser, due to change in temperature, a Peltier element was used to make the temperature constant.

The respective exposed samples were subjected to development with the above-mentioned running processing solutions, and then the same evaluations as for the light-sensitive materials in Comparative Example 2 and Examples 11 to 20 were carried out.

The results demonstrated that each of the dye-forming couplers of the present invention was sufficiently high in color-forming property, and excellent in hue and fastness of the resultant dye.

Example 22

A light-sensitive material was produced in the same manner as Sample 101 in JP-A-11-305396, except that ExY-2 and ExY-3, which were contained in the 13th layer and the 14th layer of the Sample 101 in JP-A-11-305396, were replaced by an equimole amount of the dye-forming coupler (53) of the present invention, respectively. The thus-prepared light-sensitive material was exposed to light, and subjected to development, in the same manner as described in the Example 1 of JP-A-11-305396. The processed light-sensitive material was then evaluated in the same manner as described in the above Examples in the present specification of the present application. As a result, the similar results as in the above Example 17 of the present specification were obtained.

Example 23

A light-sensitive material was produced in the same manner as Sample 107 in Example 1 in JP-A-11-84601, except that couplers C-5, C-6 and C-10, which were contained in the 13th layer and 14th layer of the sample 107 in the Example 1 of JP-A-11-84601, and C-6 and C-10, which were contained in the 15th layer, were replaced by an equimole amount of the dye-forming coupler (53) of the present invention, respectively. The thus-prepared light-sensitive material was exposed to light, and subjected to development, in the same manner as described in the Example 1 of JP-A-11-84601. The processed light-sensitive material was then evaluated in the same manner as described in the above Examples in the present specification of the present application. As a result, the similar results as in the above Example 17 of the present specification were obtained.

Example 24

A light-sensitive material for comparison, Sample 101B, was produced in the same manner as the Sample 301 in the aforementioned Comparative Example 2, except that the average grain size of the silver chlorobromide grains in the silver halide emulsions was made to 7 μm.

(Production of Samples 102B to 106B)

Samples 102B to 106B were produced in the same manner as the sample 101B, except that any one of the couples, as shown in Table 5, of the present invention, was used instead of the coupler for comparison.

Each of the samples produced as described above was wedge-exposed to white light, followed by color-development processing in the same processing steps as used in the above Comparative Example 2 and Examples 11 to 20.

About the measurement of the density of the processed samples, a densitometer X RITE 404, trade name, made by X Rite Inc., was used to measure the reflection density (in yellow) thereof. The resultant results are collectively described in Table 5.

TABLE 5

| Sample No. | Coupler | $D_{max}$ (maximum density) | Remarks |
|---|---|---|---|
| 101B | C-1 | 2.0 | Comparative Example |
| 102B | (1)' | 2.4 | This invention |
| 103B | (3)' | 2.3 | This invention |
| 104B | (5)' | 2.2 | This invention |
| 105B | (7)' | 2.4 | This invention |
| 106B | (9)' | 2.6 | This invention |

As is apparent from the results in Table 5, each of the couplers of the present invention were excellent in color-forming property.

Further, the samples according to the present invention were excellent in hue of yellow, contrary to the sample for comparison.

Example 25

Sample (001B) was prepared in the same manner as the sample (001) in Example 21, except that the color-dye stabilizer (Cpd-8) was not used to contain in the first layer, and that, to the second layer, fourth layer and sixth layer, was added disodium catechol-3,5-disulfonate in amounts of 6 $mg/m^2$, 6 $mg/m^2$ and 18 $mg/m^2$, respectively, in stead of the above-described mixture of disodium catechol-3,5-disulfonate and 2,6-bishydroxyamino-4-dimetylamino-1,3,5-triazine as used in Example 21.

A light-sensitive material 201B was prepared in the same manner as the thus-prepared silver halide color photographic light-sensitive material (001B), except that the yellow coupler in the emulsified dispersion A for the first layer of the silver halide color photographic light-sensitive material (001B) was replaced by an equimole amount of the above coupler for comparison (C-1) used in the Comparative Example 1. Similarly, light-sensitive materials (202B) to (206B) were prepared in the same manner as described above, except that the yellow coupler was replaced by an equimole amount of any one of the couplers (1)', (3)', (5)', (7)' and (9)' as used in the Example 24, respectively.

The respective exposed samples were processed with the running processing solution in the same manner as in the above Example 21, and then the same evaluations as for the light-sensitive materials in Example 24 were carried out.

The results demonstrated that each of the dye-forming couplers of the present invention had quite high color-forming property.

Example 26

A light-sensitive material was produced in the same manner as Sample 101 in JP-A-11-305396, except that ExY-2 and ExY-3, which were contained in the 13th layer and the 14th layer of the sample 101 in JP-A-11-305396, were replaced by an equimole amount of the coupler (1)' of the present invention, respectively. The thus-prepared light-sensitive material was exposed to light, and subjected to development, in the same manner as in the Example 1 of JP-A-11-305396. The processed light-sensitive material was then evaluated in the same manner as described in the above Examples in the present specification of the present application. As a result, similarly to the above Example 24 of the present specification, it was confirmed that each couplers of the present invention were quite high in color-forming property.

Example 27

A light-sensitive material was produced in the same manner as Sample 107 in Example 1 in JP-A-11-84601, except that couplers C-5, C-6 and C-10, which were contained in the 13th layer and 14th layer of the sample 107 in the Example 1 of JP-A-11-84601, and C-6 and C-10, which were contained in the 15th layer, were replaced by an equimole amount of the coupler (1)' of the present invention, respectively. The thus-prepared light-sensitive material was exposed to light, and subjected to development, in the same manner as described in the above Example 1 of JP-A-11-84601. The processed light-sensitive material was then evaluated in the same manner as described in the above Examples in the present specification of the present application. As a result, similarly to the above Example 24 of the present specification, it was confirmed that each couplers of the present invention were quite high in color-forming property.

Having described our invention as related to the present embodiments, it is our intention that the invention not be limited by any of the details of the description, unless otherwise specified, but rather be construed broadly within its spirit and scope as set out in the accompanying claims.

What is claimed is:

1. A method for producing an azomethine dye, comprising reacting a dye forming coupler compound represented by the following formula (I):

(I)

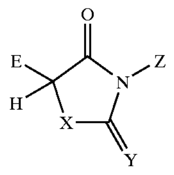

wherein E represents an aryl group or heterocyclic group, or a —C(=O)W group, in which W represents a nitrogen-containing heterocyclic group, Z represents an aryl group or a heterocyclic group, and X and Y each independently represent =O, =S, or =N—R, in which R represents a substituent, with the proviso that when E represents an aryl group or a heterocyclic group, X and Y each represent =O, and that when E represents a —C(=O)W group, Z represents a substituted aryl group, with an oxidized product of a developing agent.

2. The method of claim 1, wherein the compound represented by formula (I) is a compound represented by the following formula (IA):

(IA)

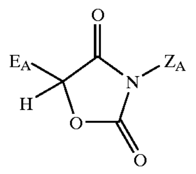

wherein $E_A$ and $Z_A$ each independently represent an aryl group or a heterocyclic group.

3. The method of claim 2, wherein $E_A$ is an aryl or heterocyclic group, having a substituent on at least one position adjacent to the carbon atom bonded to the oxazolidinedione ring.

4. The method of claim 2, wherein $E_A$ is an aryl or heterocyclic group, having substituents on both of positions adjacent to the carbon atom bonded to the oxazolidinedione ring.

5. The method of claim 2, wherein $E_A$ is a heterocyclic group.

6. The method of claim 5, wherein the compound represented by formula (IA) is a compound represented by the following formula (II):

(II)

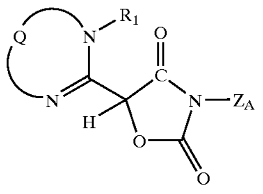

wherein $Z_A$ represents an aryl group or a heterocyclic group, Q represents a group of atoms composed of carbon atoms and/or hetero atoms necessary to form, together with the N—C═N, a 5-, 6- or 7-membered ring, and $R_1$ represents a substituent.

7. The method of claim 6, wherein, in the compound represented by formula (II), Q is represented by the following formula (III):

(III)

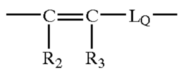

wherein $L_Q$ represents a carbonyl or sulfonyl group, and $R_2$ and $R_3$, which are the same or different, each represent a hydrogen atom or a substituent, or $R_2$ and $R_3$ may bond together to form a ring.

8. The method of claim 7, wherein $L_Q$ is a carbonyl group.

9. The method of claim 2, wherein $Z_A$ is a heterocyclic group.

10. The method of claim 2, wherein $Z_A$ is an aryl group having a substituent on an ortho position thereof.

11. The method of claim 2, wherein the compound represented by formula (IA) is a compound represented by the following formula (IV):

(IV)

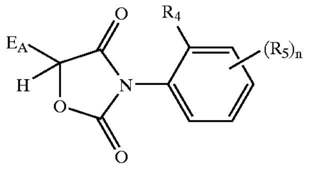

wherein $E_A$ represents an aryl group or a heterocyclic group; $R_4$ represents a halogen atom, an alkoxy group, or an aryloxy group; $R_5$ represents a substituent; and n is an integer of 0, or 1 to 4; when n is an integer of 2 to 4, $R_5$'s each are the same or different; or the groups adjacent to each other among $R_4$ and $R_5$('s) may bond together to form a ring.

12. The method of claim 2, wherein the compound represented by formula (IA) is a compound represented by the following formula (V):

(V)

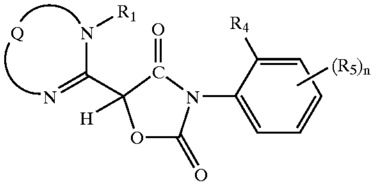

wherein Q is a group represented by the following formula (III), $R_1$ represents a substituent, $R_4$ represents a halogen atom, an alkoxy group, or an aryloxy group, $R_5$ represents a substituent, n is an integer of 0 or 1 to 4; when n is an integer of 2 to 4, $R_5$'s each may be the same or different, or the groups adjacent to each other among $R_4$ and $R_5$('s) may bond together to form a ring:

(III)

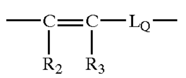

wherein $L_Q$ represents a carbonyl or sulfonyl group, and $R_2$ and $R_3$, which are the same or different, each represent a hydrogen atom or a substituent, or $R_2$ and $R_3$ may bond together to form a ring.

13. The method of claim 2, wherein a p-phenylenediamine compound is reacted together with the compound represented by formula (IA).

14. The method of claim 1, wherein the compound represented by formula (I) is a compound represented by the following formula (IB):

(IB)

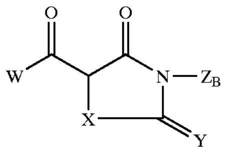

wherein W represents a nitrogen-containing heterocyclic group, $Z_B$ represents a substituted aryl group, and X and Y each independently represent ═O, ═S, or ═N—R, in which R represents a substituent.

15. The method of claim 14, wherein $Z_B$ is a phenyl group substituted by a halogen atom or an alkoxy group on the 2-position thereof, and having a substituent on the 5-position thereof.

16. The method of claim 14, wherein $Z_B$ is a phenyl group substituted by a halogen atom or an alkoxy group on the 2-position thereof, and having a substituent on the 5-position thereof; and X and Y each represent ═O.

17. The method of claim 14, wherein a p-phenylenediamine compound is reacted together with the compound represented by formula (IB).

18. The method of claim 1, wherein a p-phenylenediamine compound is reacted together with the compound represented by formula (I).

19. A dye-forming coupler represented by the following formula (IA):

(IA)

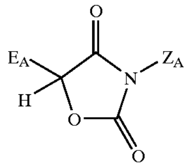

wherein $E_A$ represents a heterocyclic group and $Z_A$ represents an aryl group or a heterocyclic group.

20. A dye-forming coupler represented by the following formula (IB):

(IB)

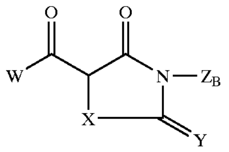

wherein W represents a nitrogen-containing heterocyclic group, $Z_B$ represents a substituted aryl group, and X and Y each independently represent ═O, ═S, or ═N—R, in which R represents a substituent.

* * * * *